(12) United States Patent
Schuster et al.

(10) Patent No.: US 8,952,150 B2
(45) Date of Patent: Feb. 10, 2015

(54) PROSTAGLANDIN TRANSPORTER INHIBITORS AND USES THEREOF

(75) Inventors: Victor L. Schuster, New York, NY (US); Yuling Chi, New Rochelle, NY (US); Andrew S. Wasmuth, Brooklyn, NY (US); Richard S. Pottorf, Belle Meade, NJ (US); Gary L. Olson, Mountainside, NJ (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 219 days.

(21) Appl. No.: 13/394,857

(22) PCT Filed: Sep. 20, 2010

(86) PCT No.: PCT/US2010/002555
§ 371 (c)(1),
(2), (4) Date: Jun. 4, 2012

(87) PCT Pub. No.: WO2011/037610
PCT Pub. Date: Mar. 31, 2011

(65) Prior Publication Data
US 2012/0238577 A1  Sep. 20, 2012

Related U.S. Application Data

(60) Provisional application No. 61/277,291, filed on Sep. 23, 2009.

(51) Int. Cl.
| | | |
|---|---|---|
| C07D 251/70 | (2006.01) |
| C07D 403/12 | (2006.01) |
| A61K 31/53 | (2006.01) |
| A61P 19/02 | (2006.01) |
| A61K 9/00 | (2006.01) |
| A61K 9/06 | (2006.01) |
| A61K 9/107 | (2006.01) |
| A61K 9/127 | (2006.01) |

(52) U.S. Cl.
CPC ............. *A61K 9/0043* (2013.01); *A61K 9/0014* (2013.01); *A61K 9/0019* (2013.01); *A61K 9/0031* (2013.01); *A61K 9/06* (2013.01); *A61K 9/1075* (2013.01); *A61K 9/127* (2013.01)
USPC ........... 544/196; 544/197; 544/198; 544/204; 544/211; 544/212; 514/245

(58) Field of Classification Search
USPC ................. 544/196, 197, 198, 204, 211, 212; 514/245
See application file for complete search history.

(56) References Cited

U.S. PATENT DOCUMENTS

| | | |
|---|---|---|
| 6,262,053 B1 | 7/2001 | Uckun et al. |
| 2006/0194803 A1 | 8/2006 | Kubota et al. |
| 2006/0293325 A1 | 12/2006 | Chang et al. |
| 2008/0227785 A1 | 9/2008 | Kubota et al. |
| 2009/0233933 A1 | 9/2009 | Schuster et al. |

FOREIGN PATENT DOCUMENTS

| | | |
|---|---|---|
| EP | 1479397 A1 | 11/2004 |
| WO | 9710887 A1 | 3/1997 |
| WO | 0078738 A1 | 12/2000 |

OTHER PUBLICATIONS

Krotz et al. J. Vasc. Res. 42:312-324, 2005.*
Dajani et al. J Physiol Pharmacol. Aug. 2008;59 Suppl 2:117-33.*
Green et al. Curr Opin Nephrol Hypertens. Jan. 2012 ; 21(1): 7-14.*
Freshney et al., Culture of Animal Cells, A Manual of Basic Technique, Alan R. Liss, Inc., 1983, New York, p. 4.*
Dermer et al., Bio/Technology, 1994, 12:320.*
Cecil Textbook of Medicine, edited by Bennet, J.C., and Plum F., 20th edition, vol. 1, 1004-1010, 1996.*
Supplementary European Search Report for counterpart European Application No. 10819142.0, dated Jul. 4, 2013.
Campbell Jr et al. "Unsymmetrically Substituted Melamines." Journal of Organic Chemistry vol. 26, pp. 2786-2789, 1961.
Kling A et al., entitled "Uber UV-absorbierende Substanzen mit reaktivem Charakter," Seifen, Oele, Fette, Waschse, 1963, 89(22), 744-748.
CAS RN 328014-21-7, STN Entry Date Mar. 19, 2001; CAS RN 500147-67-1, STN Entry Date Mar. 20, 2003; CAS RN 452074-97-4, STN Entry Date Sep. 17, 2002; RN 452074-59-8, STN Entry Date Sep. 17, 2002; and CAS RN 434298-61-0, STN Entry Date Jun. 27, 2002.
Australian Patent Examination Report issued Jul. 8, 2014 in connection with patent application No. 2010298720.
PCT International Search Report dated Nov. 18, 2010 in connection with PCT International Patent Application No. PCT/US2010/002555, 5 pages.
PCT Written Opinion of the International Searching Authority dated Nov. 18, 2010 in connection with PCT International Patent Application No. PCT/US2010/002555, 4 pages.

\* cited by examiner

*Primary Examiner* — Venkataraman Balasubramanian
(74) *Attorney, Agent, or Firm* — Amster, Rothstein & Ebenstein LLP

(57) ABSTRACT

Disclosed are compounds for inhibiting prostaglandin transporter (PGT) activity, pharmaceuticals compositions including the compounds, and methods of treating subjects using the compounds.

31 Claims, 1 Drawing Sheet

PROSTAGLANDIN TRANSPORTER INHIBITORS AND USES THEREOF

CROSS-REFERENCE TO RELATED APPLICATIONS

This application is a U.S. national stage entry under 35 U.S.C. §371 of PCT International Patent Application No. PCT/US2010/002555, filed Sep. 20, 2010, and claims priority to U.S. Provisional Patent Application No. 61/277,291, filed Sep. 23, 2009, the contents of which are incorporated herein by reference in their entirety.

BACKGROUND OF THE INVENTION

Various publications are referred to in parentheses throughout this application. Full citations for these references may be found at the end of the specification immediately preceding the claims. The disclosures of these publications are hereby incorporated by reference in their entireties into the subject application to more fully describe the art to which the subject application pertains.

Prostaglandins (PGs) are synthesized from arachidonic acid by cyclooxygenases (COX1 and COX2) and corresponding synthases (Helliwell et al. 2004). PGs play an important role in physiology and clinical settings. Their biological effects include triggering inflammation, fever and pain (Blatteis and Sehic, 1997; Bley et al., 1998; Vanegas and Schaible, 2001; Samad et al., 2002); induction of labor (Ulmann et al., 1992); modulation of renal hemodynamics and of water and solute reabsorption (Epstein, 1986; Wang et al., 1998; Yokoyama et al., 2002); arterial vasodilatation (Clyman et al., 1978; Coceani and Olley, 1988; Smith et al., 1994); stimulation of cell proliferation and angiogenesis (Ferrara et al, 1997; Tsujii et al, 1998; Young, 2004; Mann et al, 2006; Sheng et al, 2001; Shao et al, 2006); and mediating sensitization of sensory neurons (Southall and Vasko, 2000; Southall and Vasko, 2001; Seybold et al., 2003). PG analogues, such as latanoprost and unoprostone, have been used to treat glaucoma (Stjernschantz, 1995; Alm, 1998; Susanna et al., 2002; Stjernschantz, 2004). At the cellular level, PGs are involved in several major signaling pathways, including the mitogen-activated protein (MAP) kinase and protein kinase A pathways by upregulation of cAMP (Narumiya et al., 1999; Bos et al., 2004).

The magnitude of PG effects depends not only on their production but also their metabolism. The prostaglandin transporter (PGT) (Kanai et al., 1995; U.S. Pat. No. 5,792,851) removes PGs from the extracellular compartment and thereby terminates their interactions with receptors on cell membranes. PGT delivers PGs to cytoplasmic 15-OH PG dehydrogenase (Schuster, 2002; Nomura et al., 2004), resulting in oxidation and inactivation. Because PGT is highly expressed in the tissues and organs where PGs are synthesized (Bao et al., 2002), and because PGT regulates a broad and complex PG signaling system, inhibitors of PGT are important for manipulating signaling. Inhibition of PGT lowers blood pressure by vasodilation and natriuresis and inhibits platelet aggregation (Chi et al., 2009).

Known PGT blockers include inhibitors of the organic anion transporters (OATS), such as bromcresol green and bromosulfophthalein, and some COX2 inhibitors, such as indomethacin and ibuprofen (Bito and Salvador, 1976; Kanai et al., 1995). One of the main problems with these inhibitors is that they are not specific for PGT (Jacquemin et al., 1994; Sweet et al., 1997). Recently, specific PGT inhibitors have been developed (Chi et al., 2005; WO 2007/136638). The present invention addresses the need for even more potent specific inhibitors of PGT.

SUMMARY OF THE INVENTION

The invention provides compounds that inhibit prostaglandin transporter (PGT) activity, where the compounds are represented by the structure

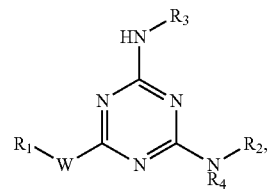

where the variables R1, R2, R3, R4 and W are defined herein below.

The invention provides pharmaceutical compositions comprising any of the compounds disclosed herein and a pharmaceutically acceptable carrier.

The invention is further directed to methods of inhibiting prostaglandin transporter (PGT) activity in a subject comprising administering to the subject any of the compounds disclosed herein in an amount effective to inhibit PGT activity.

The invention also provides methods of inhibiting cyclooxygenase 2 (COX2) activity in a subject comprising administering to the subject any of the compounds disclosed herein in an amount effective to inhibit COX2 activity.

The invention further provides a method of treating a subject with a disease or disorder associated with prostaglandin activity and/or COX2 activity comprising administering to the subject any of the compounds disclosed herein in an amount effective to inhibit prostaglandin transporter (PGT) activity and/or COX2 activity.

DETAILED DESCRIPTION OF THE INVENTION

Figures 1A, 1B:
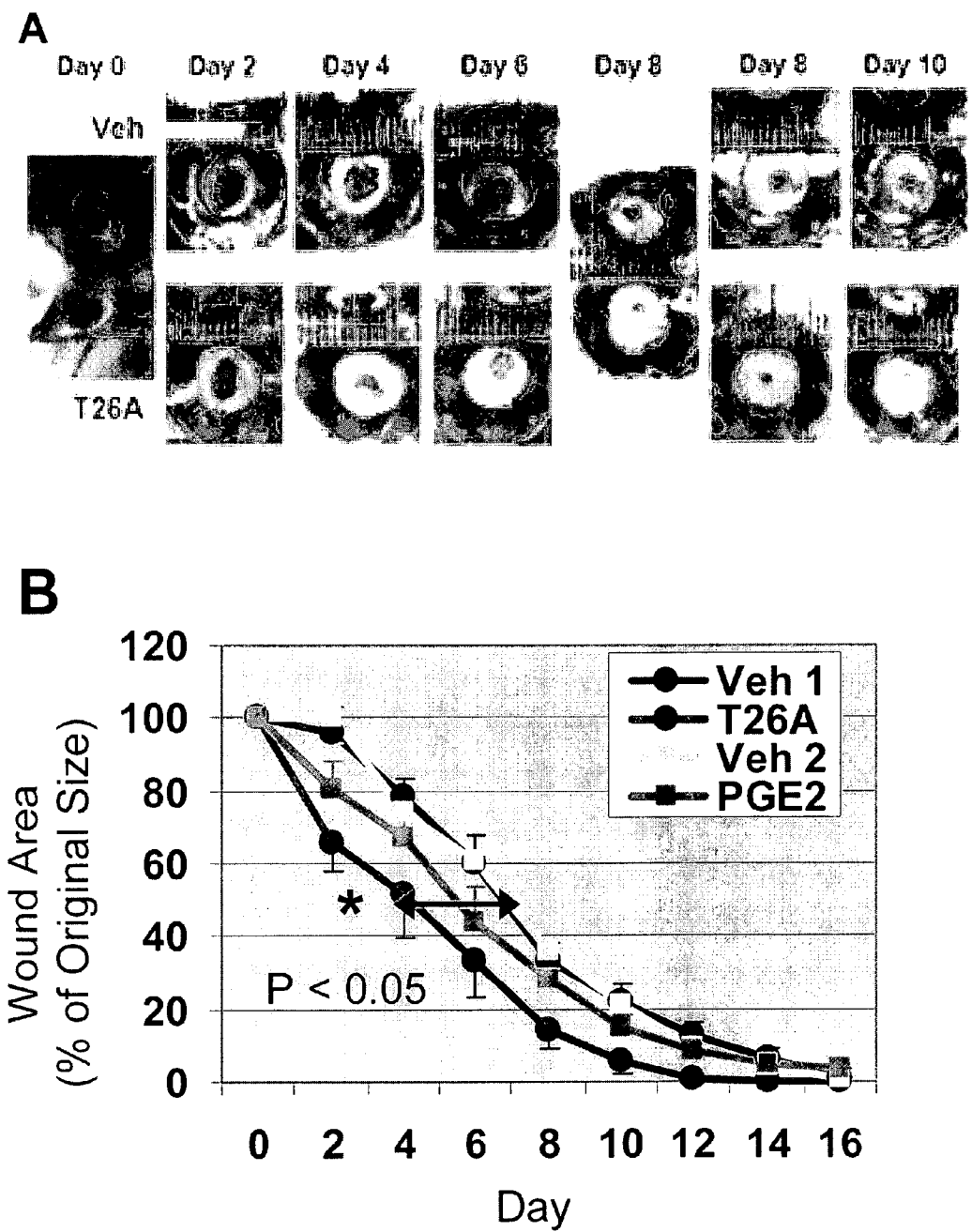
FIG. 1A-1B. Prostaglandin transporter (PGT) inhibitors accelerate wound healing. A. Inhibitor T26A applied directly to the wound accelerates wound healing in mice (bottom row) compared to treatment with vehicle (Veh) (top row). B. Averaged wound areas of 4 mice, each of them had 2 wounds and received topically applied vehicle Veh1 (2% DMSO+2% cremophor in water) on one wound and T26A on the other. On the wounds of a separate group of 4 mice, vehicle Veh2 (2% EtOH) was applied to one wound and 200 μM PGE$_2$ was applied to the other.

The invention provides compounds that inhibit prostaglandin transporter (PGT) activity, where the compounds are represented by the structure:

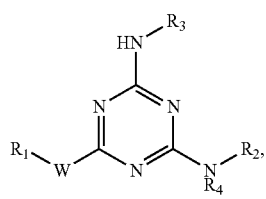
wherein
W is O or NR5;
R1 is H, —CH₃, —(CH₂)₂OH,
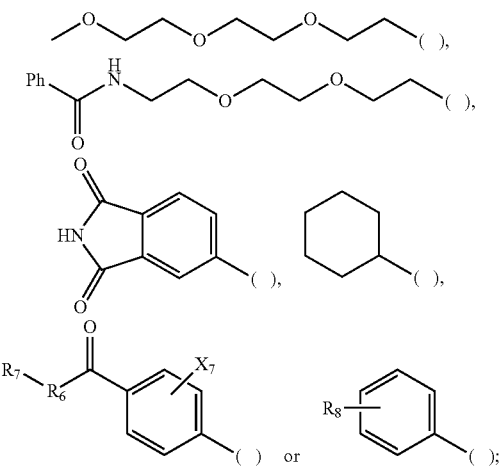
R2 is
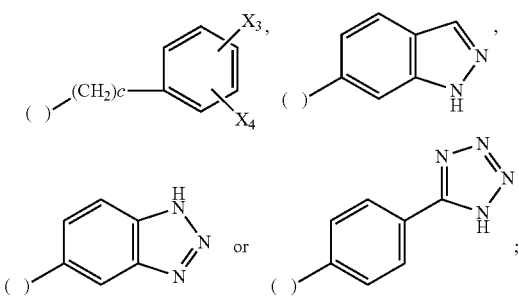
R3 is —(CH₂)₅CH₃, —(CH₂)₆CO₂H, —(CH₂)₆CO₂CH₃, —(CH₂)ₐNHCO-Ph, —(CH₂)₆CONH-Ph, —(CH₂)₆CONHCH₂-Ph,
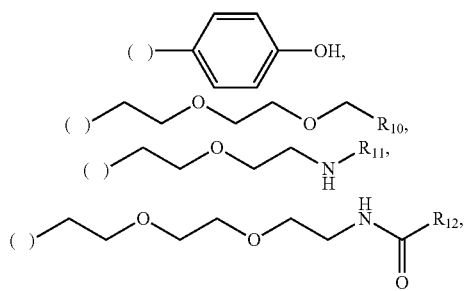
-continued
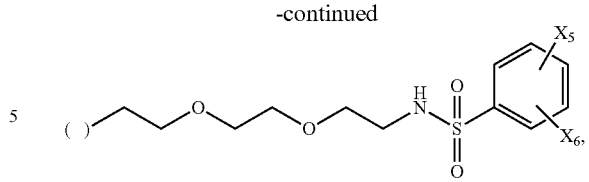
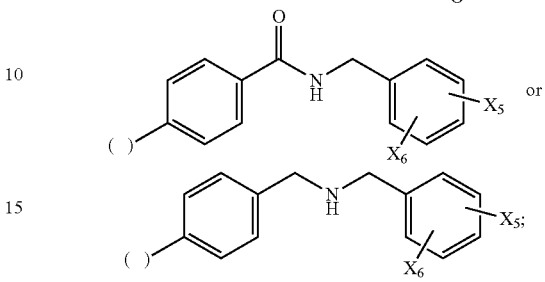
R4 and R5 are independently H or —CH₃;
R6 is O or NR9;
R7 is H, —CH₃, —C(CH₃)₃, —CH₂OH, —(CH₂)₂OH, —(CH₂)₂O(CH₂)₂OH, —(CH₂CH₂O)₃CH₃, —(CH₂CH₂O)₂CH₂CO₂CH₃, —(CH₂)₅CH₃,
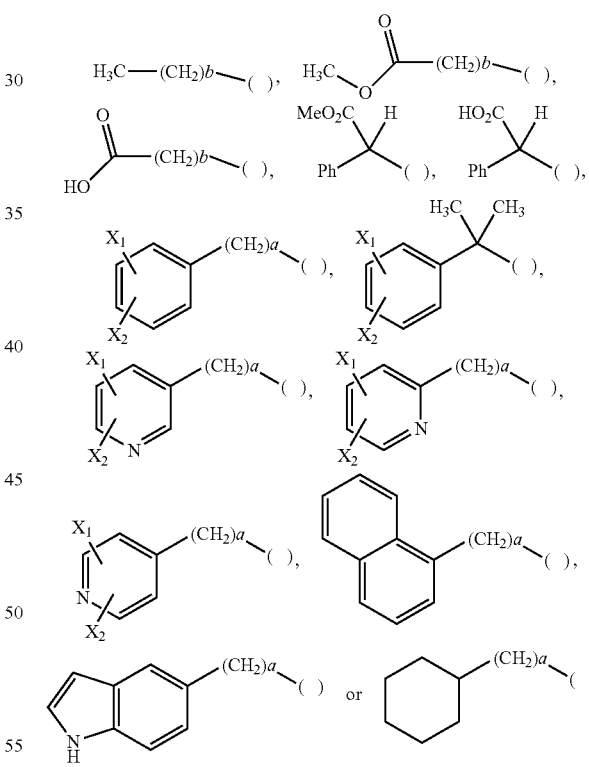
R8 is H, —OH, —CH₂OH, —CO₂H, —CO₂CH₂CH₃, —CO(CH₂)₆CH₃, —OCH₃, —NH₂, —SO₂NH₂, —CONH-Bn or
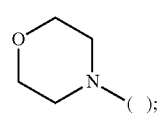

R9 is H or —CH₃;
R10 is —CH₂NH₂, —CO₂H or —CO₂CH₃;
R11 is —SO₂-Ph, —CH₂-Ph, —CONN-Ph, —COCH₃,

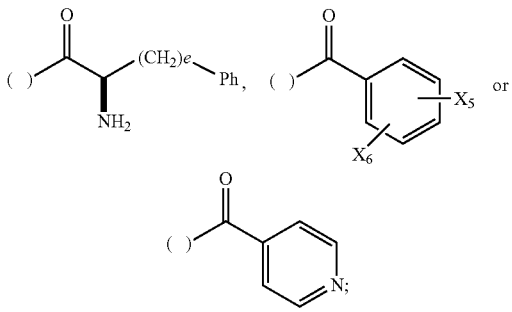

and
R12 is —CH₃,

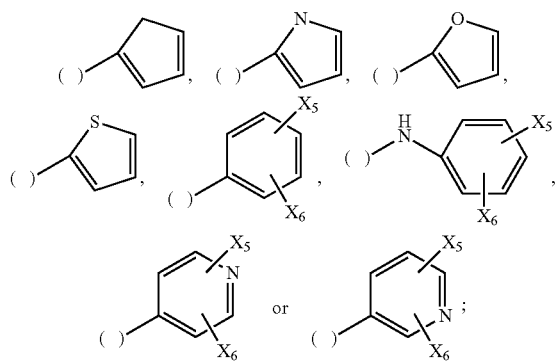

where X1, X2, X3, X4, X5, X6 and X7 are independently H, halogen, —OH, —CH₃, —CF₃, —OCH₃, —CO₂H, —CO₂CH₃, —CH₂CO₂H, —CH₂CO₂CH₃, phenyl or —O-Bn; and where a=0-2; b=1-6; c=0-1; d=4-7; and e=0-1; or a pharmaceutically acceptable salt thereof.

As used herein in chemical structures, "Ph" stands for phenyl, "Bn" stands for benzyl (—CH₂Ph), "Bz" stands for benzoyl (—(C=O)Ph), and "Me" stands for methyl (—CH₃). The point of attachment of the side group substitution to the main part of the compound is indicated by "( )" The terms ortho, meta and para refer to the positions of substitutions in relation to the main part of the compound.

In preferred compounds, W is NR5. In preferred compounds, R6 is NR9.

In preferred compounds, at least one of R4, R5 and R9 is H, or all of R4, R5 and R9 are H. Preferably, at least R5 (out of R4, R5 and R9) is H.

In preferred compounds, one of X1 and X2 is H, and the other is halogen, —CF₃, —CH₃, —CO₂H, —CO₂CH₃, —OCH₃ or phenyl; or both X1 and X2 are halogen. In preferred compounds, one of X3 and X4 is H, and the other is halogen, —CO₂H, —CO₂CH₃, —CH₂CO₂H, —CH₂CO₂CH₃, —OH, —OCH₃ or —O-Bn; or one of X3 and X4 is —OH, and the other is halogen, —CO₂H or —CO₂CH₃. In preferred compounds, one of X5 and X6 is H, and the other is halogen, —CF₃, —OCH₃ or phenyl; or both X5 and X6 are halogen. In preferred compounds, X7 is H, —CF₃ or —OCH₃.

In preferred compounds, R8 is located in para position. In preferred compounds, one or both of X1 and X2 are located in ortho position, or one or both of X1 and X2 are located in meta position, or X1 is located in meta position and X2 is located in para position, or X1 is located in ortho position and X2 is located in para position. In preferred compounds, X3 is in meta position and X4 is in para position. In preferred compounds, X5 or X6 is in meta position, or X5 or X6 is in para position.

Preferred compounds have the structure:

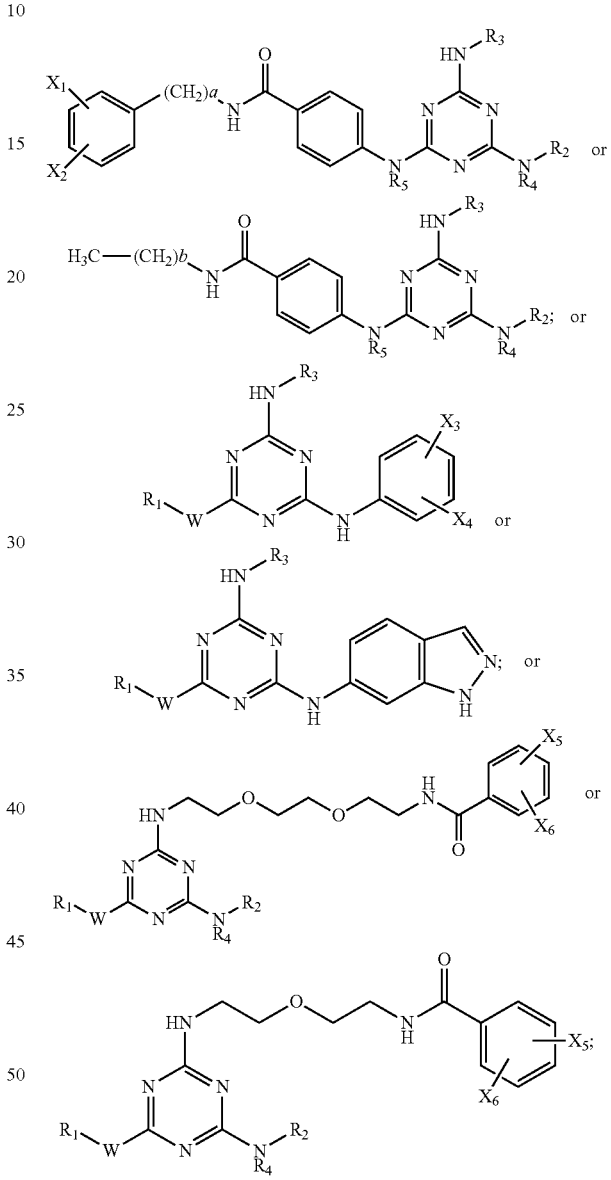

or a pharmaceutically acceptable salt thereof.
In preferred compounds,
R1 is

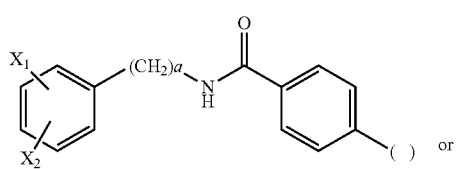

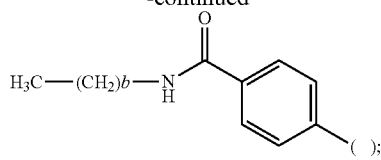

R2 is

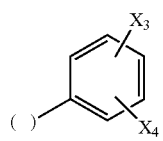 or 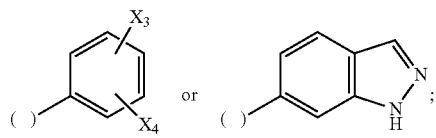

and

R3 is

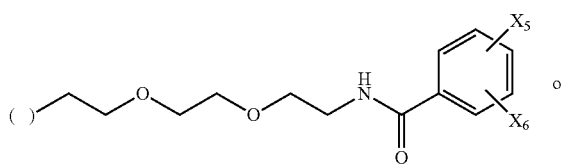

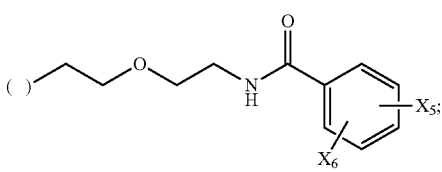

where X1, X2, X3, X4, X5 and X6 are independently H, halogen, —OH, —CH₃, —CF₃, —OCH₃, —CO₂H, —CO₂CH₃, —CH₂CO₂H or —CH₂CO₂CH₃; and where a=1-2; and b=1-5; or a pharmaceutically acceptable salt thereof.

In preferred compounds,

R1 is

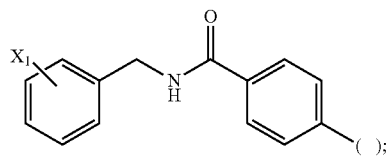

R2 is

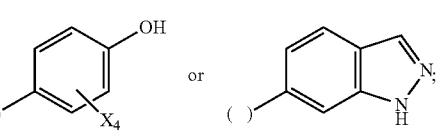

and

R3 is

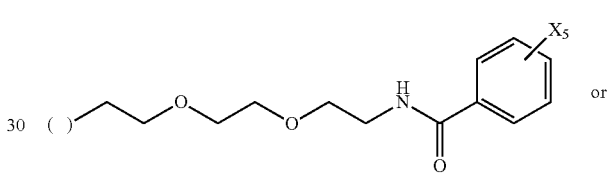

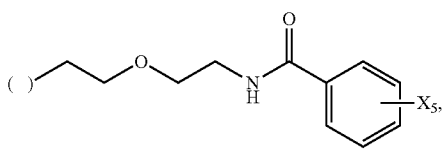

where X1 is H or halogen; where X4 is H, halogen or —CO₂H; and where X5 is H, halogen or —OCH₃; or a pharmaceutically acceptable salt thereof.

Preferred compounds have the structure:

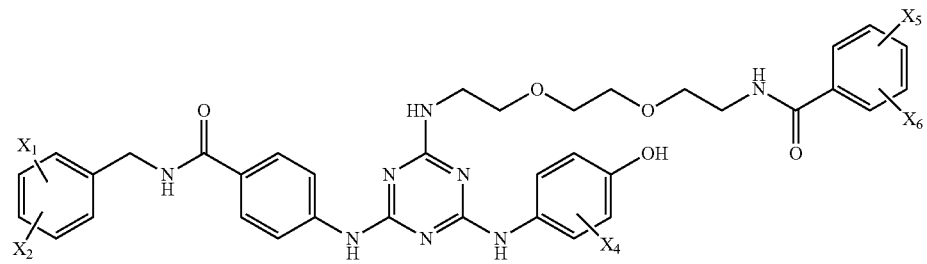

or a pharmaceutically acceptable salt thereof.

In the compounds described herein, W—R1 can be replaced with halogen.

Halogens are F, Cl, Br, I and At. Preferred halogens are Br, Cl and F.

The invention provides a compound having the structure:
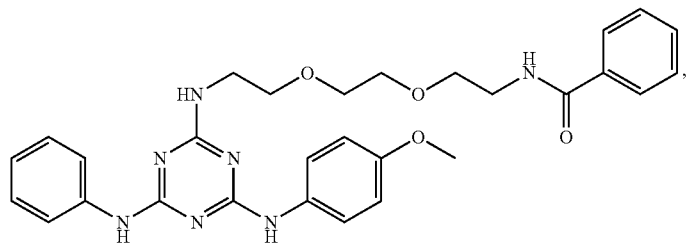,
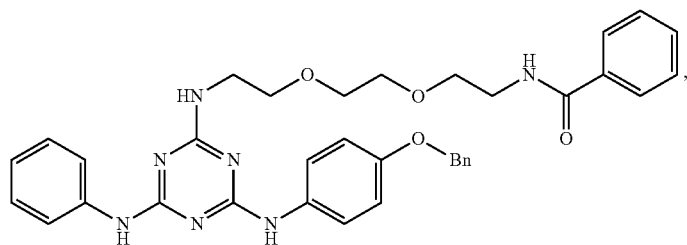,
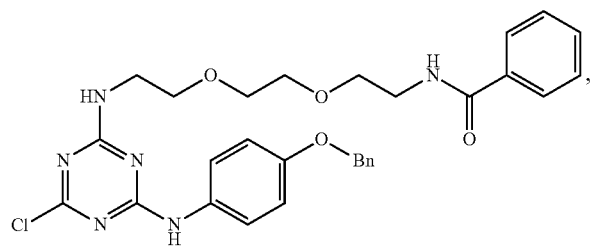,
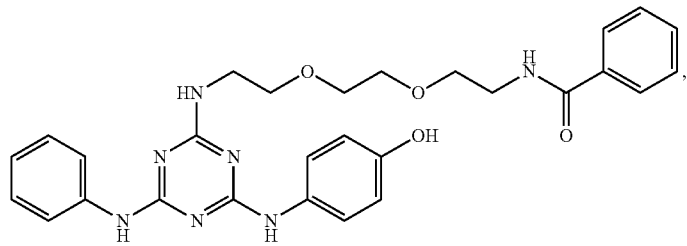,
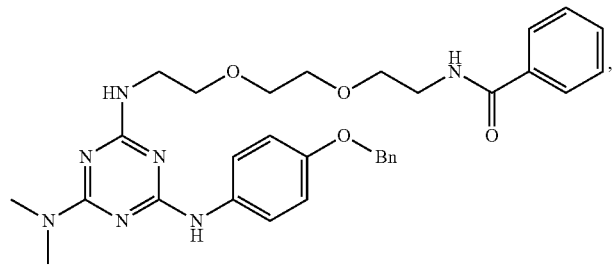,
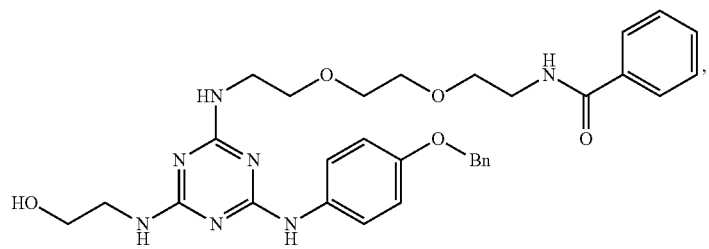,

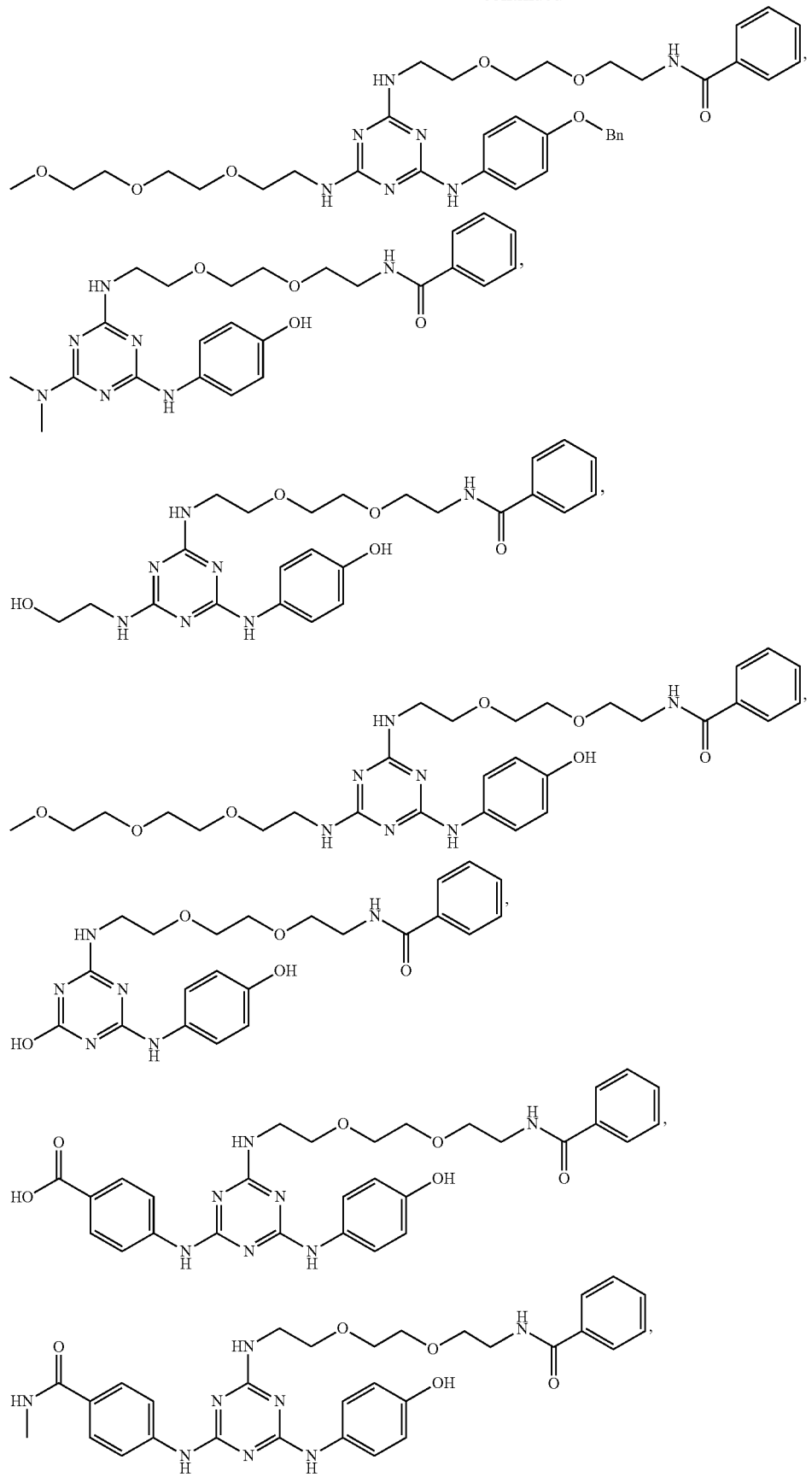

-continued
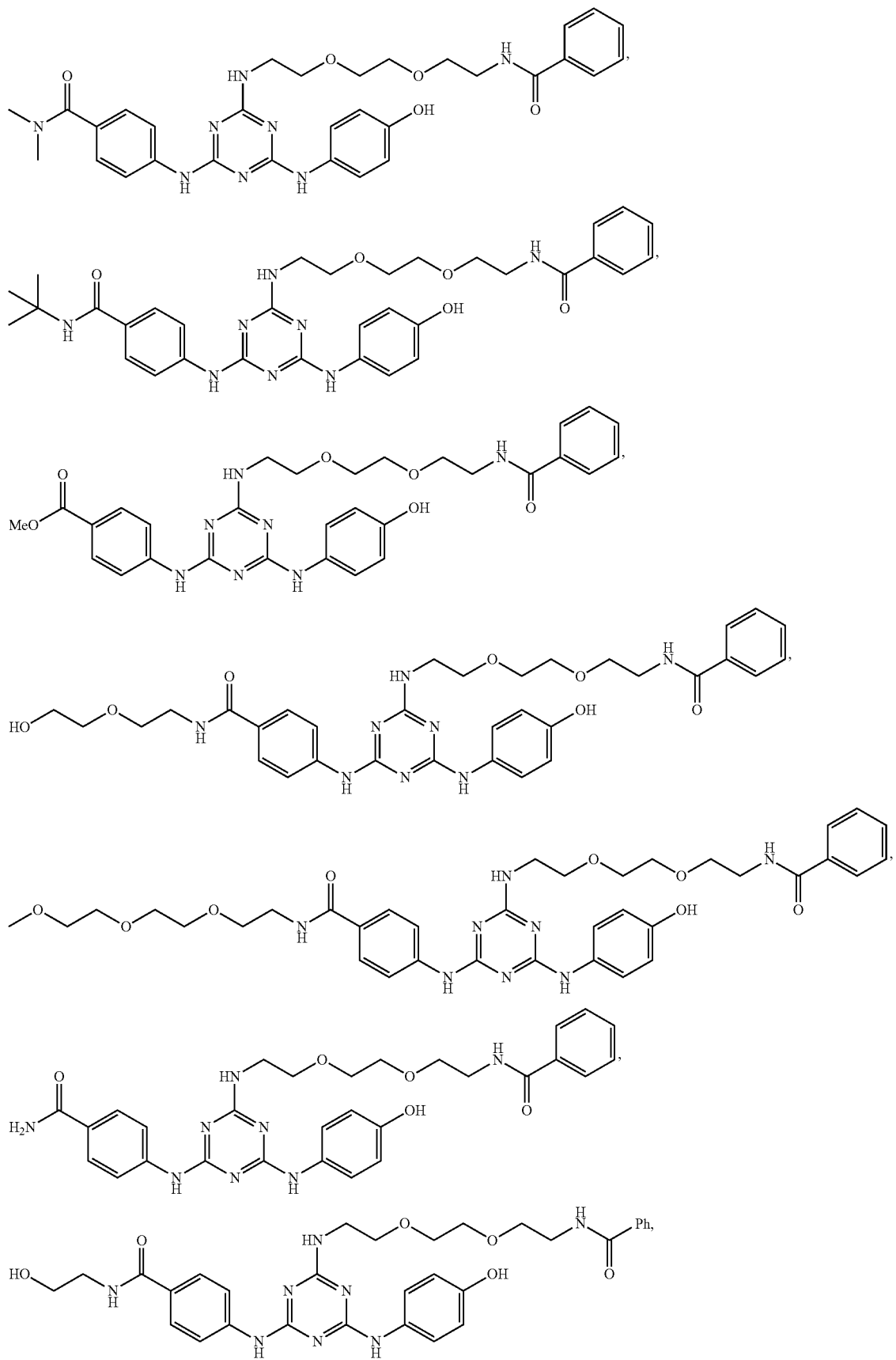

-continued
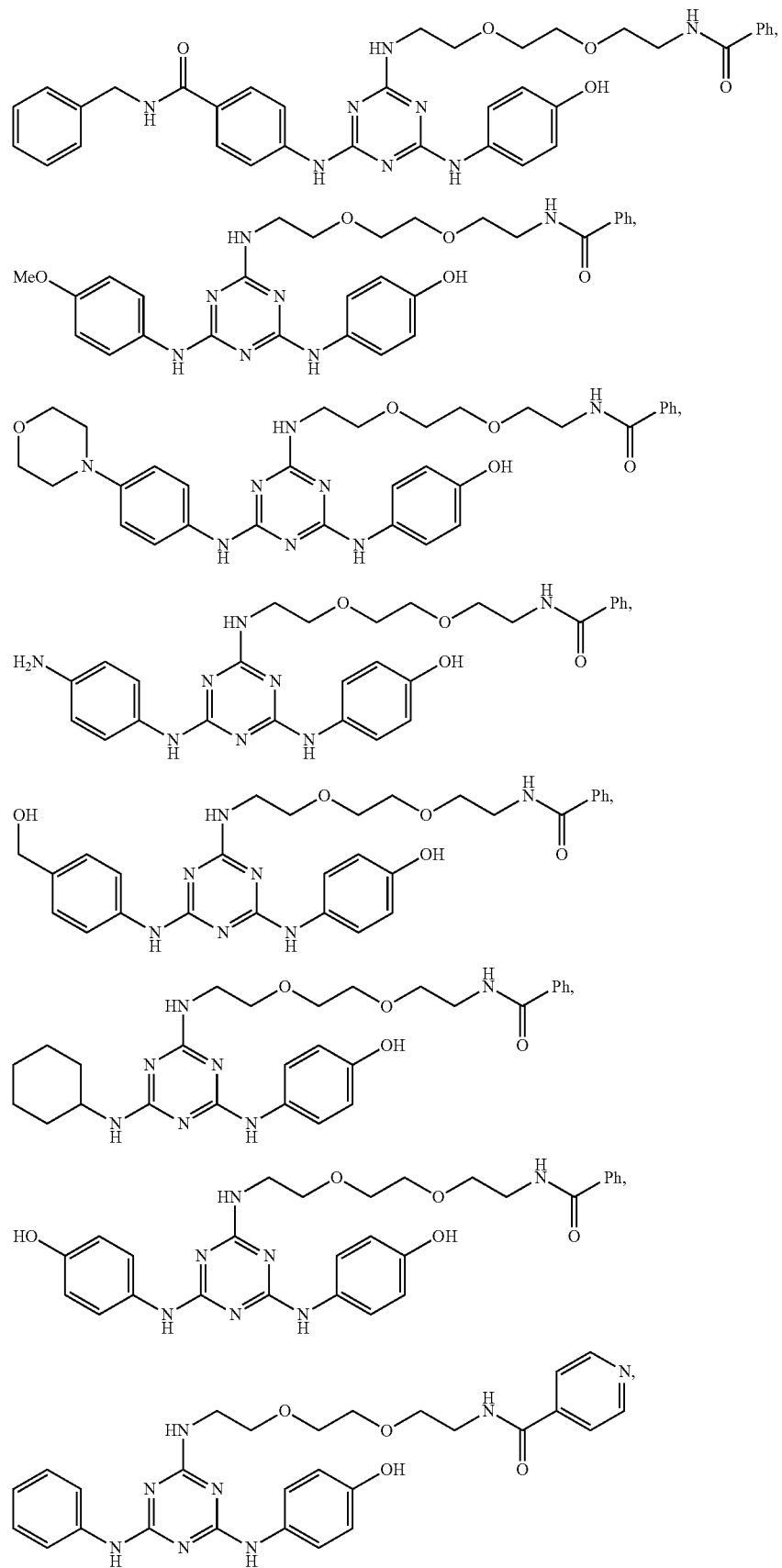

-continued
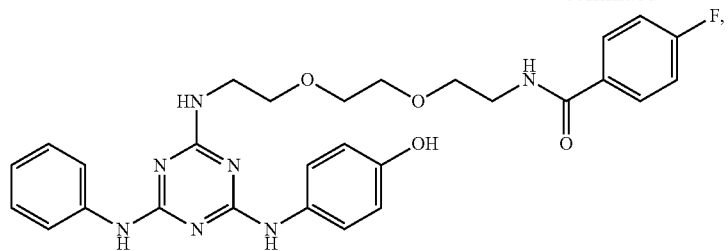
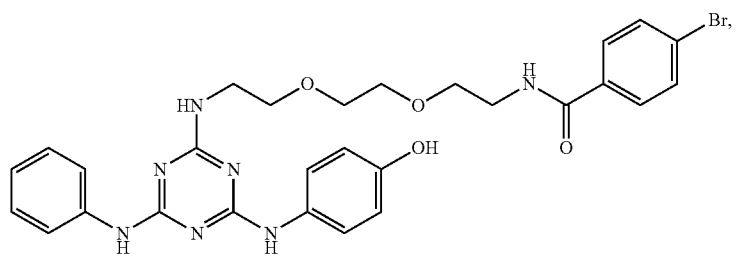
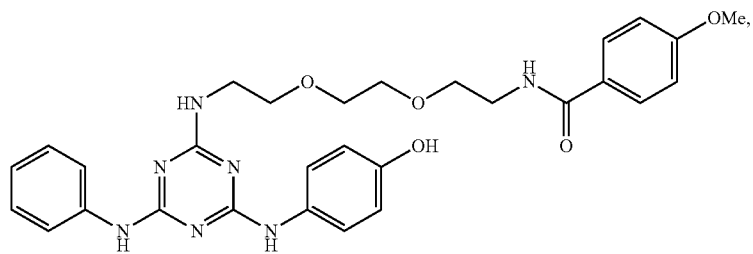
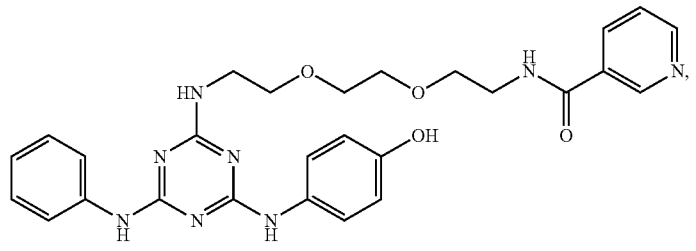
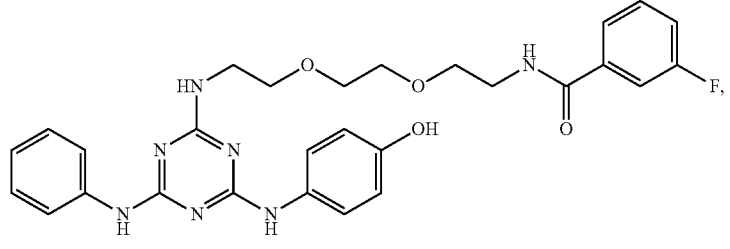
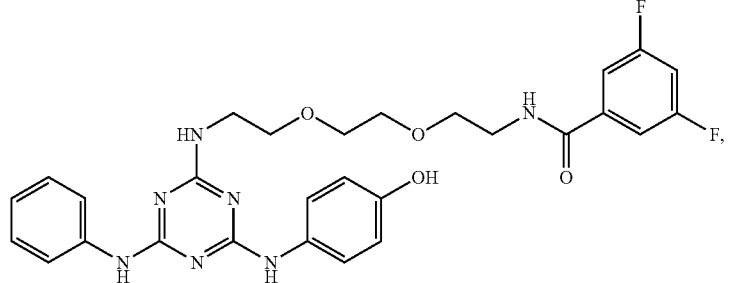

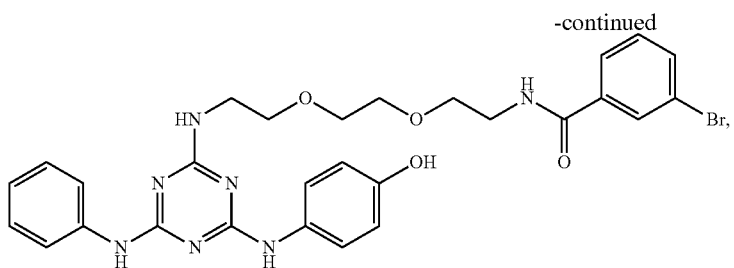
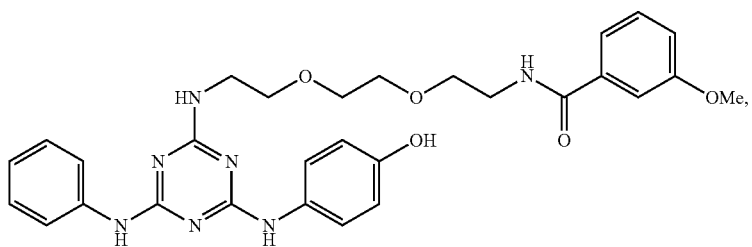
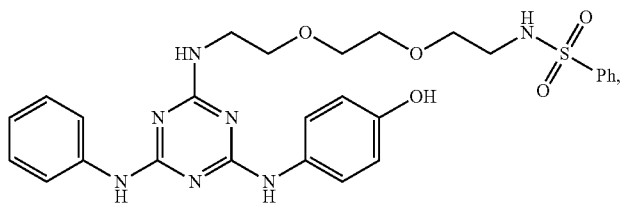
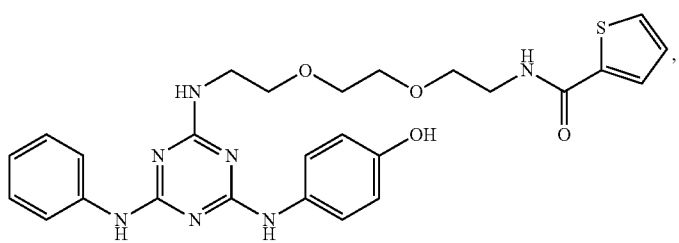
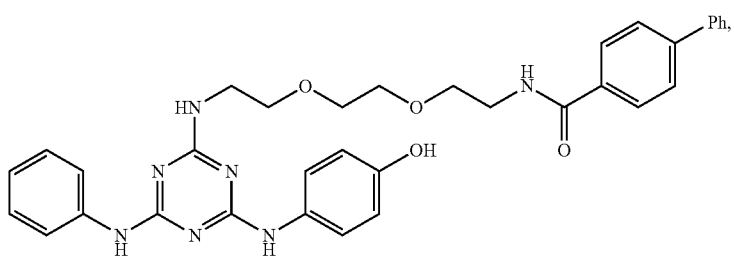
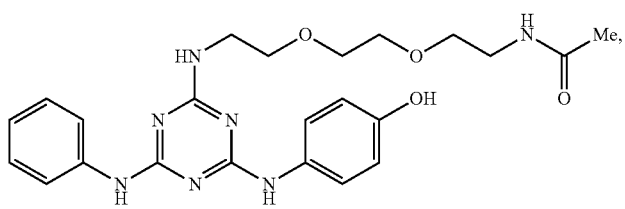
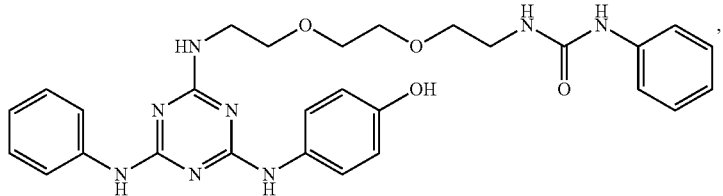

-continued
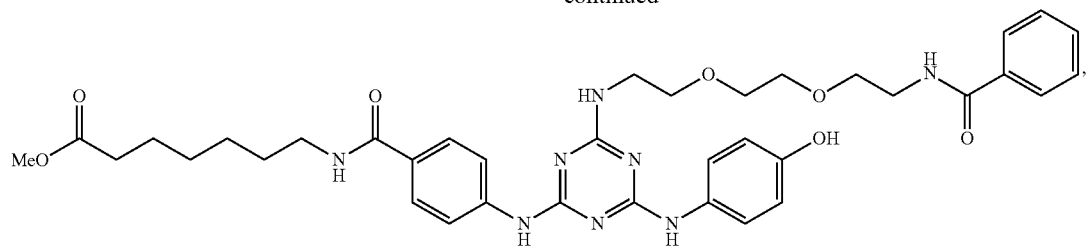
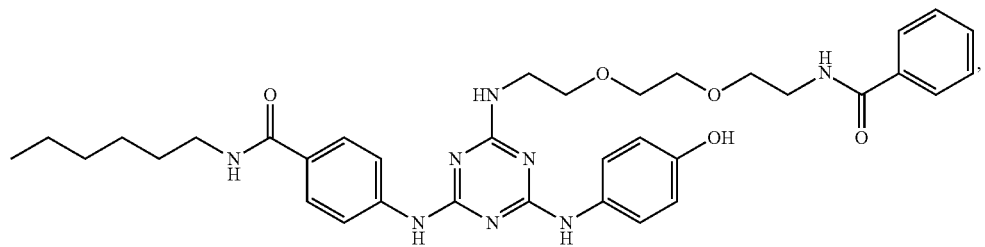
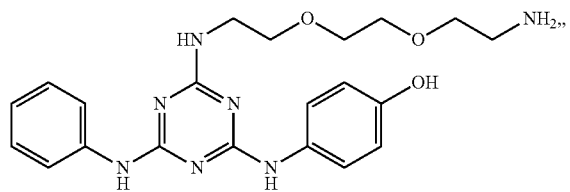
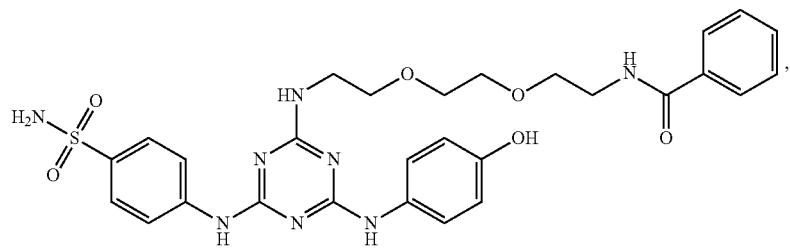
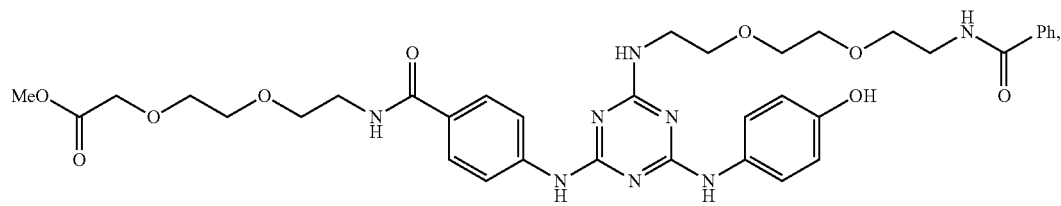
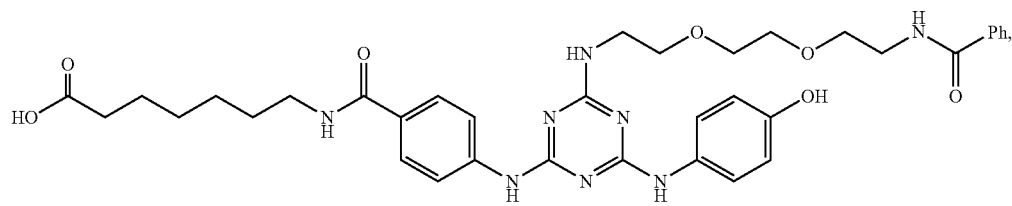
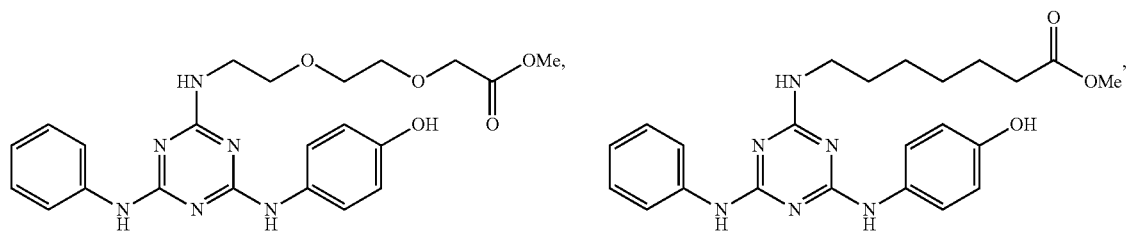

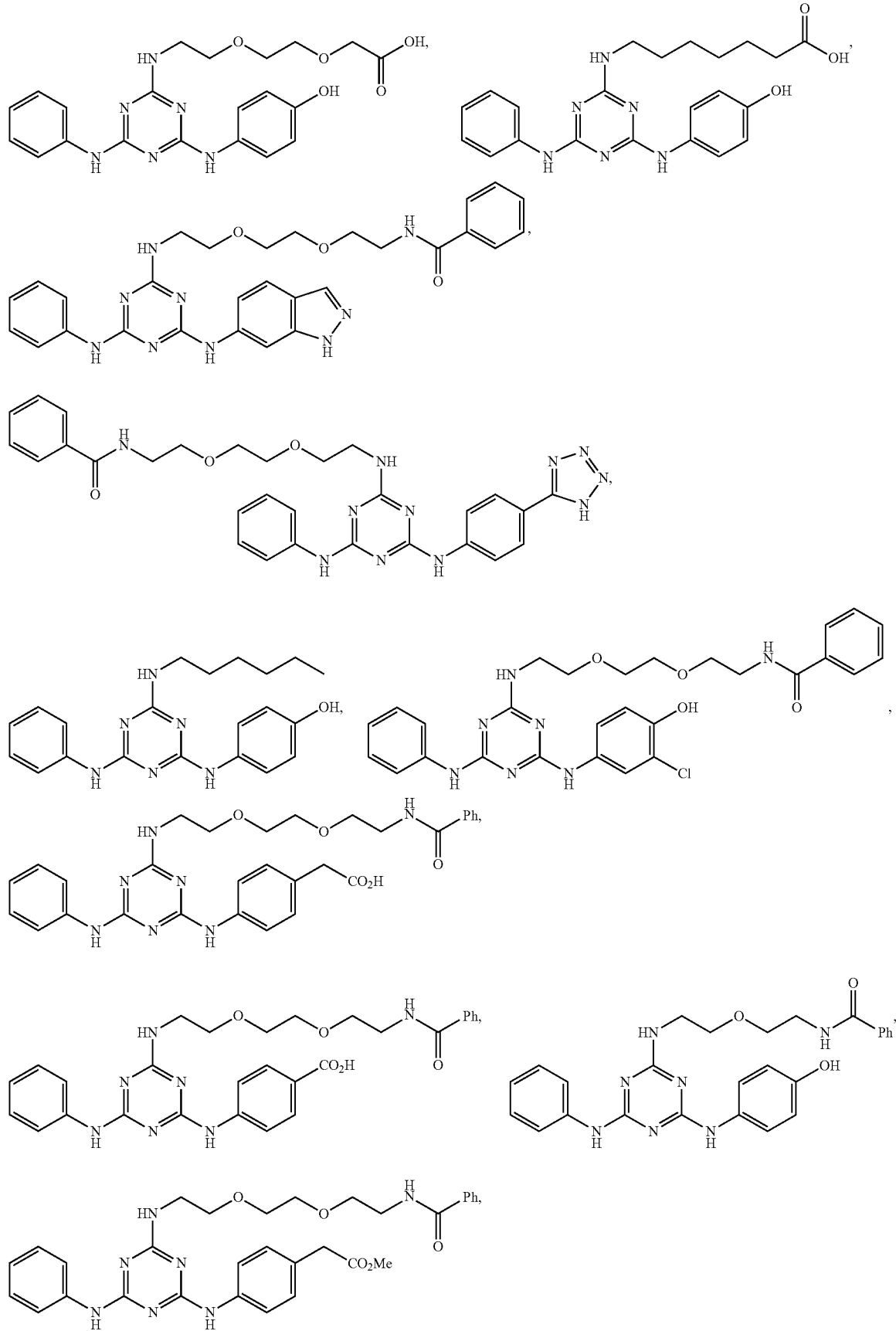

25 26
-continued
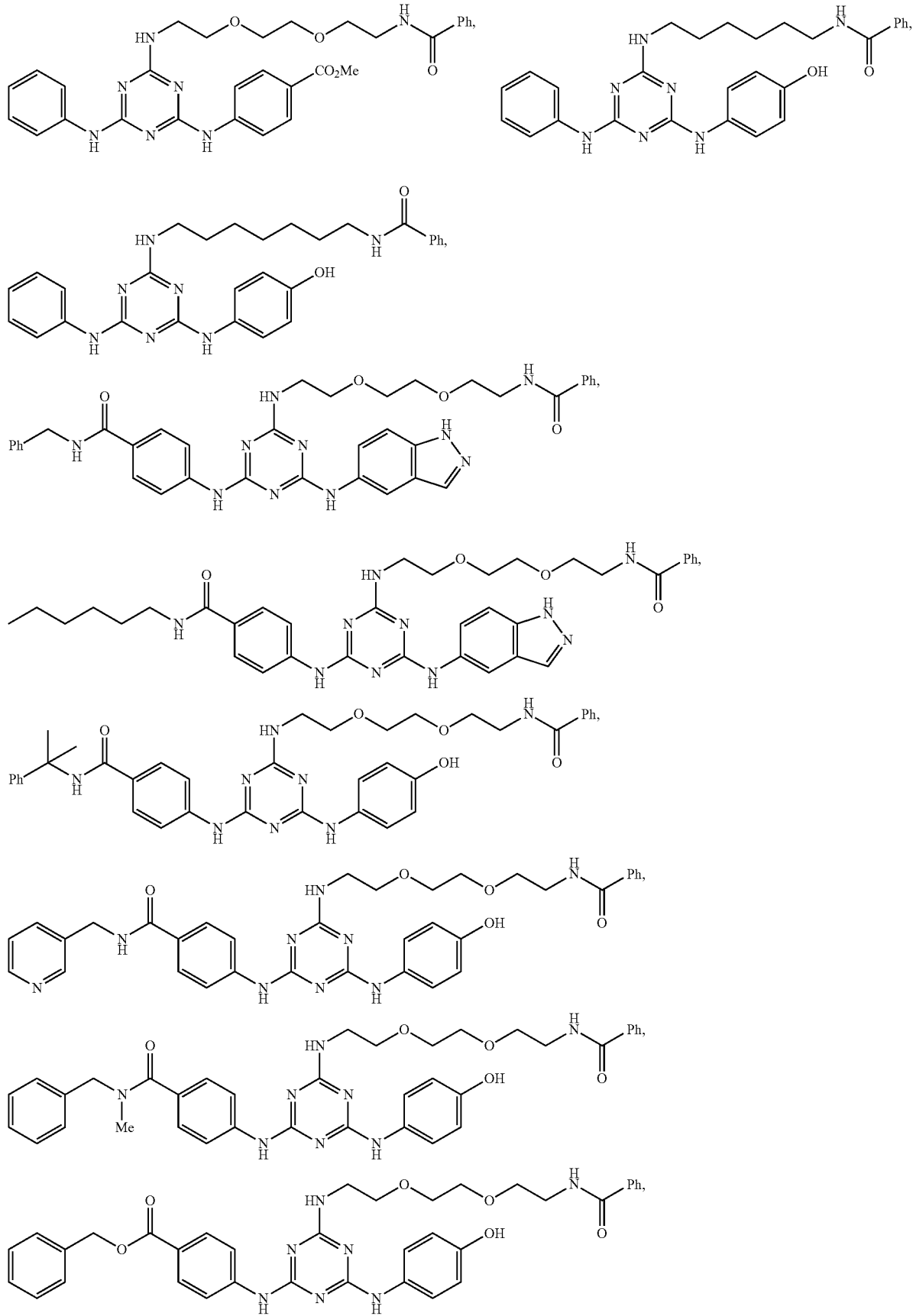

-continued
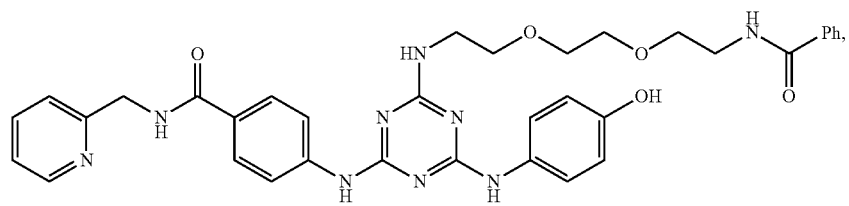
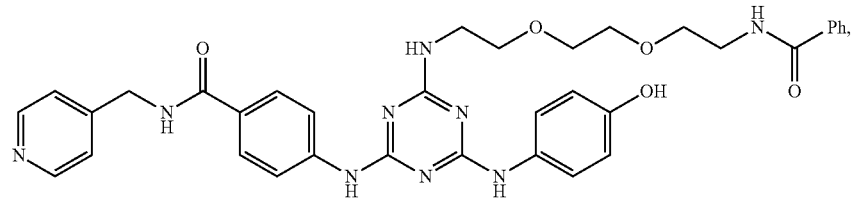
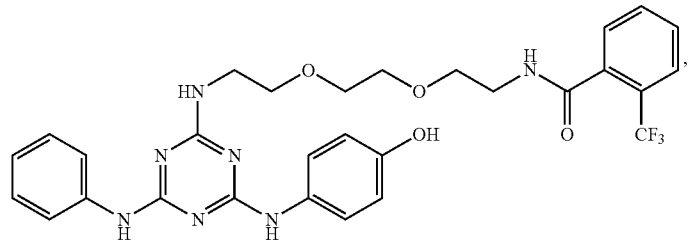
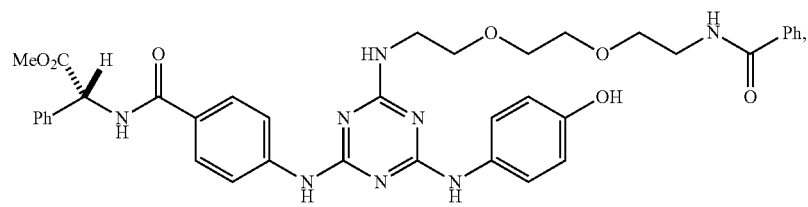
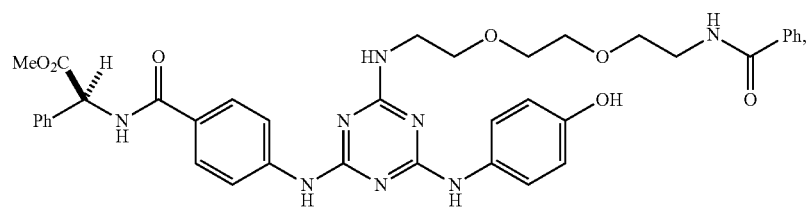
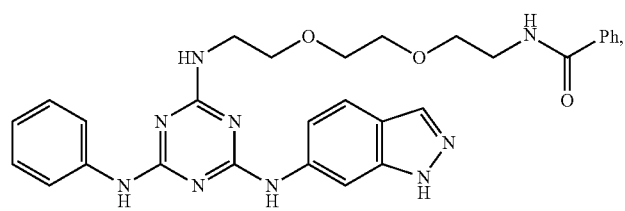
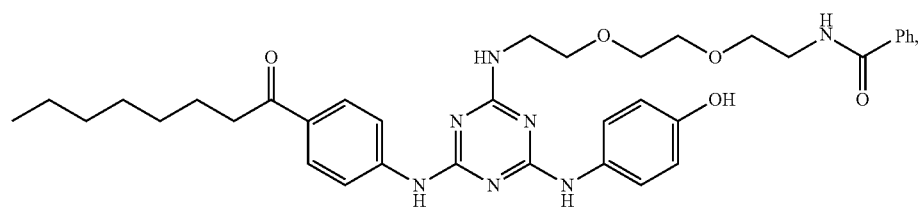
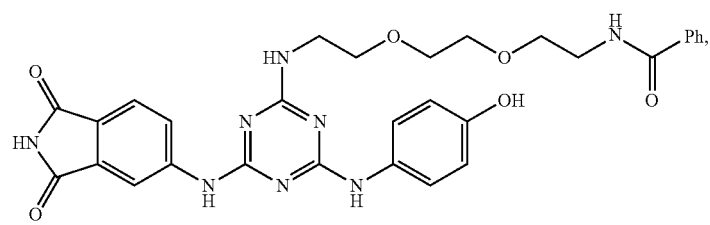

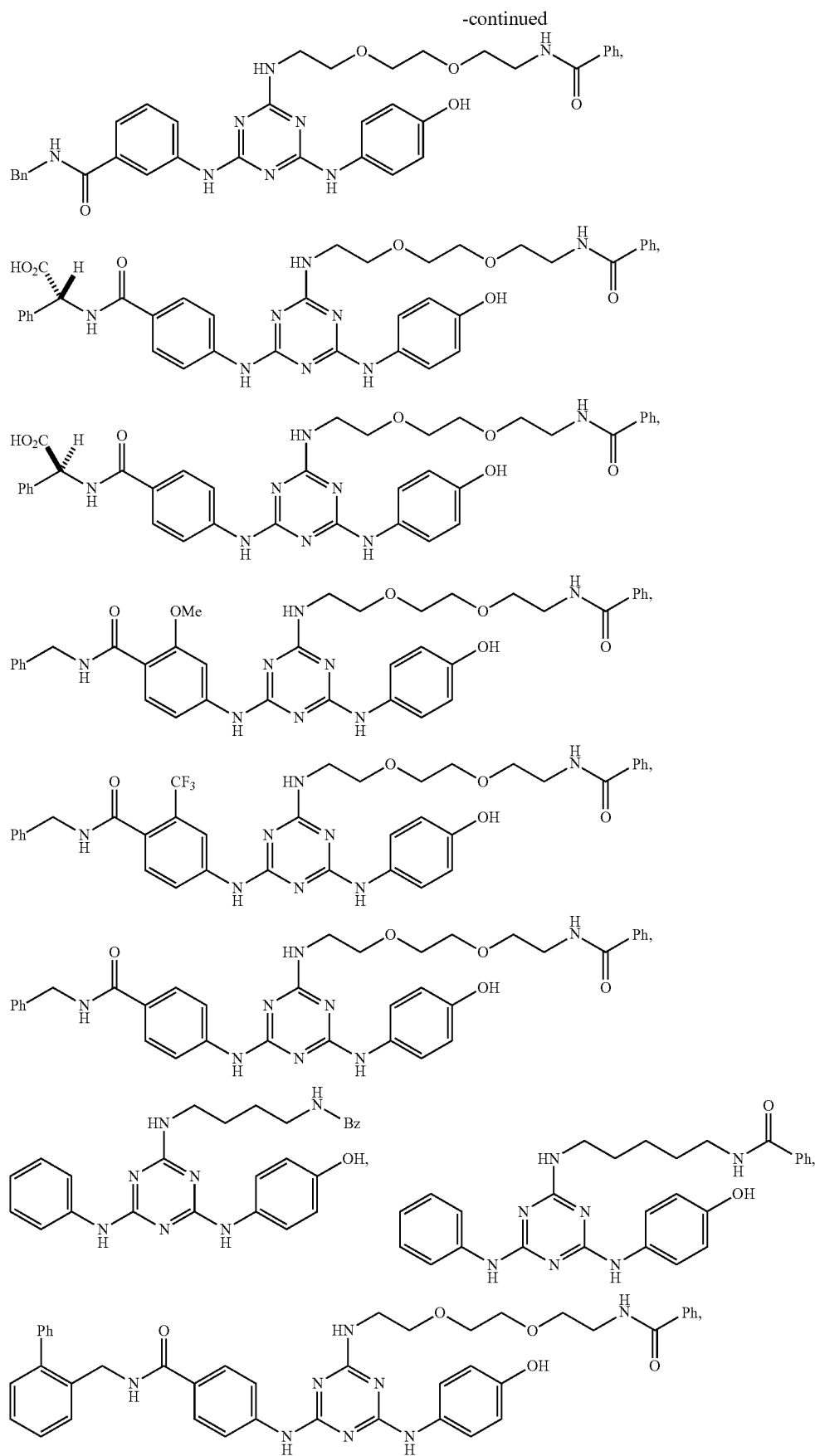

-continued
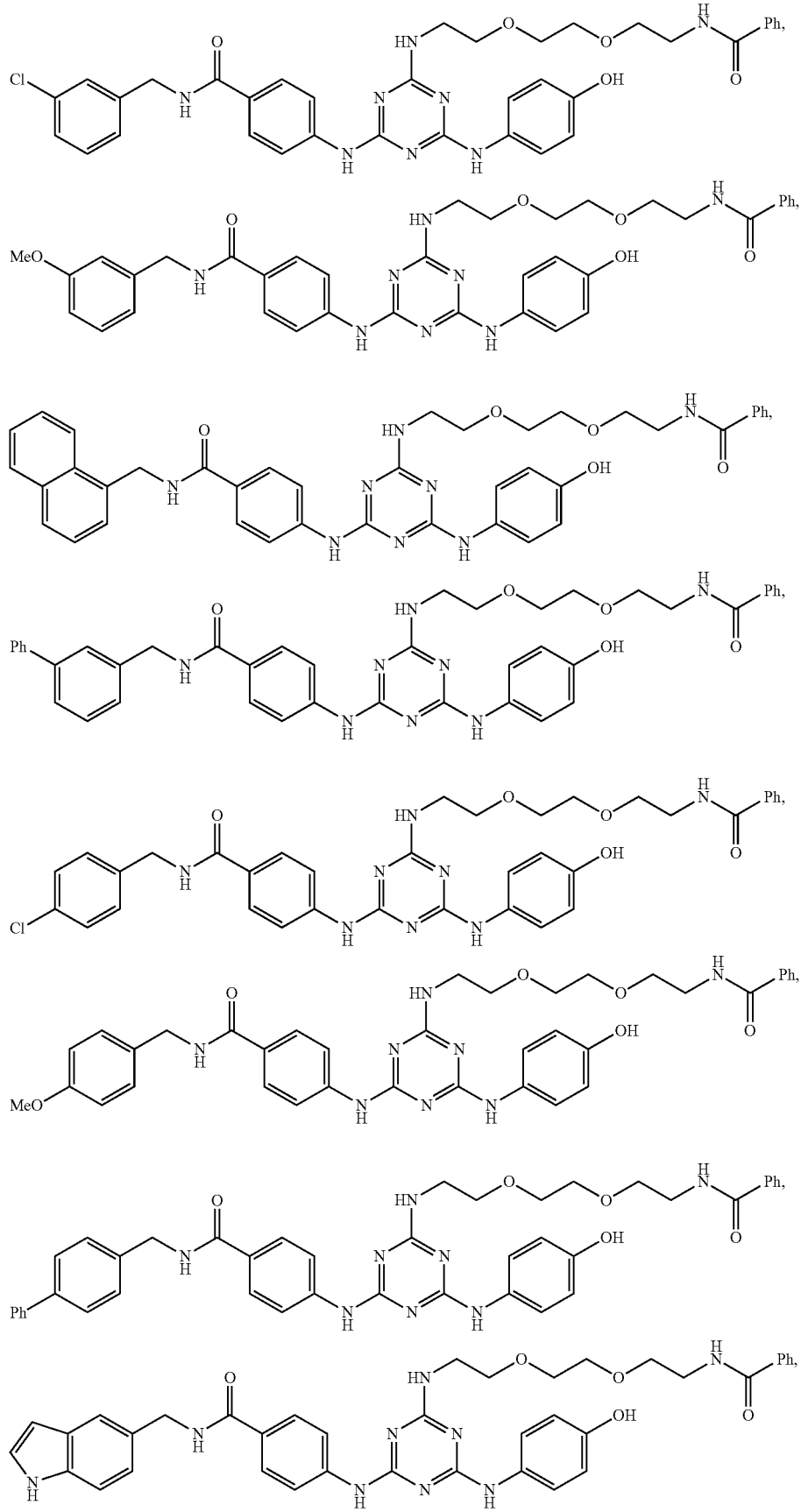

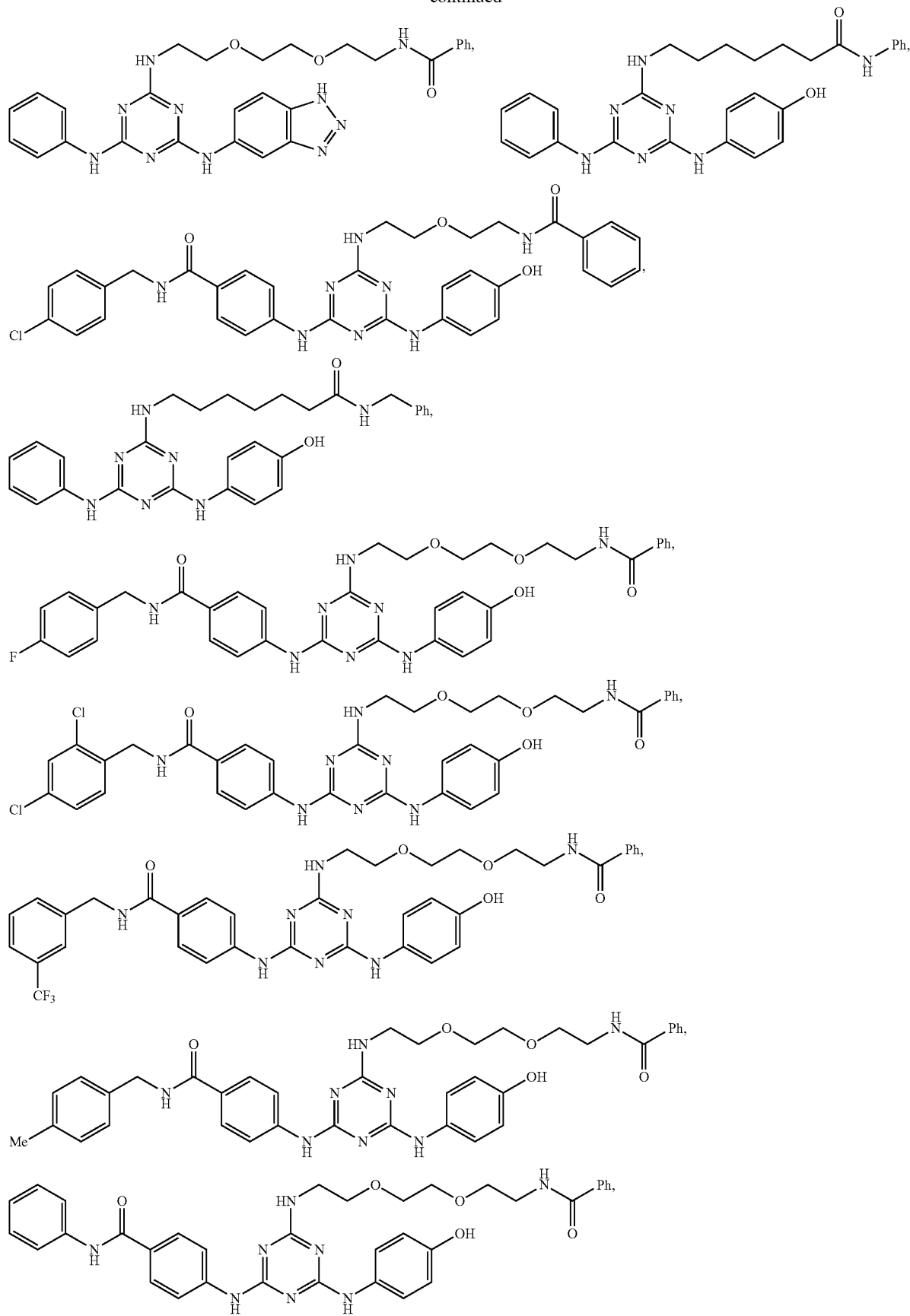

-continued
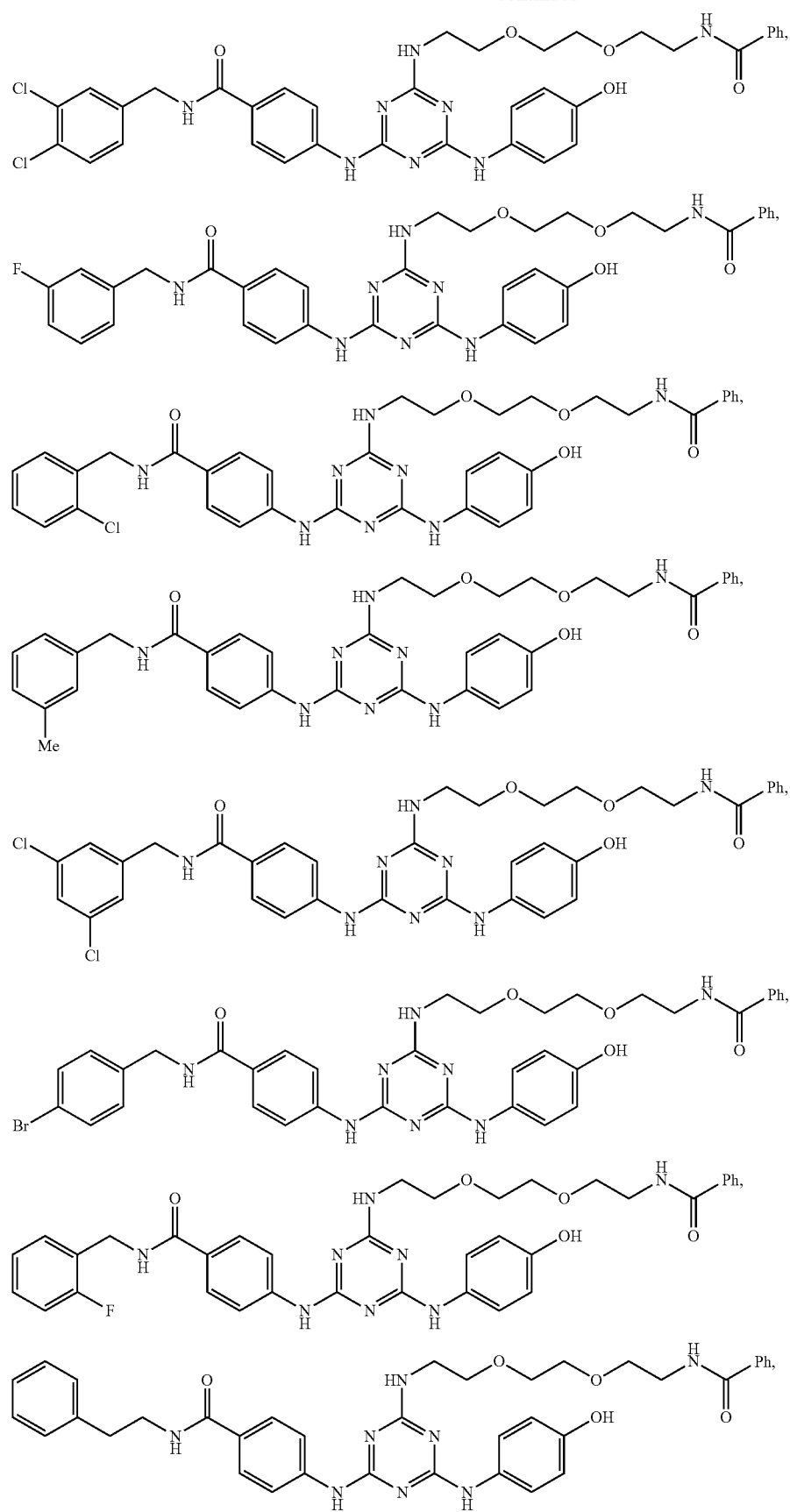

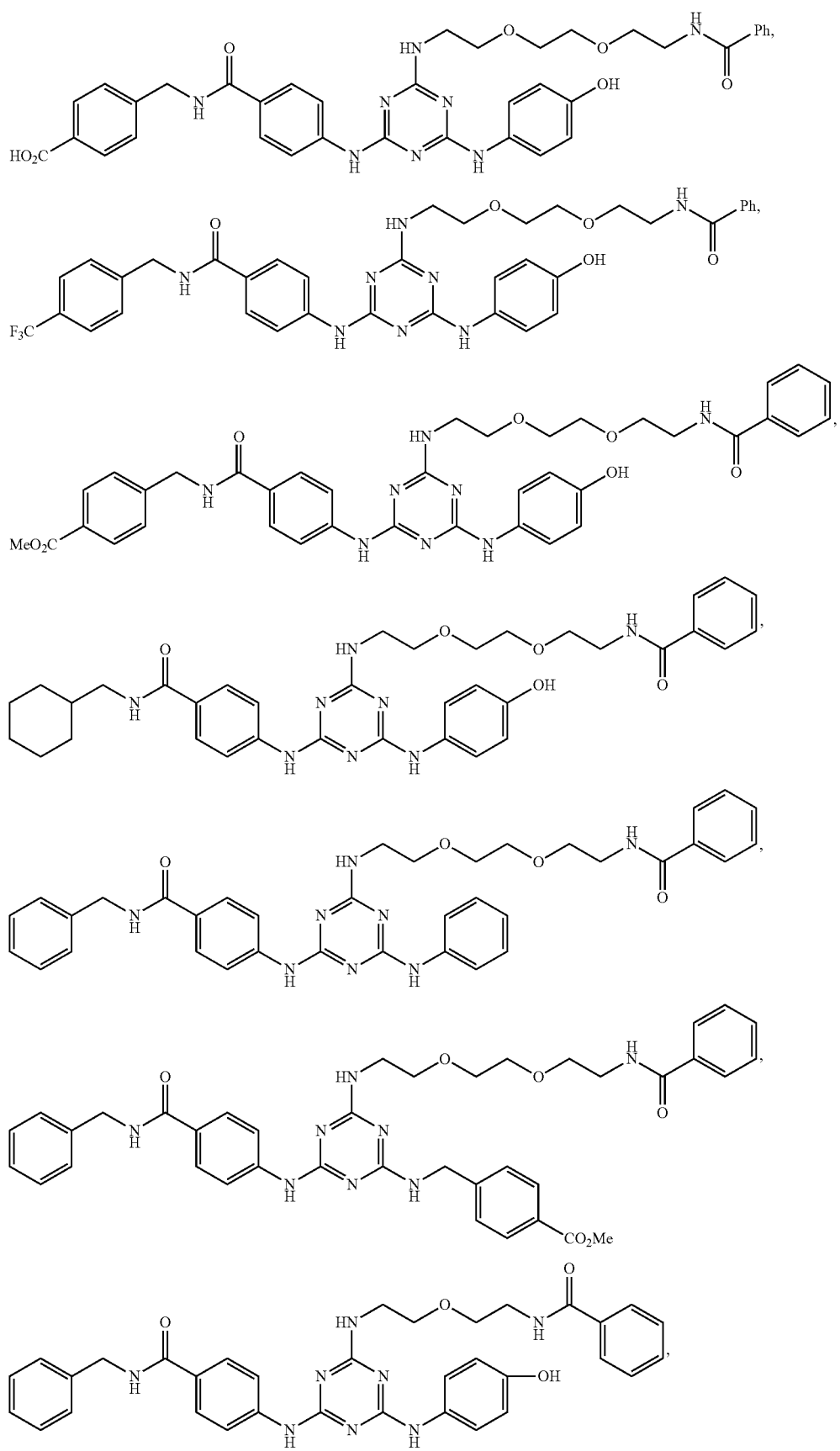

-continued
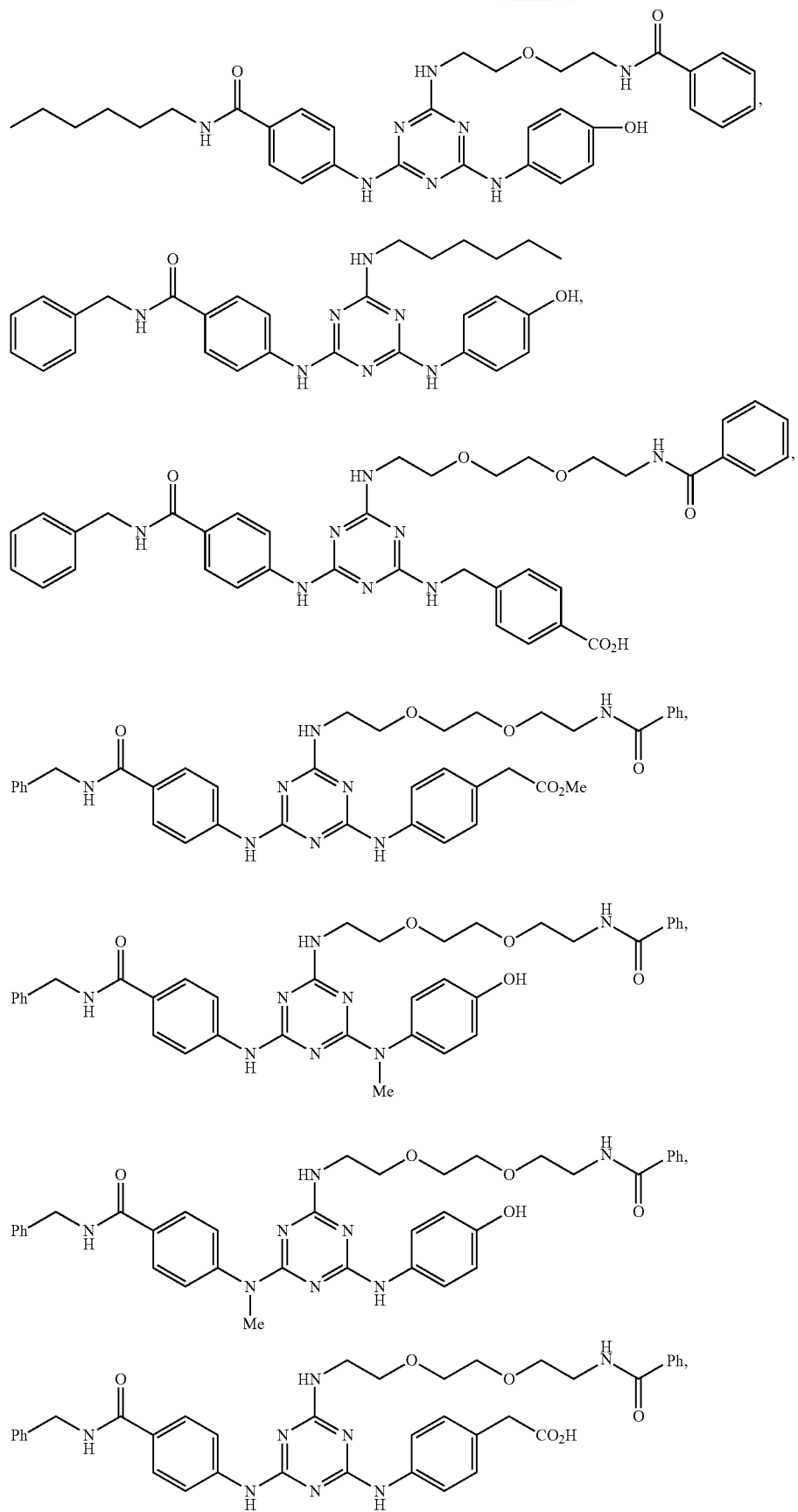

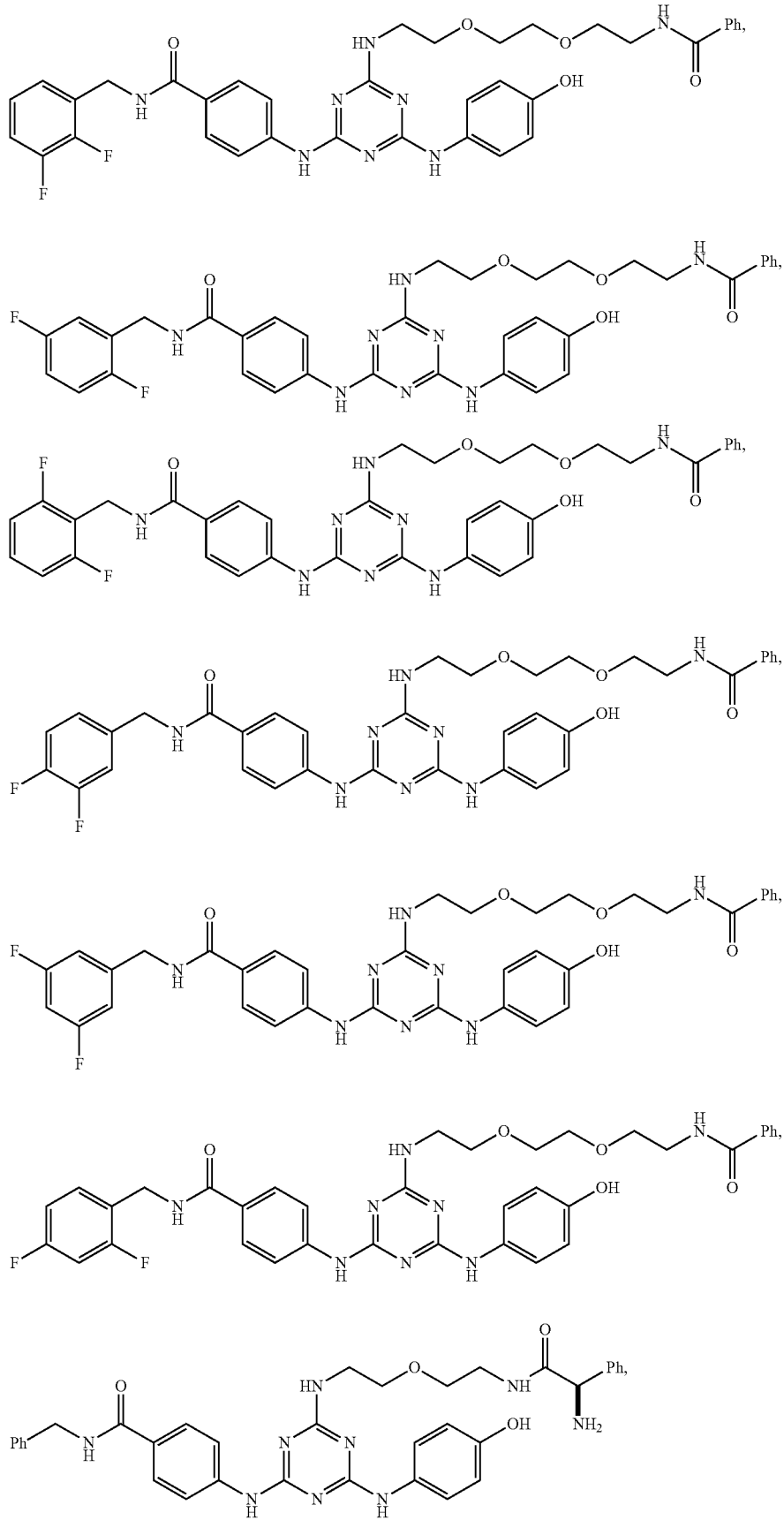

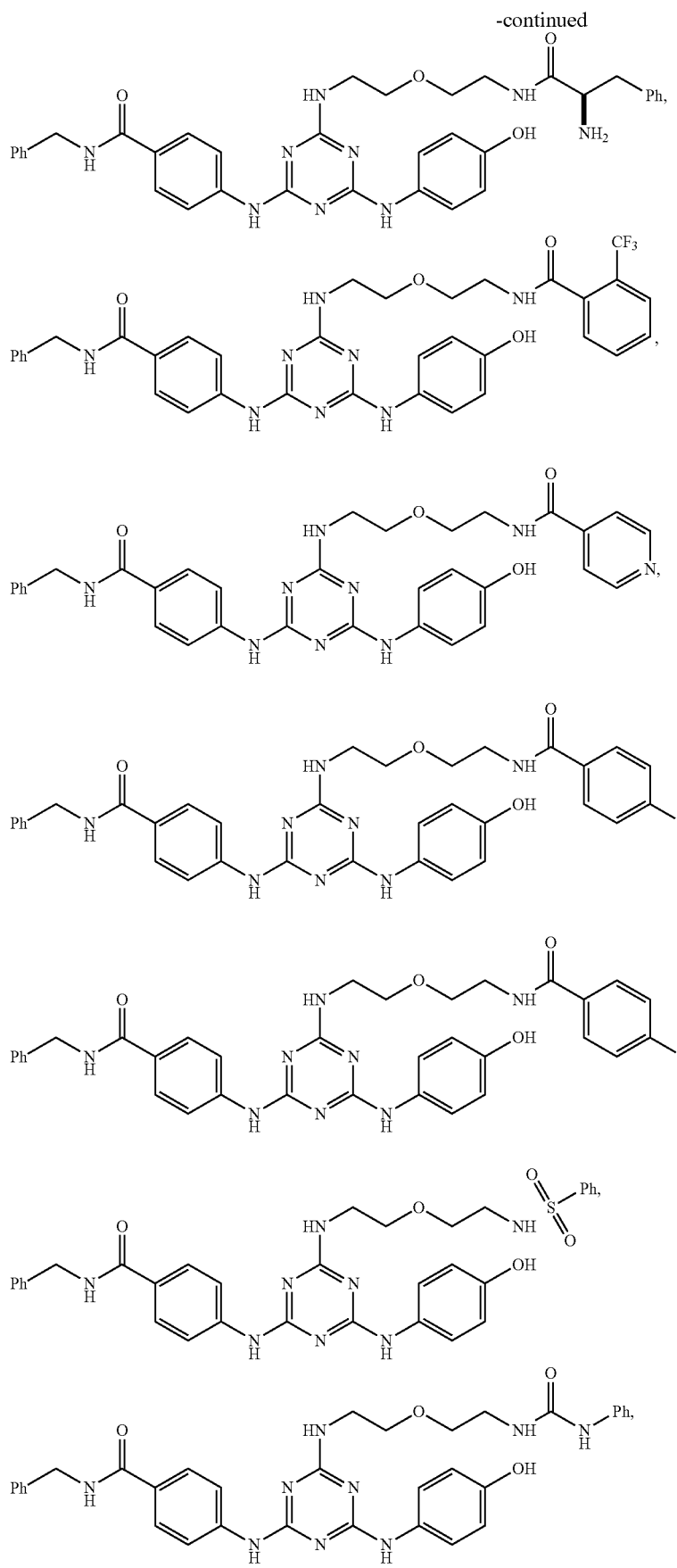

-continued
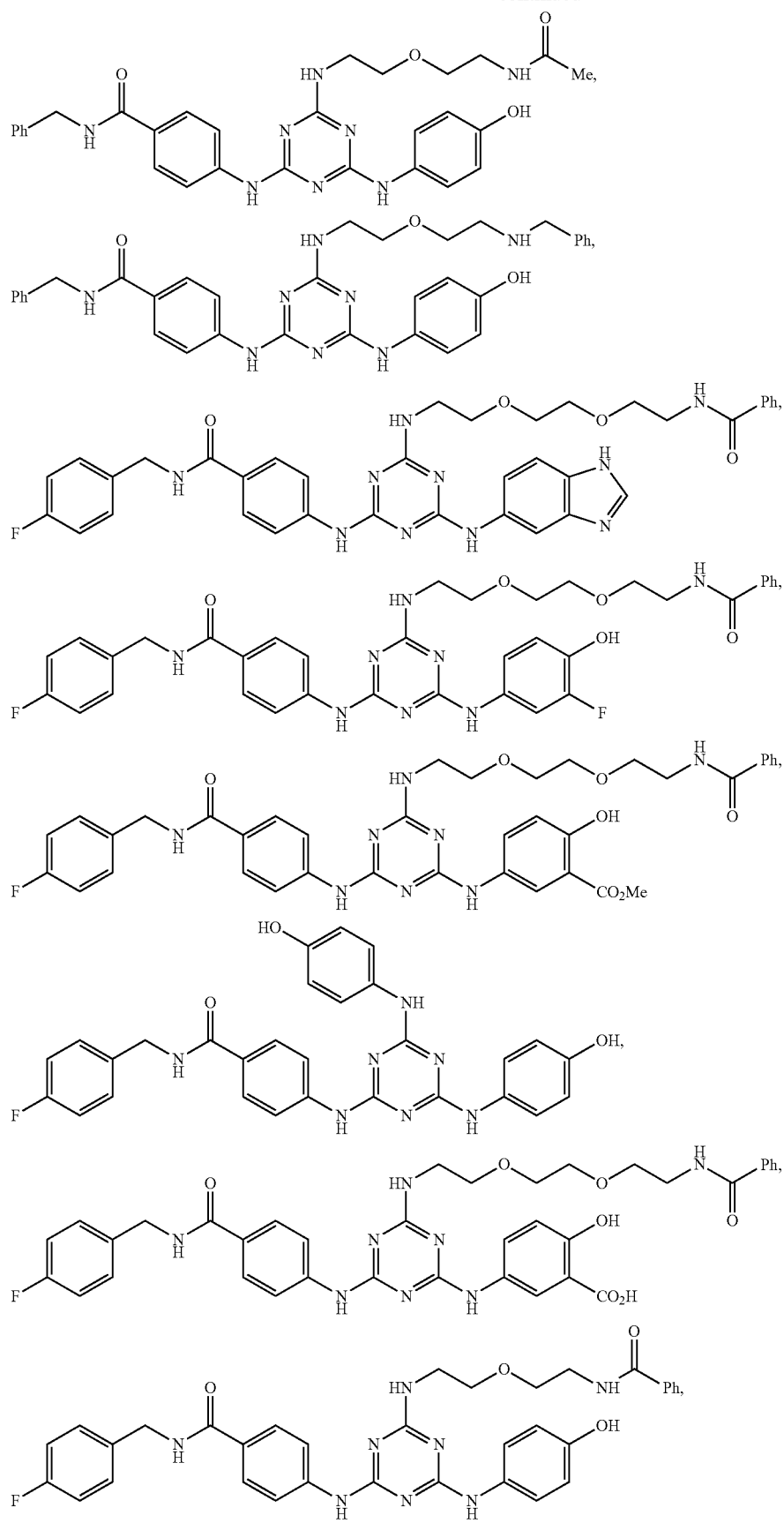

-continued
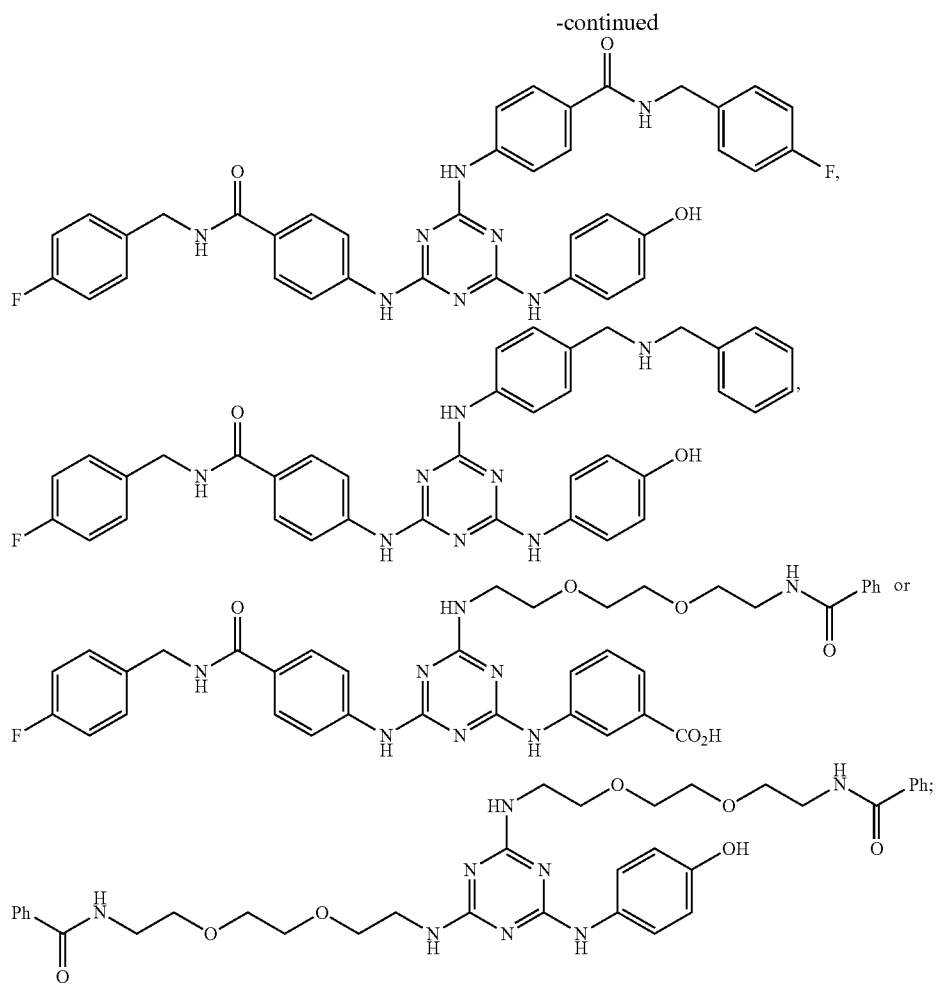
or a pharmaceutically acceptable salt thereof.
Preferred compounds have the structure:
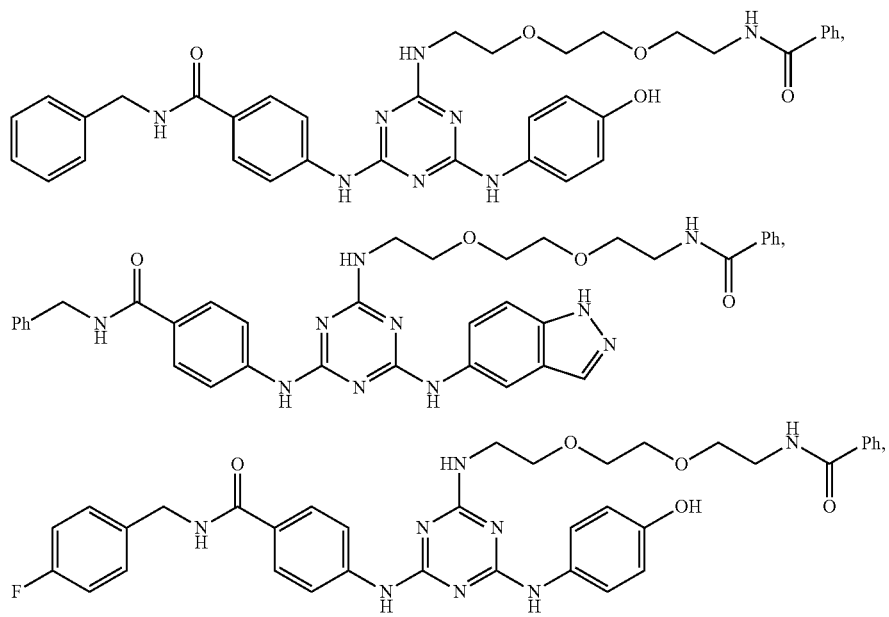

-continued
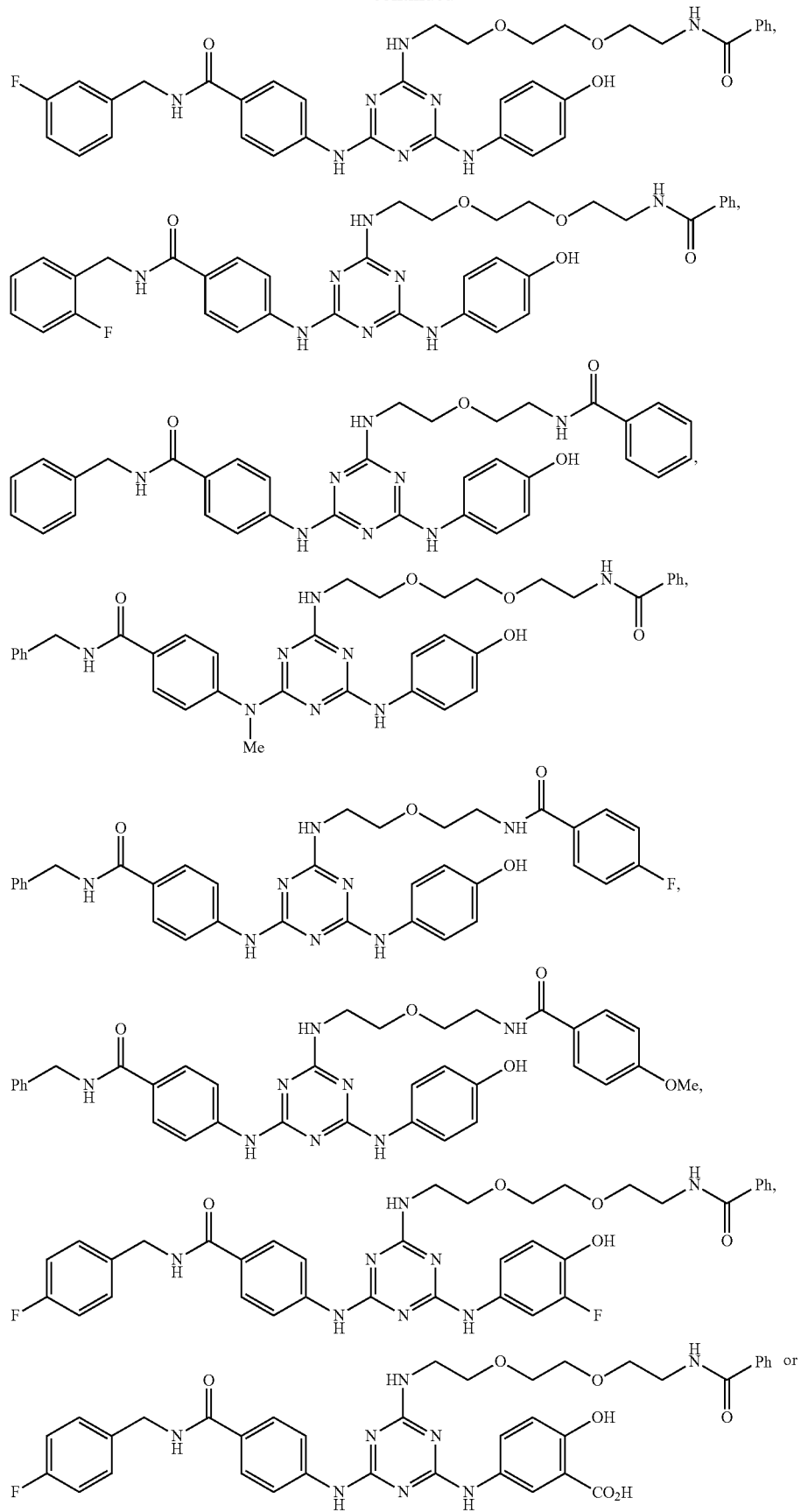

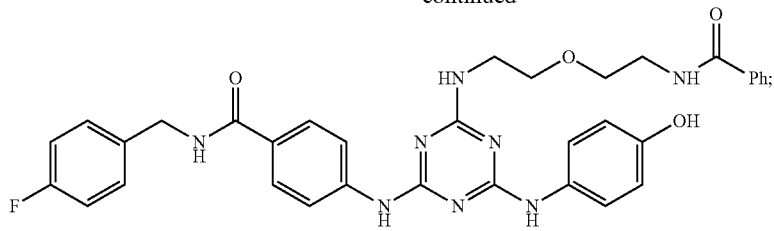

or a pharmaceutically acceptable salt thereof.

The invention also provides a pharmaceutical composition comprising any of the compounds disclosed herein and a pharmaceutically acceptable carrier. By "pharmaceutically acceptable" it is meant a material that (i) is compatible with the other ingredients of the composition without rendering the composition unsuitable for its intended purpose, and (ii) is suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include, without limitation, any of the standard pharmaceutical carriers such as phosphate buffered saline solutions, water, emulsions such as oil/water emulsions, microemulsions, and the like.

The invention provides a method of inhibiting prostaglandin transporter (PGT) activity in a subject comprising administering to the subject any of the compounds disclosed herein in an amount effective to inhibit PGT activity.

The invention also provides a method of inhibiting cyclooxygenase 2 (COX2) activity in a subject comprising administering to the subject any of the compounds disclosed herein in an amount effective to inhibit COX2 activity.

The invention further provides a method of treating a disease or disorder in a subject associated with prostaglandin activity and/or COX2 activity comprising administering to the subject any of the compounds disclosed herein in an amount effective to inhibit prostaglandin transporter (PGT) activity and/or COX2 activity. The disease or disorder can be, for example, arthritis, fever, common cold, hypertension, glaucoma, a wound, initiation of labor, dysmenorrhea, menstrual cramps, inflammatory bowel disease, Crohn's disease, emphysema, acute respiratory distress syndrome, asthma, bronchitis, chronic obstructive pulmonary disease, Alzheimer's disease, organ transplant toxicity, cachexia, allergic reactions, allergic contact hypersensitivity, cancer, tissue ulceration, peptic ulcers, gastritis, regional enteritis, ulcerative colitis, diverticulitis, recurrent gastrointestinal lesion, gastrointestinal bleeding, coagulation, anemia, synovitis, gout, ankylosing spondylitis, inflammation, restenosis, periodontal disease, epidermolysis bullosa, osteoporosis, loosening of artificial joint implants; atherosclerosis, aortic aneurysm, periarteritis nodosa, congestive heart failure, myocardial infarction, stroke, cerebral ischemia, head trauma, spinal cord injury, neuralgia, neuro-degenerative disorders, autoimmune disorders, Huntington's disease, Parkinson's disease, migraine, depression, peripheral neuropathy, pain, gingivitis, cerebral amyloid angiopathy, nootropic or cognition enhancement, amyotrophic lateral sclerosis, multiple sclerosis, ocular angiogenesis, corneal injury, macular degeneration, conjunctivitis, abnormal wound healing, muscle or joint sprains or strains, tendonitis, skin disorders, myasthenia gravis, polymyositis, myositis, bursitis, burns, diabetes, tumor invasion, tumor growth, tumor metastasis, corneal scarring, scleritis, immunodeficiency diseases, sepsis, premature labor, hyporothrombinemia, hemophilia, thyroiditis, sarcoidosis, Behcet's syndrome, hypersensitivity, kidney disease, rickettsial infections, protozoan diseases, reproductive disorders or septic shock. Preferably, the disease or disorder is inflammation, pain, a wound, or a cardiovascular disease, such as hypertension or atherosclerosis.

The above-described compounds can be formulated without undue experimentation for administration to a mammal, including humans, as appropriate for the particular application. Additionally, proper dosages of the compositions can be determined without undue experimentation using standard dose-response protocols.

Accordingly, compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like. Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, cornstarch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like.

The compounds can easily be administered parenterally such as for example, by intravenous, intramuscular, intrathecal or subcutaneous injection. Parenteral administration can be accomplished by incorporating the compounds into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the compound, in a pharmaceutical composition, into the rectum or large intestine. This can be accomplished using suppositories or enemas. Suppository formulations can easily be made by methods known in the art. For example, suppository formulations can be prepared by heating glycerin to about 120° C., dissolving the composition in the glycerin, mixing the heated glycerin after which purified water may be added, and pouring the hot mixture into a suppository mold.

Transdermal administration includes percutaneous absorption of the composition through the skin. Transdermal formulations include patches (such as the well-known nicotine patch), ointments, creams, gels, salves and the like.

Topical administration may be preferred for localized application of the compound, for example, for promoting wound healing or for ocular administration (e.g., eye drops).

The present invention includes nasally administering to the mammal a therapeutically effective amount of the compound, for example, as a nasal spray, nasal drop, suspension, gel, ointment, cream powder, or using a nasal tampon or nasal sponge.

Where the compound is administered peripherally such that it must cross the blood-brain barrier, the compound is preferably formulated in a pharmaceutical composition that enhances the ability of the compound to cross the blood-brain barrier of the mammal. Such formulations are known in the art and include lipophilic compounds to promote absorption. Uptake of non-lipophilic compounds can be enhanced by combination with a lipophilic substance. Lipophilic substances that can enhance delivery of the compound across the nasal mucus include but are not limited to fatty acids (e.g., palmitic acid), gangliosides (e.g., GM-1), phospholipids (e.g., phosphatidylserine), and emulsifiers (e.g., polysorbate 80), bile salts such as sodium deoxycholate, and detergent-like substances including, for example, polysorbate 80 such as Tween™, octoxynol such as Triton™ X-100, and sodium tauro-24,25-dihydrofusidate (STDHF).

In particular embodiments of the invention, the compound is combined with micelles comprised of lipophilic substanceS. Alternatively, the compound can be combined with liposomes (lipid vesicles) to enhance absorption. The compound can be contained or dissolved within the liposome and/or associated with its surface. Suitable liposomes include phospholipids (e.g., phosphatidylserine) and/or gangliosides (e.g., GM-1). Bile salts and their derivatives and detergent-like substances can also be included in the liposome formulation.

The invention also provides for the use of any of the compounds disclosed herein for treating a subject and for the use of any of the compounds disclosed herein for the preparation of a pharmaceutical composition for treating a subject, where the subject is being treated to inhibit prostaglandin transporter (PGT) activity or inhibit cyclooxygenase 2 (COX2) activity or the subject has a disease or disorder associated with prostaglandin activity and/or COX2 activity.

The present invention is illustrated in the following Experimental Details section, which is set forth to aid in the understanding of the invention, and should not be construed to limit in any way the scope of the invention as defined in the claims that follow thereafter.

EXPERIMENTAL DETAILS

A. Preparation of Chemical Compounds

Compounds were made according to one of 11 generic schemes described below. For each scheme, a specific example with a corresponding experimental description is given. Other compounds made via that same scheme are listed in tabular form beneath the experimental description. The compounds were synthesized at Provid Pharmaceuticals, Inc., North Brunswick N.J.

General procedures. HPLC was performed on Rainin SD-300 or Varian ProStar equipped with a single wavelength UV detector at 214 nm and linear gradients. Analytical HPLC was performed on a Varian $C_{18}$ column (microsorb 60-8, 4.6×250 mm) at a flow rate of 1 mL/min. Semi-preparative HPLC was performed on a Varian $C_{18}$ column (microsorb 60-8, 10.0×250 mm) at a flow rate of 5 mL/min. Preparative HPLC was routinely performed on a Varian $C_{18}$ column (microsorb 60-8, 21.4×250 mm) at a flow rate of 20 mL/min. The solvent system used on linear gradients was water with 0.075% TFA (solvent A) vs Acetonitrile with 0.075% TFA (solvent B). Silica gel used in flash column chromatography was obtained from Sorbent Technologies (Atlanta, Ga.). LC-MS spectra were taken on Waters ZQ LC/MS-ESI or APCI.

Scheme 1:

Generic Scheme:
Scheme 1

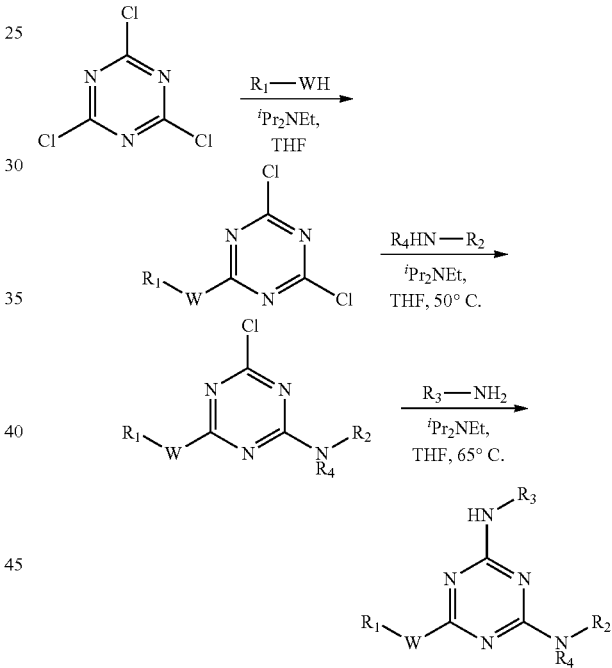

Experimental:

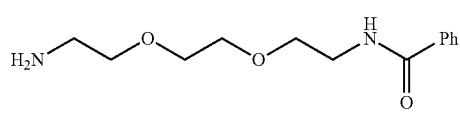

Preparation of amine 1: To a solution of Boc-1-amino-3,6-dioxa-8-octane diamine (1 eq.) and benzoyl chloride (1.2 eqs.) in $CH_2Cl_2$ (40 mL) was added TEA (2.5 eqs.). The reaction mixture was stirred overnight. Subsequently, the reaction mixture was partitioned between saturated aqueous $NaHCO_3$ and $CH_2Cl_2$, the layers separated, and the aqueous layer extracted with $CH_2Cl_2$ (3×). The combined organics were dried over $Na_2SO_4$, filtered and concentrated in vacuo.

The residue was used without further purification. The obtained residue was dissolved in TFA (20 mL) and stirred at ambient temperature for 1 hour. The reaction mixture was concentrated in vacuo and amine 1 was used without further purification.

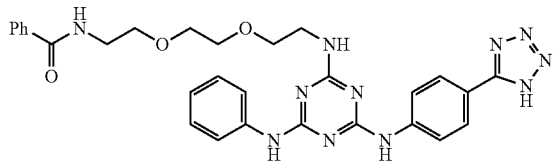

Preparation of triazine 2a: To a solution of cyanuric chloride (1.14 eqs) and aniline (1.0 eq.) in THF (27 mL) was added $^i$Pr$_2$NEt (3.0 eqs.). The reaction mixture was stirred at ambient temperature for 1 h. The reaction mixture was then partitioned between water and EtOAc, the layers separated, and the aqueous layer was extracted with EtOAc (3×). The combined organics were dried over Na$_2$SO$_4$, filtered and concentrated in vacuo. The residue was used without further purification.

To a solution of the residue (1.0 eq.) and 4-(1H-tetrazol-5-yl)aniline (1.1 eqs.) in THF (3.0 mL) was added $^i$Pr$_2$NEt (5.0 eqs.). The reaction mixture was warmed to 50° C. and stirred overnight. The reaction mixture was then cooled to ambient temperature and partitioned between EtOAc and water. The layers were separated and the aqueous extracted with EtOAc (3×). The combined organics were dried over Na$_2$SO$_4$, filtered and concentrated in vacuo. The residue was used without further purification.

To a solution of the residue (1.0 eq.) and amine 1 (1.1 eqs.) in THF (3.3 mL) was added $^i$Pr$_2$NEt (2.5 eqs.). Some methanol was added to help solubilize the starting material. The reaction mixture was warmed to 65° C. and stirred overnight. The reaction mixture was then cooled to ambient temperature and partitioned between EtOAc and water. The layers were separated and the aqueous extracted with EtOAc (3×). The combined organics were dried over Na$_2$SO$_4$, filtered and concentrated in vacuo. The obtained residue was purified via reverse phase HPLC to yield triazine 2a (4.3 mg, 2.2% overall yield). MS (LCMS, ESI): R$_t$=7.58 mins (>90% pure) m/z=582 (M+H)$^+$.

The following compounds were or could be made by the procedure described for triazine 2a:

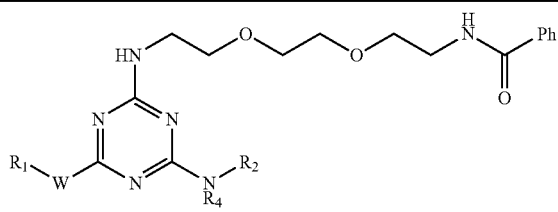

| Compound | W | R1 | R2 | R4 | (M + H)$^+$ |
|---|---|---|---|---|---|
| 2b | NH | Ph— | | H | 544 |
| 2c | NH | Ph— | | H | 620 |
| 2d | NMe | Me— | | H | 572 |
| 2e | NH | HO~~~( ) | | H | 588 |
| 2f | NH | Me-(O~~)$_3$-( ) | | H | 690 |

-continued
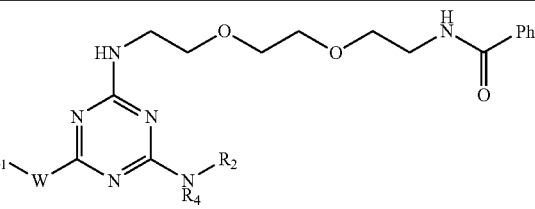
| Compound | W | R1 | R2 | R4 | (M + H)+ |
|---|---|---|---|---|---|
| 2g | NH | Ph— | 5-(1H-indazolyl) | H | 554 |
| 2h | NH | Ph— | 4-(CH2CO2Me)phenyl | H | 586 |
| 2i | NH | Ph— | 4-(CO2Me)phenyl | H | 572 |
| 2j | NH | Ph— | 6-(1H-indazolyl) | H | 554 |
| 2k | NH | Ph— | 5-(1H-benzotriazolyl) | H | 555 |
| 2l | O | H— | 4-hydroxyphenyl | H | 455 |
Scheme 2:
Generic Scheme:
Scheme 2
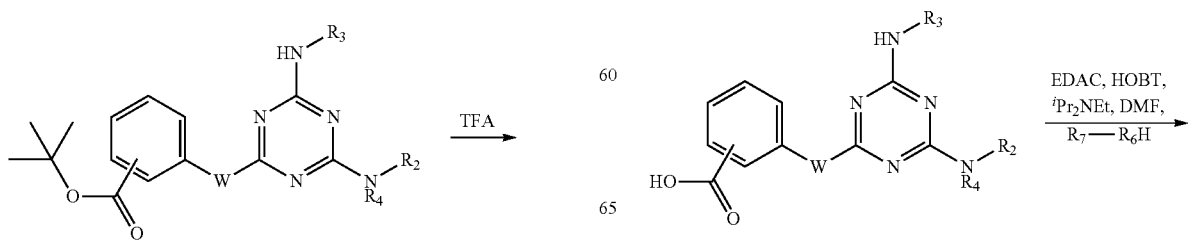
-continued -continued

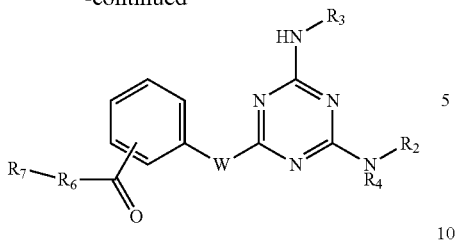

Experimental:

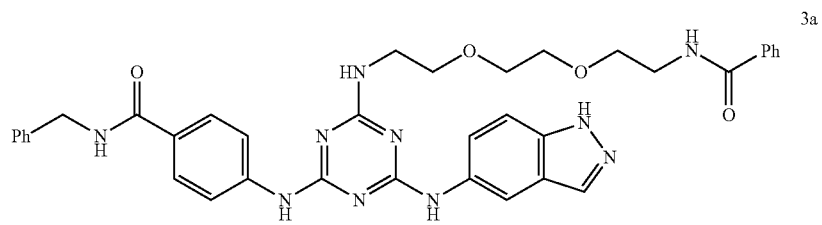 [SMILES: O=C(NCCOCCOCCNc1nc(Nc2ccc(C(=O)NCc3ccccc3)cc2)nc(Nc2ccc3[nH]ncc3c2)n1)c1ccccc1]

To a solution of cyanuric chloride (1.14 eqs.) and ᵗbutyl 4-aminobenzoate (1 eq.) in THF (81 mL) was added ⁱPr₂NEt (1.1 eqs.). The reaction mixture was stirred at ambient temperature for 1 hour. The reaction mixture was partitioned between water and EtOAc. The aqueous layer was extracted with EtOAc (3×), and the combined organics were dried over Na₂SO₄, filtered and concentrated in vacuo. The residue was used without further purification.

To a solution of the residue (1 eq.) and 5-aminoindazole (1.1 eqs.) in THF (22 mL) was added ⁱPr₂NEt (3.0 eqs.). The reaction mixture was warmed to 50° C. and stirred overnight. The reaction mixture was cooled to ambient temperature and partitioned between water and EtOAc. The aqueous layer was extracted with EtOAc (3×), and the combined organics were dried over Na₂SO₄, filtered and concentrated in vacuo. The residue was used without further purification.

To a solution of the residue (1 eq.) and amine 1 (1.1 eqs.) in THF (7.2 mL) was added ⁱPr₂NEt (3.0 eqs.). The reaction mixture was warmed to 65° C. and stirred overnight. The reaction mixture was then cooled to ambient temperature and partitioned between EtOAc and water. The layers were separated and the aqueous extracted with EtOAc (3×). The combined organics were dried over Na₂SO₄, filtered and concentrated in vacuo. The residue was purified via column chromatography over silica gel (2:1/hexanes:EtOAc→95:5/ CH₂Cl₂:MeOH) to yield a residue (0.115 g, 24% overall yield) that was used without further purification.

The residue (1 eq.) was dissolved in TFA (1.8 mL) and stirred at ambient temperature for 1 hour. The reaction mixture was then concentrated in vacuo and the obtained residue used without any further purification.

To a mixture of the residue (1 eq.), benzyl amine (1.1 eqs.), EDAC.HCl (1.2 eqs.) and anhydrous HOBT (1.2 eqs.) was added DMF (1.0 mL). Subsequently, ⁱPr₂NEt (10 eqs.) was added to the reaction mixture and the resulting solution stirred overnight. The reaction mixture was concentrated in vacuo and the residue purified via reverse-phase HPLC to yield triazine 3a (9.4 mg, 20% yield over 2 steps). MS (LCMS, ESI): $R_t$=7.56 mins (>90% pure) m/z=687 (M+H)⁺.

The following compounds were or could be made by the procedure described for triazine 3a:

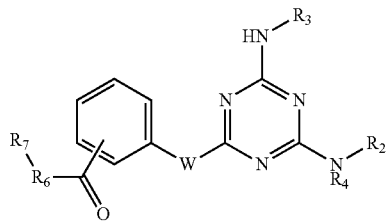

| Compound | W | R6 | R7 | R4 | R2 | R3 | (M + H)⁺ |
|---|---|---|---|---|---|---|---|
| 3b | NH | NH | Me(CH₂)₅— | H | 5-indazolyl | -(CH₂CH₂O)₂CH₂CH₂NHBz | 681 |

-continued

| Compound | W | R6 | R7 | R4 | R2 | R3 | (M + H)+ |
|---|---|---|---|---|---|---|---|
| 3c | NH | NH | 4-F-benzyl | H | 1H-indazol-5-yl | -(CH2CH2O)2-CH2CH2-NHBz | 705 |
| 3d | NH | NH | benzyl | H | phenyl | -(CH2CH2O)2-CH2CH2-NHBz | 647 |
| 3e | NH | NH | benzyl | H | 4-(CO2Me)-benzyl | -(CH2CH2O)2-CH2CH2-NHBz | 719 |
| 3f | NH | NH | benzyl | CH2CO2Me | 4-substituted phenyl | -(CH2CH2O)2-CH2CH2-NHBz | 719 |

Scheme 3:

Generic Scheme:
Scheme 3

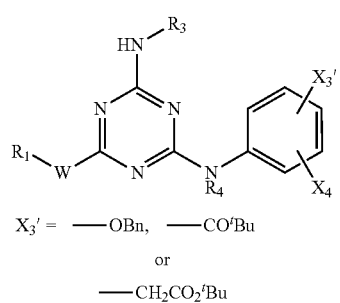

X3' = —OBn, —CO'Bu
or
—CH2CO2'Bu

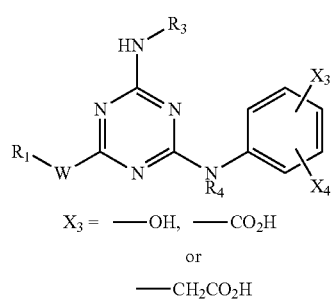

X3 = —OH, —CO2H
or
—CH2CO2H

Experimental:

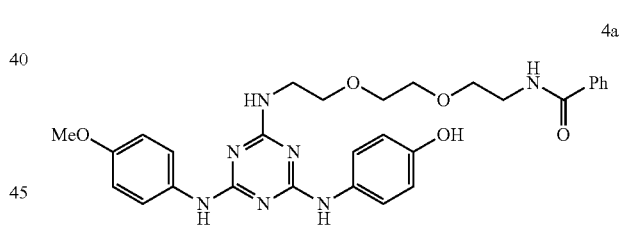

4a

Preparation of triazine 4a: To a solution of cyanuric chloride (1.14 eqs.) and 4-benzyloxy aniline hydrochloride (1 eq.) in THF (2.7 mL) was added $^i$Pr$_2$NEt (5.0 eqs.). The reaction mixture was allowed to stir at ambient temperature for 1.0 hour. Subsequently, p-anisidine (1.05 eqs.) was added to the reaction mixture and the reaction stirred overnight at 50° C. The reaction mixture was cooled to ambient temperature then partitioned between water and EtOAc, the layers separated, and the aqueous layer extracted with EtOAc (3×). The combined organics were dried over Na$_2$SO$_4$, filtered and concentrated in vacuo. The residue was used without further purification.

To a solution of the residue (1 eq.) and amine 1 (1.1 eqs.) in THF (2.4 mL) was added $^i$Pr$_2$NEt (1.5 eqs.). The reaction mixture was heated to 65° C. and stirred overnight. The reaction mixture was concentrated in vacuo and the residue filtered over a plug of silica gel (CH$_2$Cl$_2$→49:1/CH$_2$Cl$_2$:MeOH). The organics from the 49:1/CH$_2$Cl$_2$:MeOH elution were collected and concentrated in vacuo. The obtained residue was used without further purification.

A solution of benzyl ether (1 eq.) in TFA (1.2 mL) and DMS (1.2 mL) was heated to 40° C. and stirred overnight. The reaction mixture was then concentrated in vacuo and the residue purified via reverse phase HPLC to yield triazine 4a (18.0 mg, 13.6% overall yield). MS (LCMS, ESI): $R_t$=6.21 mins (>90% pure) m/z=560 (M+H)$^+$.

The following compounds were or could be made by the procedure described for triazine 4a:

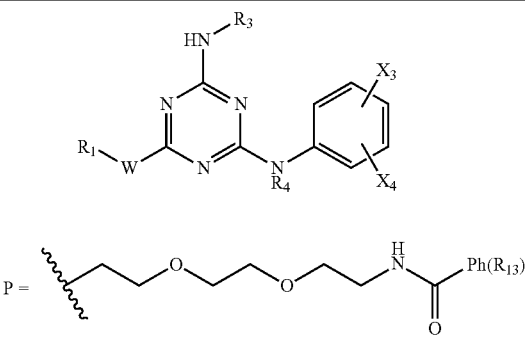

| Compound | W | R1 | R3 | R4 | X3 | X4 | (M + H)$^+$ |
|---|---|---|---|---|---|---|---|
| 4b | NH | Ph— | P | H | OH | H | 530 |
| 4c | NMe | Me— | P | H | OH | H | 482 |
| 4d | NH | HO~~~ | P | H | OH | H | 498 |
| 4e | NH | MeO~O~O~ | P | H | OH | H | 600 |
| 4f | NH | HO₂C-C₆H₄- | P | H | OH | H | 574 |
| 4g | NH | MeO₂C-C₆H₄- | P | H | OH | H | 588 |
| 4h | NH | morpholino-C₆H₄- | P | H | OH | H | 615 |
| 4i | NH | H₂N-C₆H₄- | P | H | OH | H | 545 |
| 4j | NH | HO-CH₂-C₆H₄- | P | H | OH | H | 560 |
| 4k | NH | cyclohexyl- | P | H | OH | H | 536 |
| 4l | NH | HO-C₆H₄- | P | H | OH | H | 546 |
| 4m | NH | Ph— | ~O~O~NH₂ | H | OH | H | 426 |
| 4n | NH | H₂N-SO₂-C₆H₄- | P | H | OH | H | 609 |

-continued
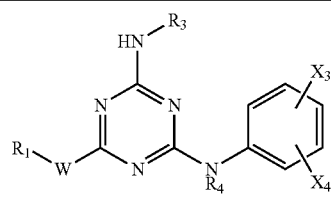
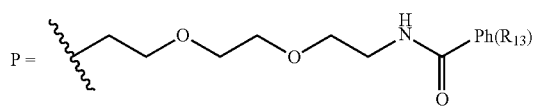
| Compound | W | R1 | R3 | R4 | X3 | X4 | (M + H)+ |
|---|---|---|---|---|---|---|---|
| 4o | NH | Ph— | —CH2CH2OCH2CH2OCH2C(O)OMe | H | OH | H | 455 |
| 4p | NH | Ph— | —(CH2)6C(O)OMe | H | OH | H | 437 |
| 4q | NH | Ph— | —(CH2)5Me | H | OH | H | 379 |
| 4r | NH | Ph— | P | H | OH | Cl | 564 |
| 4s | NH | Ph— | P | H | —CH2CO2H | H | 572 |
| 4t | NH | Ph— | P | H | —CO2H | H | 558 |
| 4u | NH | Ph— | —CH2CH2OCH2CH2NHC(O)Ph | H | OH | H | 486 |
| 4v | NH | Me(H2C)6C(O)-C6H4— | P | H | OH | H | 656 |
| 4w | NH | phthalimidyl | P | H | OH | H | 599 |
| 4x | NH | Ph— | —(CH2)6C(O)NHPh | H | OH | H | 498 |
| 4y | NH | Ph— | —(CH2)6C(O)NHBn | H | OH | H | 512 |
| 4z | NH | P | P | H | OH | H | 689 |

Scheme 4:

Generic Scheme:
Scheme 4

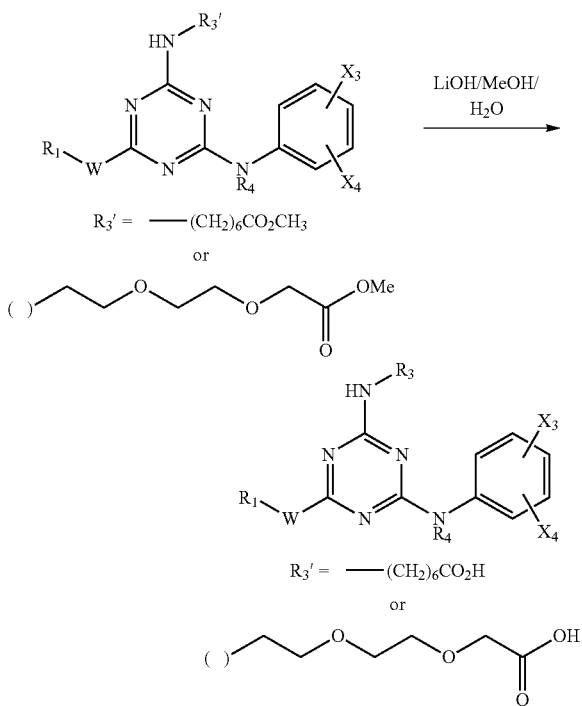

Experimental:

5

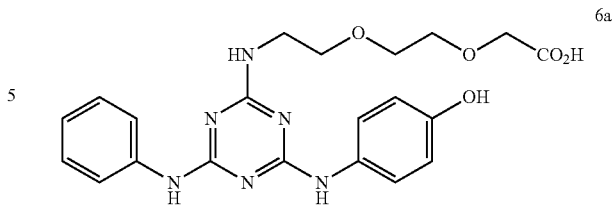

Preparation of amine 5: To a solution of 2-[2-(Boc-amino) ethoxy]ethoxy acetic acid dicyclohexylamine salt (1 eq.) in benzene (8 mL) and MeOH (2 mL) was added TMSCHN$_2$ (2.0 eqs.). The reaction mixture was stirred for 1.0 h, after which the reaction mixture was concentrated in vacuo. The obtained residue was then treated with saturated methanolic HCl. The resulting reaction mixture was stirred for 1 hour before being concentrated in vacuo. The residue was used without further purification.

Preparation of triazine product 6a: A solution of cyanuric chloride (1 eq.) in THF (5 mL) was treated with 4-benzyloxyaniline hydrochloride (0.85 eq.) and $^i$Pr$_2$NEt (2.0 eqs.) with stirring at ambient temperature for 0.5 h. The reaction mixture was poured into 50 mL EtOAc and the organic solution was washed with H$_2$O (2×) and with brine (1×). The organic layer was dried over MgSO4, filtered, and concentrated in vacuo. The obtained residue was used without further purification.

To a solution of the residue (1 eq.) and aniline (1.1 eqs.) in THF (7.2 mL) was added $^i$Pr$_2$NEt (2.0 eqs.). The reaction mixture was warmed to 50° C. and stirred overnight. The reaction mixture was cooled to ambient temperature and partitioned between water and EtOAc. The aqueous layer was extracted with EtOAc (3×), and the combined organics were dried over Na$_2$SO$_4$, filtered and concentrated in vacuo. The residue was used without further purification.

To a solution of chlorotriazine (1 eq.) and amine 5 (1.1 eqs.) in THF (3.5 mL) was added $^i$Pr$_2$NEt (3.0 eqs.). Subsequently, CH$_2$Cl$_2$ (1.0 mL) was added in order to make the reaction homogenous. The reaction mixture was warmed to 65° C. and stirred overnight. The reaction mixture was then cooled to ambient temperature and partitioned between EtOAc and water. The layers were separated and the aqueous extracted with EtOAc (3×). The combined organics were dried over Na$_2$SO$_4$, filtered and concentrated in vacuo. The residue was used without further purification.

To a solution of benzyl ether (1.0 eq.) in TFA (1.1 mL) was added DMS (1.1 mL). The reaction mixture was warmed to 35° C. and stirred overnight. The reaction mixture was concentrated in vacuo and the residue purified via reverse-phase HPLC to yield a residue that was used without further purification.

A heterogeneous mixture of methyl ester (1.0 eq.) and LiOH (30 eqs.) in THF (0.3 mL), MeOH (0.3 mL) and H$_2$O (0.3 mL) was stirred at ambient temperature overnight. The reaction mixture was then acidified via addition of TFA and the reaction mixture concentrated in vacuo. The residue was purified via reverse phase HPLC to yield triazine 6a (14.0 mg, 9.6% overall yield). MS (LCMS, ESI): R$_t$=5.55 mins (>90% pure) m/z=441 (M+H)$^+$.

The following compounds were or could be made by the procedure described for triazine 6a:

| Compound | W | R1 | R3 | R4 | X3 | X4 | (M + H)$^+$ |
|---|---|---|---|---|---|---|---|
| 6b | NH | Ph— | 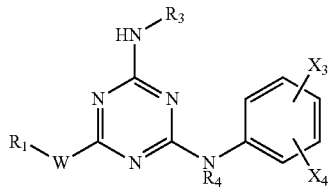 | H | OH | H | 423 |

Scheme 5:

Generic Scheme:
Scheme 5

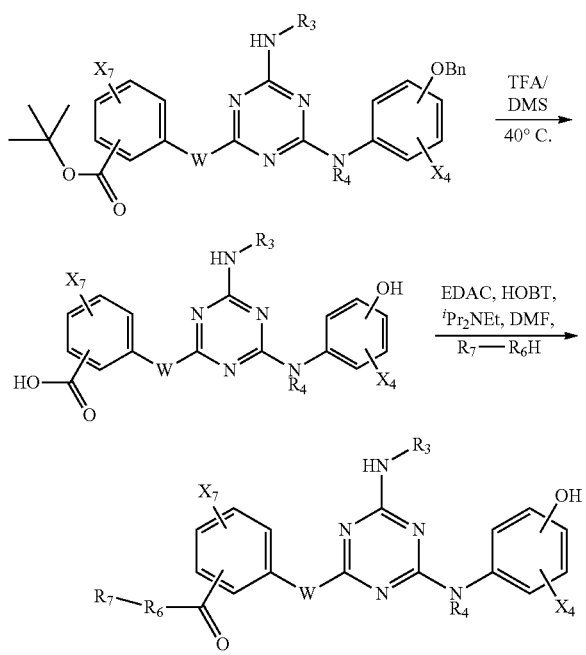

Experimental:

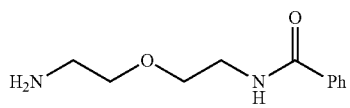

7

Preparation of amine 7: To a solution of bis(2-hydroxyethyl)ether (1.0 eq) and $^i$Pr$_2$NEt (4.0 eqs.) in CH$_2$Cl$_2$ (24 mL) was added MsCl (2.2 eqs.). The reaction mixture was stirred at ambient temperature for 1 h. The reaction mixture was partitioned between water and CH$_2$Cl$_2$, the layers separated, and the aqueous layer extracted with CH$_2$Cl$_2$ (3×). The combined organics were dried over Na$_2$SO$_4$, filtered and concentrated in vacuo. The residue was used without further purification.

To a solution of the residue (1.0 eq.) and NaI (0.2 eqs.) in DMF (24 mL) was added NaN$_3$ (2.3 eqs.). The reaction mixture was warmed to 65° C. and stirred overnight. The reaction mixture was cooled to ambient temperature then partitioned between water and ether. The layers were separated and the aqueous extracted with ether (3×). The combined organics were dried over Na$_2$SO$_4$, filtered and concentrated in vacuo. The residue was used without further purification.

To a solution of the residue (1.0 eq.) in THF (0.6 mL), ether (3 mL) and 1.0 M HCl (3 mL, aqueous) was added PPh$_3$ (1.05 eqs.). The reaction mixture was stirred at ambient temperature for 60 hours. Subsequently, the organics were removed from the reaction mixture in vacuo. Diethyl ether was added and the layers separated and the ethereal layer washed with 4.0 M HCl in water (50 mL). The combined aqueous layers were extracted with ether (2×) and the aqueous layer basicified to a pH~14 by addition of solid NaOH. The aqueous layer was then extracted with CH$_2$Cl$_2$ (3×) and the combined dichloromethane layers dried over Na$_2$SO$_4$, filtered and concentrated in vacuo. The obtained residue was used without further purification.

To a solution of the residue (1.0 eq.) and benzoyl chloride (1.1 eqs.) in CH$_2$Cl$_2$ (20 mL) was added TEA (2.5 eqs.). The reaction mixture was stirred overnight. Subsequently, the reaction mixture was partitioned between saturated aqueous NaHCO$_3$ and CH$_2$Cl$_2$, the layers separated, and the aqueous layer extracted with CH$_2$Cl$_2$ (3×). The combined organics were dried over Na$_2$SO$_4$, filtered and concentrated in vacuo. The residue (0.182 g, 33% crude yield over 4 steps) was used without further purification.

To a solution of the residue (1.0 eq.) in THF (3.2 mL) and H$_2$O (1.0 mL) was added PMe$_3$ (3.0 eqs.). The reaction mixture was stirred for 2 hours. The reaction mixture was concentrated in vacuo and the desired product used without further purification.

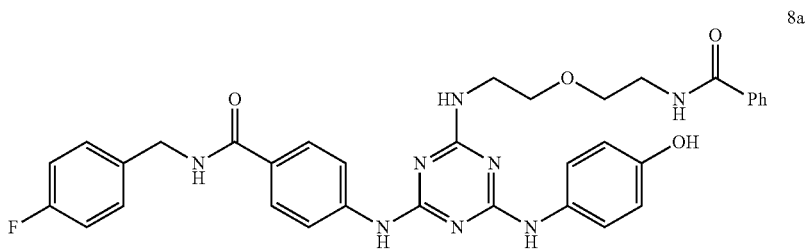 [SMILES: O=C(NCCOCCNc1nc(Nc2ccc(O)cc2)nc(Nc2ccc(C(=O)NCc3ccc(F)cc3)cc2)n1)c1ccccc1]

8a

Preparation of triazine 8a: To a solution of cyanuric chloride (1.14 eqs.) and 4-aminobenzoate (1.0 eq.) in THF (81 mL) was added $^i$Pr$_2$NEt (1.1 eqs.). The reaction mixture was stirred at ambient temperature for 1 hour. The reaction mixture was partitioned between water and EtOAc. The aqueous layer was extracted with EtOAc (3×), and the combined organics were dried over Na$_2$SO$_4$, filtered and concentrated in vacuo. The residue was used without further purification.

To a solution of the residue (1.0 eq.) and 4-benzyloxyaniline (1.1 eqs.) in THF (52 mL) was added $^i$Pr$_2$NEt (3.0 eqs). The reaction mixture was warmed to 50° C. and stirred overnight. The reaction mixture was cooled to ambient temperature and partitioned between water and EtOAc. The aqueous layer was extracted with EtOAc (3×), and the combined organics were dried over Na$_2$SO$_4$, filtered and concentrated in vacuo. The residue was used without further purification.

To a solution of the residue (1.0 eq.) and amine 7 (1.2 eqs.) in THF (1.5 mL) was added $^i$Pr$_2$NEt (3.0 eqs.). The reaction mixture was warmed to 65° C. and stirred overnight. The reaction mixture was concentrated in vacuo and the residue was purified via column chromatography over silica gel (2:1/ hexanes:EtOAc→98:2/CH₂Cl₂:MeOH). The obtained residue (0.024 g, 26% yield over 3 steps) was used without further purification.

The residue (1.0 eq.) was dissolved in TFA (1.0 mL) and DMS (1.0 mL). The reaction mixture was warmed to 50° C. and stirred overnight. The reaction mixture was concentrated in vacuo and the residue used without further purification.

To a mixture of the residue (1.0 eq.), 4-fluorobenzylamine (1.1 eqs.), EDAC.HCl (1.2 eqs.) and anhydrous HOBT (1.2 eqs.) was added DMF (1 mL). Subsequently, $^i$Pr₂NEt (3.0 eqs.) was added to the reaction mixture and the resulting solution stirred overnight. The reaction mixture was then concentrated in vacuo and the residue purified via reverse phase HPLC to yield triazine 8a (2.0 mg, 8.7% over 2 steps). MS (ESI): m/z=637 (M+H)⁺; analytical HPLC (10-90% MeCN in H₂O, 20 mins, flow rate=1.0 mL/min.) $R_t$=14.61 mins (>92% pure).

The following compounds were or could be made by the procedure described for triazine 8a:

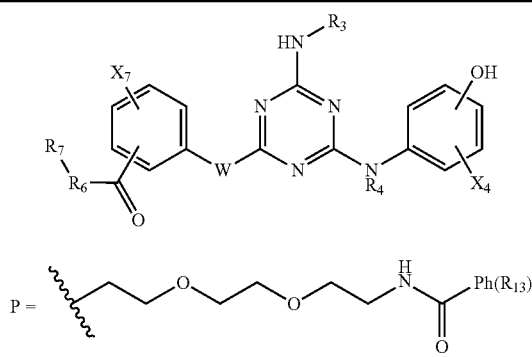

| Compound | W | X4 | X7 | R3 | R4 | R6 | R7 | (M + H)⁺ |
|---|---|---|---|---|---|---|---|---|
| 8b | NH | H | H | P | H | NH | Me— | 587 |
| 8c | NH | H | H | P | H | NMe | Me— | 601 |
| 8d | NH | H | H | P | H | NH | $^t$Bu— | 629 |
| 8e | NH | H | H | P | H | NH | HO-CH₂CH₂-O-CH₂CH₂—( ) | 661 |
| 8f | NH | H | H | P | H | NH | Me-(O-CH₂CH₂)₃—( ) | 719 |
| 8g | NH | H | H | P | H | NH | H— | 573 |
| 8h | NH$_{para}$ | H | H | P | H | NH | Bn- | 663 |
| 8i | NH | H | H | P | H | NH | MeO₂C(CH₂)₆— | 715 |
| 8j | NH | H | H | P | H | NH | Me(CH₂)₅— | 657 |
| 8k | NH | H | H | P | H | NH | MeO₂C-(CH₂-O)₂-CH₂—( ) | 733 |
| 8l | NH | H | H | P | H | NH | CMe₂Ph—( ) | 691 |
| 8m | NH | H | H | P | H | NH | 3-pyridylmethyl—( ) | 664 |
| 8n | NH | H | H | P | H | NMe | Bn- | 677 |
| 8o | NH | H | H | P | H | O | Bn- | 664 |
| 8p | NH | H | H | P | H | NH | 2-pyridylmethyl—( ) | 664 |
| 8q | NH | H | H | P | H | NH | 4-pyridylmethyl—( ) | 664 |

-continued
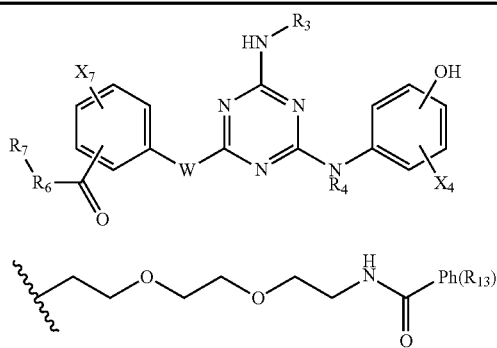
| Compound | W | X4 | X7 | R3 | R4 | R6 | R7 | (M + H)+ |
|---|---|---|---|---|---|---|---|---|
| 8r | NH | H | H | P | H | NH | MeO2C—CH(Ph)— | 721 |
| 8s | NH | H | H | P | H | NH | MeO2C—CH(Ph)— | 721 |
| 8t | NH*meta* | H | H | P | H | NH | Bn- | 663 |
| 8u | NH | H | —OMe | P | H | NH | Bn- | 693 |
| 8v | NH | H | —CF3 | P | H | NH | Bn- | 731 |
| 8w | O | H | H | P | H | NH | Bn- | 664 |
| 8x | NH | H | H | P | H | NH | 2-Ph-C6H4-CH2- | 739 |
| 8y | NH | H | H | P | H | NH | 3-Cl-C6H4-CH2- | 697 |
| 8z | NH | H | H | P | H | NH | 3-MeO-C6H4-CH2- | 693 |
| 8aa | NH | H | H | P | H | NH | 1-naphthyl-CH2- | 713 |
| 8bb | NH | H | H | P | H | NH | 3-Ph-C6H4-CH2- | 739 |
| 8cc | NH | H | H | P | H | NH | 4-Cl-C6H4-CH2- | 697 |
| 8dd | NH | H | H | P | H | NH | 4-MeO-C6H4-CH2- | 693 |

-continued
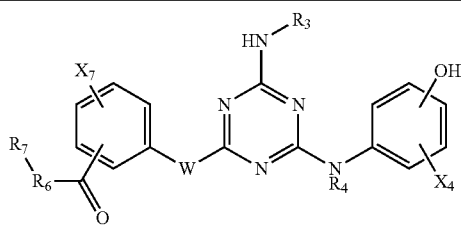
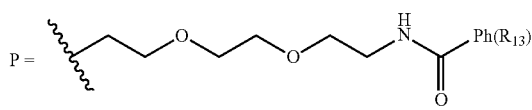
| Compound | W | X4 | X7 | R3 | R4 | R6 | R7 | $(M+H)^+$ |
|---|---|---|---|---|---|---|---|---|
| 8ee | NH | H | H | P | H | NH | 4-Ph-C6H4-CH2- | 739 |
| 8ff | NH | H | H | P | H | NH | (1H-indol-5-yl)-CH2- | 702 |
| 8gg | NH | H | H | -CH2CH2-O-CH2CH2-NHBz | H | NH | 4-Cl-C6H4-CH2- | 653 |
| 8hh | NH | H | H | P | H | NH | 4-F-C6H4-CH2- | 681 |
| 8ii | NH | H | H | P | H | NH | 2,4-diCl-C6H3-CH2- | 731 |
| 8jj | NH | H | H | P | H | NH | 3-CF3-C6H4-CH2- | 731 |
| 8kk | NH | H | H | P | H | NH | 4-Me-C6H4-CH2- | 677 |
| 8ll | NH | H | H | P | H | NH | Ph— | 649 |
| 8mm | NH | H | H | P | H | NH | 3,4-diCl-C6H3-CH2- | 731 |
| 8nn | NH | H | H | P | H | NH | 3-F-C6H4-CH2- | 681 |

-continued

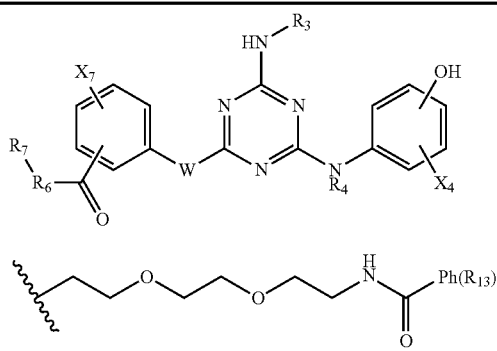

| Compound | W | X4 | X7 | R3 | R4 | R6 | R7 | (M + H)+ |
|---|---|---|---|---|---|---|---|---|
| 8oo | NH | H | H | P | H | NH | 2-Cl-benzyl | 697 |
| 8pp | NH | H | H | P | H | NH | 3-Me-benzyl | 677 |
| 8qq | NH | H | H | P | H | NH | 3,5-diCl-benzyl | 731 |
| 8rr | NH | H | H | P | H | NH | 4-Br-benzyl | 741 |
| 8ss | NH | H | H | P | H | NH | 2-F-benzyl | 681 |
| 8tt | NH | H | H | P | H | NH | phenethyl | 677 |
| 8uu | NH | H | H | P | H | NH | 4-CF$_3$-benzyl | 731 |
| 8vv | NH | H | H | P | H | NH | cyclohexylmethyl | 669 |
| 8ww | NH | H | H | -CH$_2$CH$_2$OCH$_2$CH$_2$NHBz | H | NH | Bn- | 619 |
| 8xx | NH | H | H | -CH$_2$CH$_2$OCH$_2$CH$_2$NHBz | H | NH | Me(CH$_2$)$_5$— | 613 |
| 8yy | NH | H | H | —(CH$_2$)$_5$Me | H | NH | Bn- | 512 |
| 8zz | NH | H | H | P | Me | NH | Bn- | 677 |
| 8aaa | NMe | H | H | P | H | NH | Bn- | 677 |

-continued
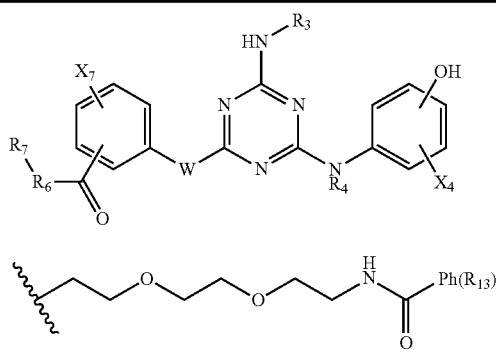
| Compound | W | X4 | X7 | R3 | R4 | R6 | R7 | (M + H)+ |
|---|---|---|---|---|---|---|---|---|
| 8bbb | NH | H | H | P | H | NH | 2,3-difluorobenzyl | 699 |
| 8ccc | NH | H | H | P | H | NH | 2,4-difluorobenzyl | 699 |
| 8ddd | NH | H | H | P | H | NH | 2,5-difluorobenzyl | 699 |
| 8eee | NH | H | H | P | H | NH | 2,6-difluorobenzyl | 699 |
| 8fff | NH | H | H | P | H | NH | 3,4-difluorobenzyl | 699 |
| 8ggg | NH | H | H | P | H | NH | 3,5-difluorobenzyl | 699 |
| 8hhh | NH | F | H | P | H | NH | 4-fluorobenzyl | 699 |
| 8iii | NH | CO2Me | H | P | H | NH | 4-fluorobenzyl | 739 |
| 8jjj | NH | H | H | 4-hydroxyphenyl | H | NH | 4-fluorobenzyl | 538 |

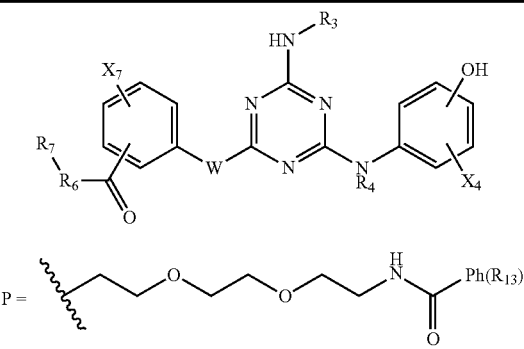

| Compound | W | X4 | X7 | R3 | R4 | R6 | R7 | (M + H)+ |
|---|---|---|---|---|---|---|---|---|
| 8kkk | NH | H | H | —(CH₂CH₂O)CH₂CH₂NHBz | H | NH | 4-F-benzyl | 637 |
| 8lll | NH | H | H | 4-substituted-N-(4-fluorobenzyl)benzamide | H | NH | 4-F-benzyl | 673 |
| 8mmm | NH | H | H | P | H | NH | N₃-(CH₂CH₂O)₂-CH₂CH₂- | 730 |

Scheme 6:
Generic Scheme:
Scheme 6

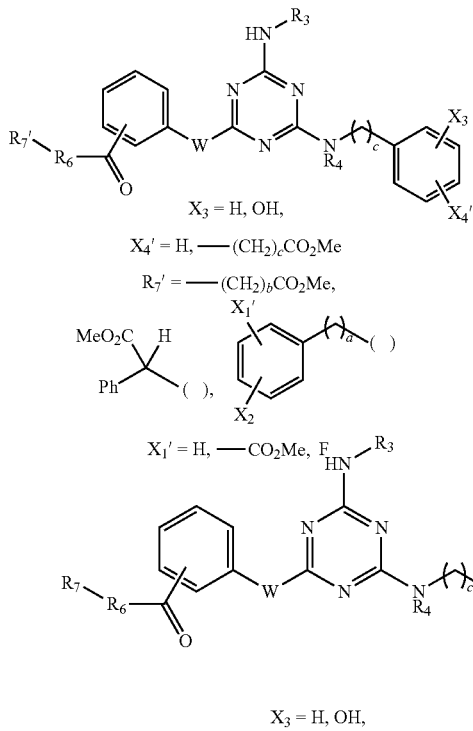

$X_3 = H, OH,$ $X_4 = H, \text{---}(CH_2)_c CO_2 H$ $R_7 = \text{---}(CH_2)_b CO_2 H,$

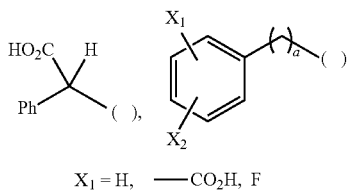

$X_1 = H, \text{---}CO_2H, F$

Experimental:

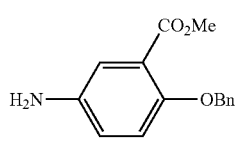

9

Preparation of aniline 9: To a solution of methyl 5-amino salicylate (1.0 eq.), in MeOH (10 mL) was added Boc₂O (1.1 eqs.) followed by TEA (1.1 eqs.). The reaction mixture was allowed to stir for 1 hour. Subsequently, imidazole (0.5 eqs.) was added and the reaction mixture stirred for 10 mins at ambient temperature. The reaction mixture was concentrated in vacuo and the residue partitioned between CH₂Cl₂ and water. The layers were separated and the aqueous extracted with CH₂Cl₂ (3×). The combined organics were then washed with 0.1 M HCl (1x, aqueous), dried over Na₂SO₄, filtered and concentrated in vacuo. The residue was used without further purification.

To a solution of the residue (1.0 eq.) in DMF (10 mL) was added K$_2$CO$_3$ (1.2 eqs.) followed by BnBr (1.1 eqs.). The reaction mixture was heated to 60° C. and stirred overnight. The reaction mixture was concentrated in vacuo and the residue partitioned between CH$_2$Cl$_2$ and water. The layers were separated and the aqueous extracted with CH$_2$Cl$_2$ (3×). The combined organics were dried over Na$_2$SO$_4$, filtered and concentrated in vacuo. The residue was used without further purification.

The residue was dissolved EtOAc (3 mL) and concentrated HCl (3 mL) was added. The reaction mixture was stirred for 1 hour at ambient temperature before the reaction mixture was concentrated in vacuo. The residue was used without further purification.

To a solution of the residue (1.0 eq.) and amine 1 (1.2 eqs.) in THF (1.5 mL) was added $^i$Pr$_2$NEt (3.0 eqs.). The reaction mixture was warmed to 65° C. and stirred overnight. The reaction mixture was concentrated in vacuo and the residue was purified via column chromatography over silica gel (2:1/hexanes:EtOAc→98:2/CH$_2$Cl$_2$:MeOH). The obtained residue (0.116 g, 78% yield over 3 steps) was used without further purification.

The residue (1.0 eq.) was dissolved in TFA (1.0 mL) and DMS (1.0 mL). The reaction mixture was warmed to 50° C. and stirred overnight. The reaction mixture was concentrated in vacuo and the residue used without further purification.

To a mixture of the residue (1.0 eq.), 4-fluorobenzylamine (1.1 eqs.), EDAC.HCl (1.2 eqs.) and anhydrous HOBT (1.2

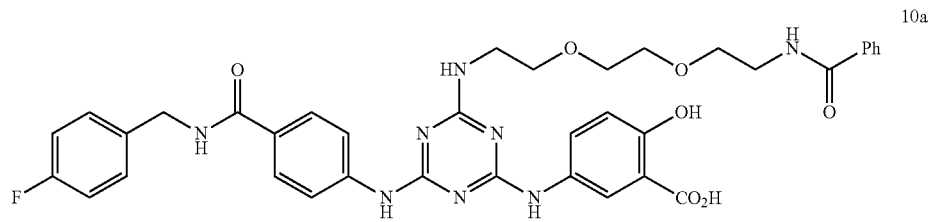 [SMILES: O=C(NCCOCCOCCNc1nc(Nc2ccc(C(=O)NCc3ccc(F)cc3)cc2)nc(Nc2ccc(O)c(C(=O)O)c2)n1)c1ccccc1]

10a

To a solution of cyanuric chloride (1.14 eqs.) and $^t$butyl 4-aminobenzoate (1.0 eq.) in THF (81 mL) was added $^i$Pr$_2$NEt (1.1 eqs.). The reaction mixture was stirred at ambient temperature for 1 hour. The reaction mixture was partitioned between water and EtOAc. The aqueous layer was extracted with EtOAc (3×), and the combined organics were dried over Na$_2$SO$_4$, filtered and concentrated in vacuo. The residue was used without further purification.

To a solution of the residue (1.0 eq.) and aniline 9 (1.1 eqs.) in THF (52 mL) was added $^i$Pr$_2$NEt (3.0 eqs). The reaction mixture was warmed to 50° C. and stirred overnight. The reaction mixture was cooled to ambient temperature and partitioned between water and EtOAc. The aqueous layer was extracted with EtOAc (3×), and the combined organics were dried over Na$_2$SO$_4$, filtered and concentrated in vacuo. The residue was used without further purification.

eqs.) was added DMF (1 mL). Subsequently, $^i$Pr$_2$NEt (3.0 eqs.) was added to the reaction mixture and the resulting solution stirred overnight. The reaction mixture was then concentrated in vacuo and the residue purified via reverse phase HPLC to yield triazine 8iii (25.0 mg, 18% yield over 2 steps).

A heterogeneous mixture of triazine 8iii (1.0 eq.) and LiOH (30 eq.) in THF (0.3 mL), MeOH (0.3 mL) and H$_2$O (0.3 mL) was stirred at ambient temperature overnight. The reaction mixture was then concentrated in vacuo and the residue purified via reverse phase HPLC to yield triazine 10a (13.0 mg, 59% yield):MS (ESI): m/z=725 (M+H)$^+$; analytical HPLC (10-90% MeCN in H$_2$O, 20 mins, flow rate=1.0 mL/min.) R$_t$=14.91 mins (>96% pure).

The following compounds were or could be made by the procedure described for triazine 10a:

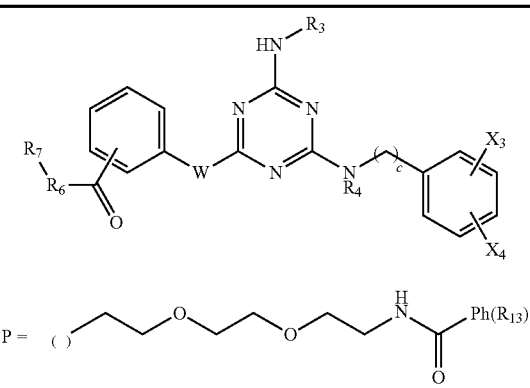

| Compound | W | X3 | X4 | C | R3 | R4 | R6 | R7 | (M + H)$^+$ |
|---|---|---|---|---|---|---|---|---|---|
| 10b | NH | OH | H | 0 | P | H | NH | CO$_2$H(CH$_2$)$_6$— | 701 |
| 10c | NH | OH | H | 0 | P | H | NH | 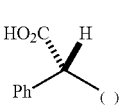 | 707 |

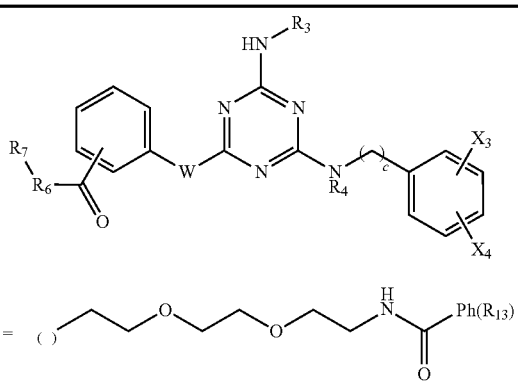

| Compound | W | X3 | X4 | C | R3 | R4 | R6 | R7 | (M + H)+ |
|---|---|---|---|---|---|---|---|---|---|
| 10d | NH | OH | H | 0 | P | H | NH | 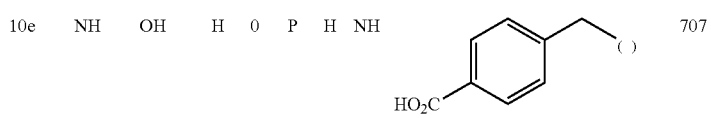 HO₂C, H, Ph ( ) | 707 |
| 10e | NH | OH | H | 0 | P | H | NH | 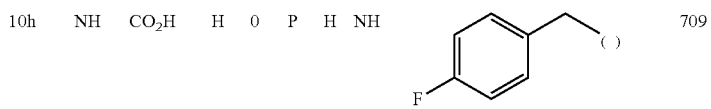 HO₂C— ( ) | 707 |
| 10f | NH | CO₂H | H | 1 | P | H | NH | Bn- | 705 |
| 10g | NH | CH₂CO₂H | H | 0 | P | H | NH | Bn- | 705 |
| 10h | NH | CO₂H | H | 0 | P | H | NH | F—⟨⟩—CH₂( ) | 709 |

Scheme 7:
Generic Scheme:
 Scheme 7

Experimential:

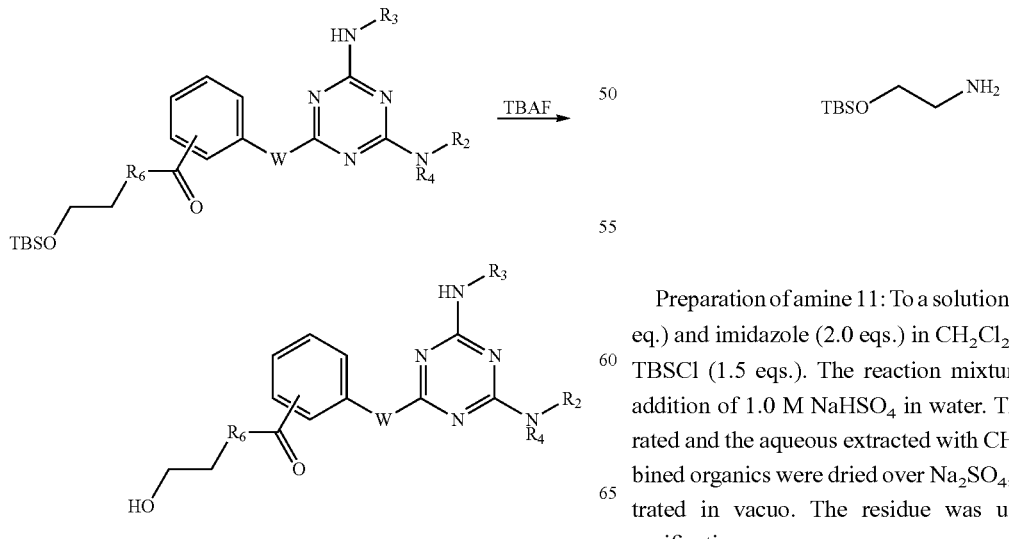

Preparation of amine 11: To a solution of ethanolamine (1.0 eq.) and imidazole (2.0 eqs.) in CH₂Cl₂ (8.0 mL) was added TBSCl (1.5 eqs.). The reaction mixture was quenched by addition of 1.0 M NaHSO₄ in water. The layers were separated and the aqueous extracted with CH₂Cl₂ (3×). The combined organics were dried over Na₂SO₄, filtered and concentrated in vacuo. The residue was used without further purification.

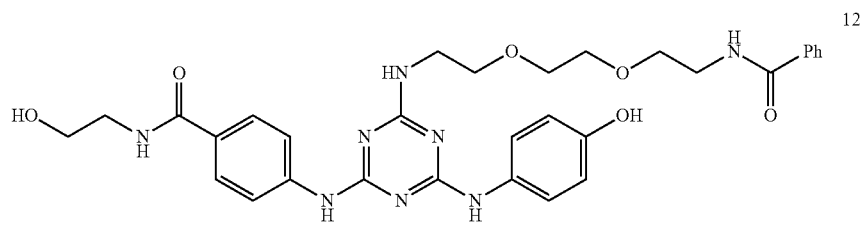 [SMILES: O=C(NCCO)c1ccc(Nc2nc(NCCOCCOCCNC(=O)c3ccccc3)nc(Nc3ccc(O)cc3)n2)cc1]

Preparation of triazine 12: To a solution of cyanuric chloride (1.14 eqs.) and 'butyl 4-aminobenzoate (1.0 eq.) in THF (81 mL) was added $^i$Pr$_2$NEt (1.1 eqs.). The reaction mixture was stirred at ambient temperature for 1 hour. The reaction mixture was partitioned between water and EtOAc, the layers separated and the aqueous layer was extracted with EtOAc (3×). The combined organics were dried over Na$_2$SO$_4$, filtered and concentrated in vacuo. The residue was used without further purification.

To a solution of the residue (1.0 eq.) and 4-benzyloxyaniline (1.1 eqs.) in THF (52 mL) was added $^i$Pr$_2$NEt (3.0 eqs.). The reaction mixture was warmed to 50° C. and stirred overnight. The reaction mixture was cooled to ambient temperature and partitioned between water and EtOAc. The aqueous layer was extracted with EtOAc (3×), and the combined organics were dried over Na$_2$SO$_4$, filtered and concentrated in vacuo. The residue was used without further purification.

To a solution of the residue (1.0 eq.) and amine 1 (1.2 eqs.) in THF (1.5 mL) was added $^i$Pr$_2$NEt (3.0 eqs.). The reaction mixture was warmed to 65° C. and stirred overnight. The reaction mixture was concentrated in vacuo and the residue was purified via column chromatography over silica gel (2:1/hexanes:EtOAc→98:2/CH$_2$Cl$_2$:MeOH). The obtained residue (0.116 g, 78% yield over 3 steps) was used without further purification.

The residue (1.0 eq.) was dissolved in TFA (1.0 mL) and DMS (1.0 mL). The reaction mixture was warmed to 50° C. and stirred overnight. The reaction mixture was concentrated in vacuo and the residue used without further purification.

To a mixture of the residue (1.0 eq), amine 11 (1.1 eqs.), EDAC.HCl (1.2 eqs.) and anhydrous HOBT (1.2 eqs.) was added DMF (1.0 mL). Subsequently, $^i$Pr$_2$NEt (3.0 eqs.) was added to the reaction mixture and the resulting solution stirred overnight. The reaction mixture was concentrated in vacuo. The residue was dissolved in THF (1.0 mL) and to the solution was added TBAF (1.1 eqs.). The reaction mixture was stirred for 1 hour. The reaction mixture was then concentrated in vacuo and the residue purified via reverse phase HPLC to yield triazine 12 (13.0 mg, 41% yield): MS (LCMS, ESI): R$_t$=5.24 mins (>90% pure) m/z=617(M+H)$^+$.

Scheme 8:
Generic Scheme:
Scheme 8

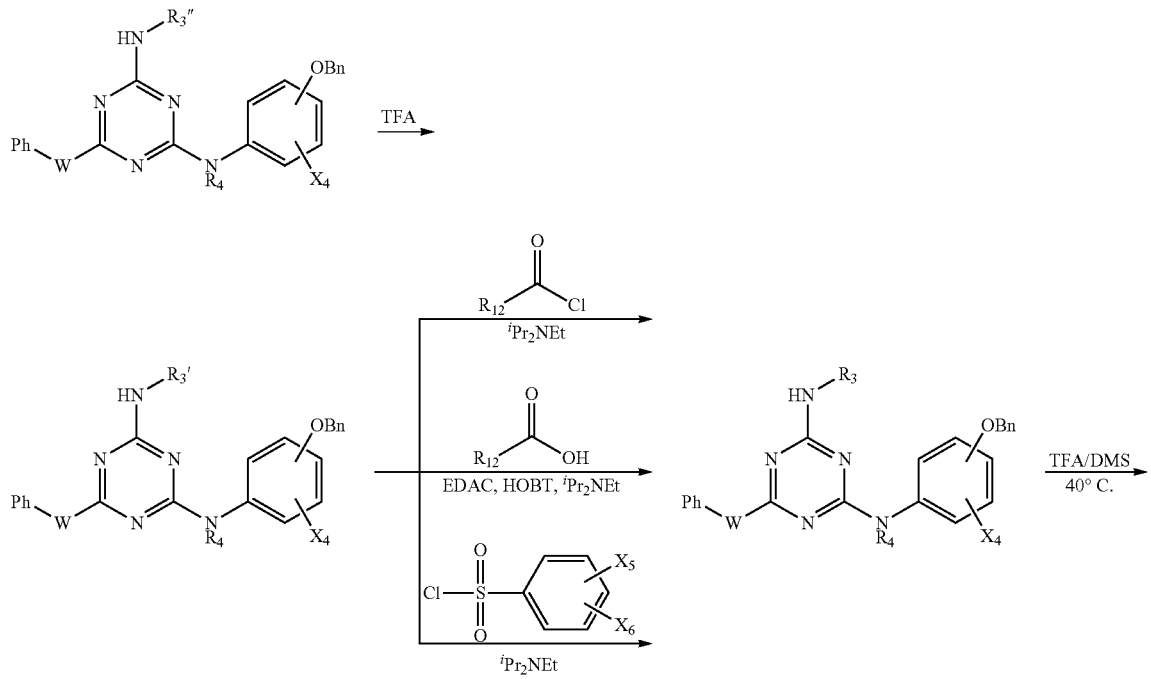

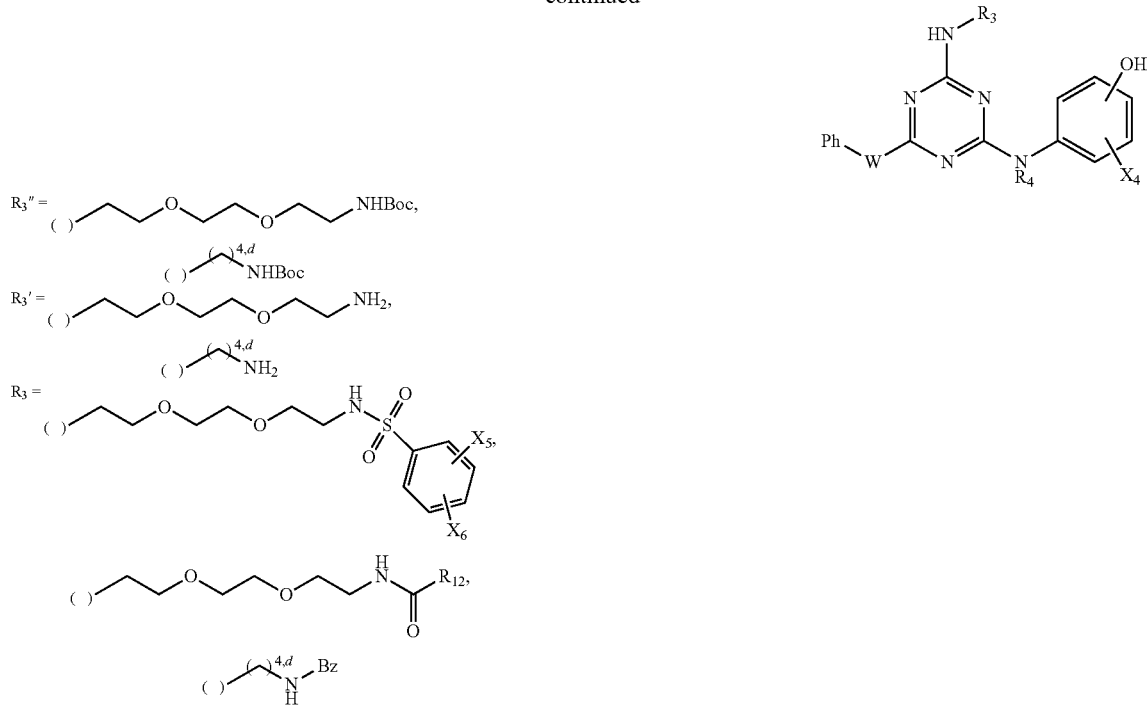

Experimental:

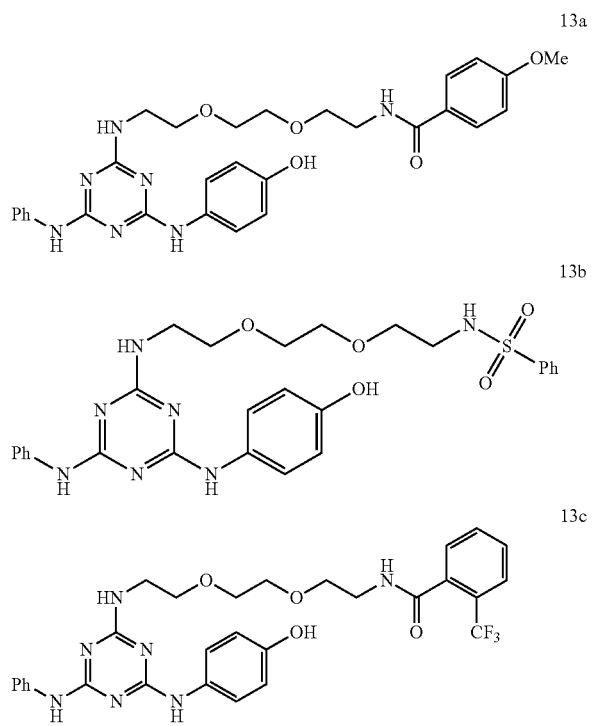

A solution of cyanuric chloride (1 eq.) in THF (5 mL) was treated with 4-benzyloxyaniline hydrochloride (0.85 eq.) and $^i$Pr$_2$NEt (2.0 eqs.) with stirring at ambient temperature for 0.5 h. The reaction mixture was poured into 50 mL EtOAc and the organic solution was washed with H$_2$O (2×) and with brine (1×). The organic layer was dried over MgSO4, filtered, and concentrated in vacuo. The obtained residue was used without further purification.

To a solution of the residue (1.0 eq.) in THF (29 mL) was added $^i$Pr$_2$NEt (2.0 eqs.) followed by aniline (1.1 eqs.). The reaction mixture was heated to 50° C. and stirred for 4 hours. The reaction mixture was cooled to ambient temperature and partitioned between EtOAc and water. The layers were separated and the aqueous extracted with EtOAc (3×). The combined organics were dried over Na$_2$SO$_4$, filtered and concentrated in vacuo. The residue was used without further purification.

To a solution of the residue (1 eq.) and Boc-1-amino-3,6-dioxa-8-octanediamine (1.1 eqs.) in THF (29 mL) was added $^i$Pr$_2$NEt (2.5 eqs.). The reaction mixture was warmed to 65° C. and stirred overnight. The reaction mixture was then cooled to ambient temperature and partitioned between EtOAc and water. The layers were separated and the aqueous extracted with EtOAc (3×). The combined organics were dried over Na$_2$SO$_4$, filtered and concentrated in vacuo. The residue was used without further purification.

To a solution of the residue (1 eq.) in CH$_2$Cl$_2$ (29 mL) was added TFA (9.5 mL). The reaction mixture was stirred for 1 h after which the reaction mixture was concentrated in vacuo. The residue was used without further purification.

Preparation of triazine 13a: To a solution of the residue (1 eq.) and 4-methoxybenzoyl chloride (1.1 eqs.) in CH$_2$Cl$_2$ (1.0 mL) was added $^i$Pr$_2$NEt (4 eqs.). The reaction mixture was stirred overnight. The reaction mixture was then concentrated in vacuo and the residue used without further purification.

A solution of the residue (1 eq.) in DMS (0.5 mL) and TFA (0.5 mL) was heated to 40° C. and stirred overnight. The reaction mixture was then concentrated in vacuo and the residue purified via reverse phase HPLC to yield triazine 13a (6.6 mg, 25% overall yield). MS (LCMS, ESI): R$_t$=6.43 mins (>90% pure) m/z=560 (M+H)$^+$.

Preparation of triazine 13b: To a solution of the residue (1 eq.) and benzenesulfonyl chloride (1.1 eqs.) in CH$_2$Cl$_2$ (1.0 mL) was added $^i$Pr$_2$NEt (4 eqs.). The reaction mixture was stirred overnight. The reaction mixture was then concentrated in vacuo and the residue used without further purification.

A solution of the residue (1 eq.) in DMS (0.5 mL) and TFA (0.5 mL) was heated to 40° C. and stirred overnight. The reaction mixture was then concentrated in vacuo and the residue purified via reverse phase HPLC to yield triazine 13b (5.8 mg, 22% overall yield). MS (LCMS, ESI): R$_t$=6.98 mins (>90% pure) m/z=566 (M+H)$^+$ Preparation of triazine 13c: To a mixture of the residue (1.0 eq.), α, α, α-trifluoromethyl toluic acid (1.1 eqs.), EDAC.HCl (1.2 eqs.) and anhydrous HOBT (1.2 eqs.) was added DMF (1.0 mL). Subsequently, $^i$Pr$_2$NEt (10 eqs.) was added to the reaction mixture and the resulting solution stirred overnight. The reaction mixture was concentrated in vacuo and the residue used without further purification.

A solution of the residue (1 eq.) in DMS (0.5 mL) and TFA (0.5 mL) was heated to 40° C. and stirred overnight. The reaction mixture was then concentrated in vacuo and the residue purified via reverse phase HPLC to yield triazine 13c (11.0 mg, 32% overall yield). MS (LCMS, ESI): R$_t$=7.05 mins (>90% pure) m/z=598 (M+H)$^+$ The following compounds were or could be made by the procedures described for triazines 13a, 13b or 13c:

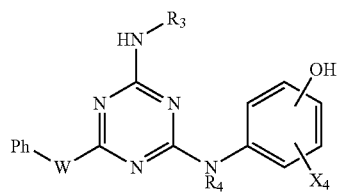

| Compound | W | X4 | R3 | R4 | (M + H)$^+$ |
|---|---|---|---|---|---|
| 13d | NH | H | ![structure] | H | 531 |
| 13e | NH | H | ![structure] | H | 548 |
| 13f | NH | H | ![structure] | H | 608 |
| 13g | NH | H | ![structure] | H | 531 |
| 13h | NH | H | ![structure] | H | 548 |
| 13i | NH | H | ![structure] | H | 566 |

-continued
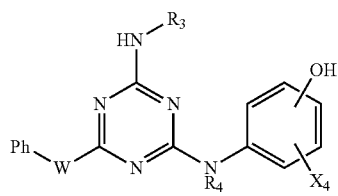
| Compound | W | X4 | R3 | R4 | (M + H)+ |
|---|---|---|---|---|---|
| 13j | NH | H | PEG2-NHC(O)-(3-Br-C6H4) | H | 608 |
| 13k | NH | H | PEG2-NHC(O)-(3-OMe-C6H4) | H | 560 |
| 13l | NH | H | PEG2-NHC(O)-(2-thienyl) | H | 536 |
| 13m | NH | H | PEG2-NHC(O)-(4-Ph-C6H4) | H | 606 |
| 13n | NH | H | PEG2-NHC(O)Me | H | 468 |
| 13o | NH | H | PEG2-NHC(O)NHPh | H | 545 |
| 13p | NH | H | -(CH2)3-NHBz | H | 470 |
| 13q | NH | H | -(CH2)4-NHBz | H | 484 |
| 13r | NH | H | -(CH2)5-NHBz | H | 498 |
| 13s | NH | H | -(CH2)6-NHBz | H | 512 |

Scheme 9:

Generic Scheme:
Scheme 9

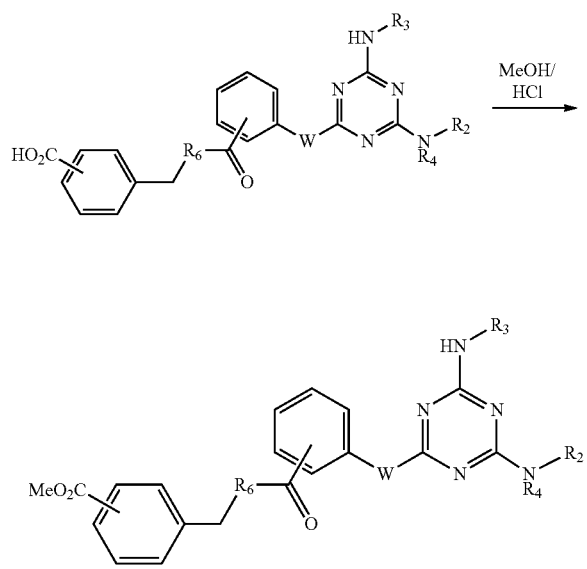

Experimental:

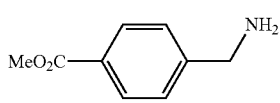

Preparation of ester 14: To a solution of 4-(aminomethyl) benzoic acid (1 eq.) in benzene (0.3 mL) and MeOH (0.3 mL) was added TMSCHN$_2$ (1.3 eqs.). The reaction mixture was stirred for 1.0 h, after which the reaction mixture was concentrated in vacuo. Ester 14 was used without further purification.

Preparation of triazine 15: To a solution of cyanuric chloride (1.14 eqs.) and $^t$ butyl 4-aminobenzoate (1.0 eq.) in THF (81 mL) was added $^i$Pr$_2$NEt (1.1 eqs.). The reaction mixture was stirred at ambient temperature for 1 hour. The reaction mixture was partitioned between water and EtOAc. The aqueous layer was extracted with EtOAc (3×), and the combined organics were dried over Na$_2$SO$_4$, filtered and concentrated in vacuo. The residue was used without further purification.

To a solution of the residue (1.0 eq.) and 4-benzyloxyaniline.HCl (1.1 eqs.) in THF (52 mL) was added $^i$Pr$_2$NEt (3.0 eqs). The reaction mixture was warmed to 50° C. and stirred overnight. The reaction mixture was cooled to ambient temperature and partitioned between water and EtOAc. The aqueous layer was extracted with EtOAc (3×), and the combined organics were dried over Na$_2$SO$_4$, filtered and concentrated in vacuo. The residue was used without further purification.

To a solution of the residue (1.0 eq.) and amine 1 (1.2 eqs.) in THF (1.5 mL) was added $^i$Pr$_2$NEt (3.0 eqs.). The reaction mixture was warmed to 65° C. and stirred overnight. The reaction mixture was concentrated in vacuo and the residue was purified via column chromatography over silica gel (2:1/hexanes:EtOAc →98:2/CH$_2$Cl$_2$:MeOH). The obtained residue (0.116 g, 78% yield over 3 steps) was used without further purification.

The residue (1.0 eq.) was dissolved in TFA (1.0 mL) and DMS (1.0 mL). The reaction mixture was warmed to 50° C. and stirred overnight. The reaction mixture was concentrated in vacuo and the residue used without further purification.

To a mixture of the residue (1.0 eq.), amine 14 (1.1 eqs.), EDAC.HCl (1.2 eqs.) and anhydrous HOBT (1.2 eqs.) was added DMF (1 mL). Subsequently, $^i$Pr$_2$NEt (3.0 eqs.) was added to the reaction mixture and the resulting solution stirred overnight. The reaction mixture was then concentrated in vacuo and the used without further purification.

A heterogeneous mixture of the residue (1 eq.) and LiOH (30 eqs.) in THF (0.3 mL), MeOH (0.3 mL) and H$_2$O (0.3 mL) was stirred at ambient temperature overnight. The reaction mixture was then acidified via addition of TFA and the reaction mixture concentrated in vacuo. The reaction mixture was concentrated in vacuo and the residue purified via reverse-phase HPLC. The obtained residue was then stirred in methanolic HCl (1.0 mL) overnight. Upon completion, the reaction mixture was concentrated in vacuo to yield triazine 15 (2.0 mg, 6.5% overall yield):MS (ESI): m/z=721 (M+H)$^+$; analytical HPLC (10-90% MeCN in H$_2$O, 20 mins, flow rate=1.0 mL/min.) R$_t$=14.42 mins (>90% pure).

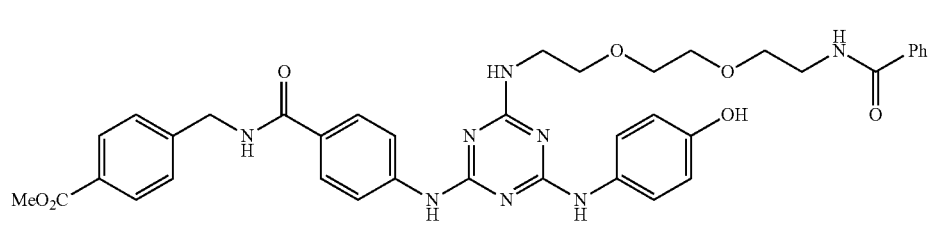

Scheme 10:
Generic Scheme:
  Scheme 10
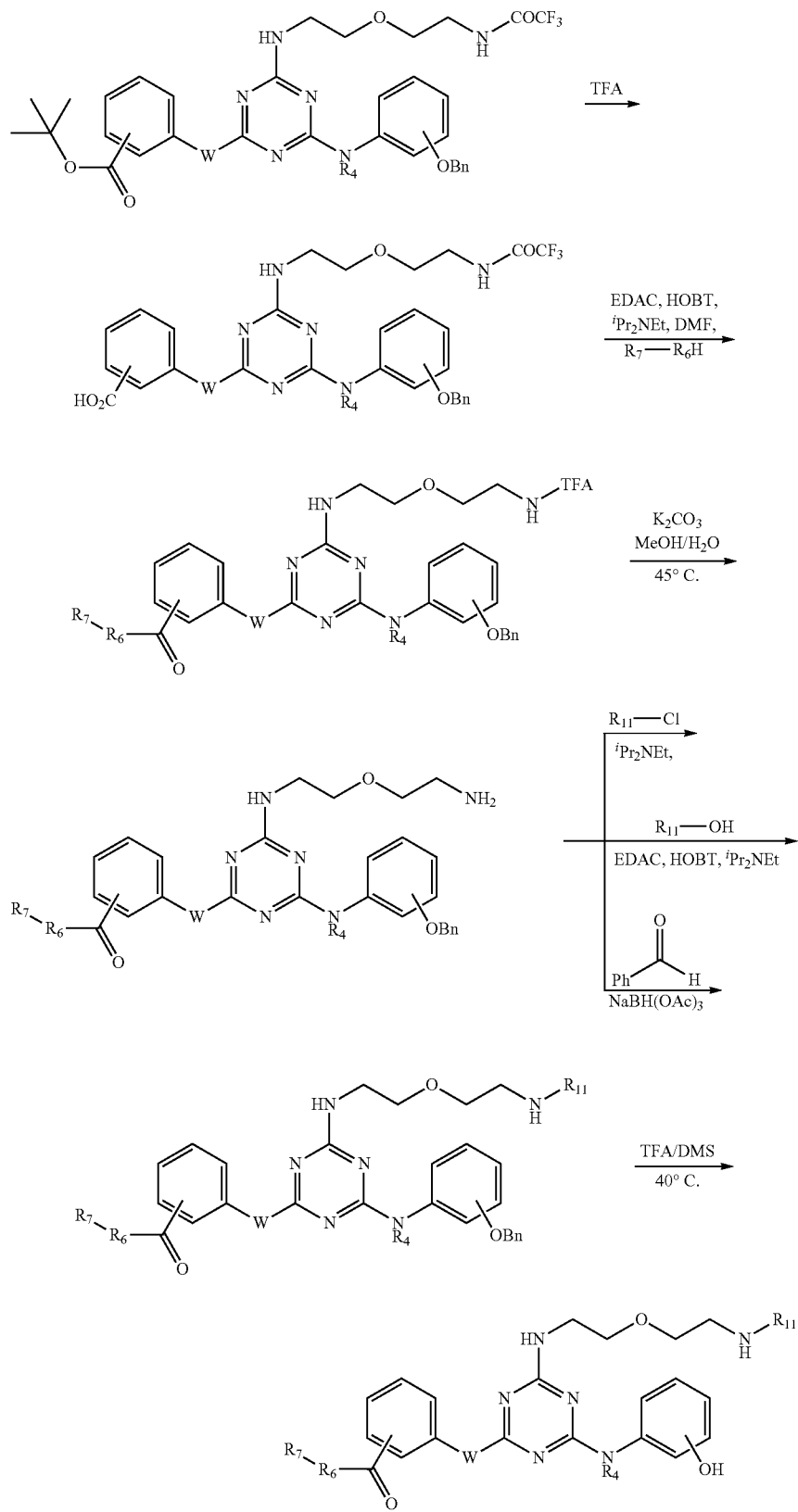

Experimental:

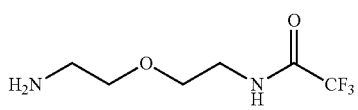

16

Preparation of amine 16: To a solution of bis(2-hydroxyethyl)ether (1.0 eqs) and $^i$Pr$_2$NEt (4.0 eqs.) in CH$_2$Cl$_2$ (24 mL) was added MsCl (2.2 eqs.). The reaction mixture was stirred at ambient temperature for 1 h. The reaction mixture was partitioned between water and CH$_2$Cl$_2$, the layers separated, and the aqueous layer extracted with CH$_2$Cl$_2$ (3×). The combined organics were dried over Na$_2$SO$_4$, filtered and concentrated in vacuo. The residue was used without further purification.

To a solution of the residue (1.0 eq.) and NaI (0.2 eqs.) in DMF (24 mL) was added NaN$_3$ (2.3 eqs.). The reaction mixture was warmed to 65° C. and stirred overnight. The reaction mixture was cooled to ambient temperature and partitioned between water and ether. The layers were separated and the aqueous extracted with ether (3×). The combined organics were dried over Na$_2$SO$_4$, filtered and concentrated in vacuo. The residue was used without further purification.

dichloromethane layers dried over Na$_2$SO$_4$, filtered and concentrated in vacuo. The obtained residue was used without further purification.

A solution of the residue (1.0 eq.) and Boc$_2$O (1.1 eqs.) in CH$_2$Cl$_2$ (70 mL) was added TEA (2.0 eqs.). The reaction mixture was stirred at ambient temperature for 2.0 hours. The reaction mixture was concentrated in vacuo. The residue was filtered over a plug of silica gel (2:1/hex:EtOAc) and the obtained residue (1.27 g, 38%) used with any further purification.

To a biphasic solution of the residue (1.0 eq.) in THF (23 mL) and water (6.6 mL) was added PMe$_3$ (5.0 eqs.). The reaction mixture was stirred for 2 hours. Subsequently, the reaction mixture was concentrated in vacuo and the residue dissolved in CH$_2$Cl$_2$ (53 mL). To the reaction mixture was added trifluoroacetic anhydride (1.2 eqs.) followed by TEA (2.0 eqs.). The reaction mixture was stirred at ambient temperature overnight. The mixture was then partitioned between water and CH$_2$Cl$_2$, the layers separated and the aqueous extracted with CH$_2$Cl$_2$ (3×). The combined organics were dried over Na$_2$SO$_4$, filtered and concentrated in vacuo. The residue was used without any further purification.

To a solution of the residue (1.0 eq.) in EtOAc (40 mL) was added concentrated HCl (13.6 mL). The reaction mixture was stirred at ambient temperature for 1 hour. The reaction mixture was then concentrated in vacuo and the obtained amine 16 was used without any further purification.

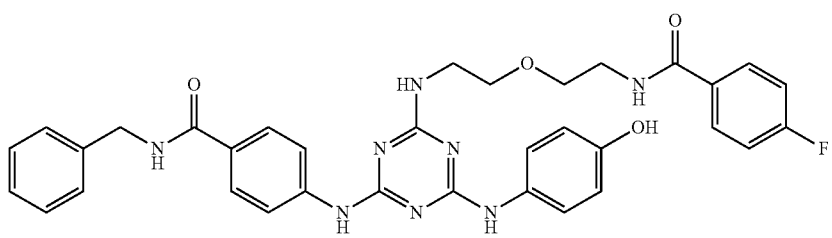

17a

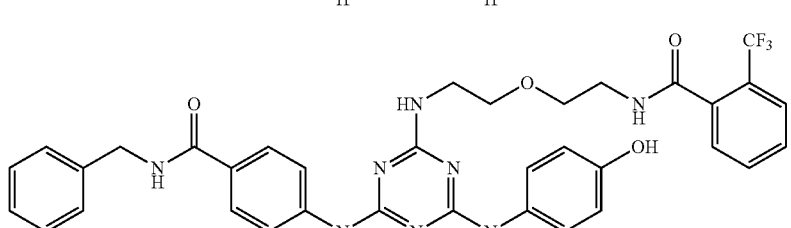

17b

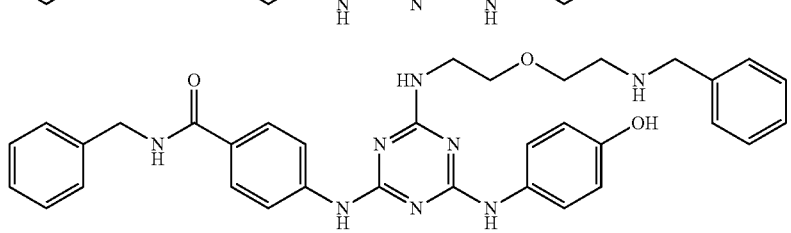

17c

To a solution of the residue (1.0 eq.) in THF (0.6 mL), ether (3 mL) and 1.0 M HCl (3 mL, aqueous) was added PPh$_3$ (1.05 eqs.). The reaction mixture was stirred at ambient temperature for 60 hours. Subsequently, the organics were removed from the reaction mixture in vacuo. Diethyl ether was added and the layers separated and the ethereal layer washed with 4.0 M HCl in water (50 mL). The combined aqueous layers were extracted with ether (2×) and the aqueous layer basicified to a pH~14 by addition of solid NaOH. The aqueous layer was then extracted with CH$_2$Cl$_2$ (3×) and the combined Preparation of triazines 17a, 17b and 17c: To a solution of cyanuric chloride (1.14 eqs.) and $^t$butyl 4-amino benzoate (1.0 eq.) in THF (51 mL) was added $^i$Pr$_2$NEt (2.0 eqs.). The reaction mixture was stirred at ambient temperature for 1 hour. To the solution was then added 4-benzyloxy aniline hydrochloride (1.3 eqs.) and $^i$Pr$_2$NEt (2.0 eqs.). The reaction mixture was warmed to 50° C. and stirred overnight. The reaction mixture was then cooled to ambient temperature and partitioned between EtOAc and water. The layers were separated and the aqueous extracted with EtOAc (3×). The combined organics were dried over Na₂SO₄, filtered and concentrated in vacuo. The residue was used without further purification.

To a solution of the residue (1.0 eq.) and amine 16 (1.07 eqs.) in THF (51 mL) was added $^i$Pr₂NEt (6.0 eqs.). The reaction mixture was warmed to 65° C. and stirred overnight. The reaction mixture was concentrated in vacuo and the residue filtered over a plug of silica gel (2:1/hexanes:EtOAc→98:2/CH₂Cl₂:MeOH). The organics from the 98:2/CH₂Cl₂:MeOH were collected and concentrated in vacuo. The obtained residue (1.69 g, 49% crude yield) was used without further purification.

The obtained residue (1.0 eq.) was dissolved in TFA (10 mL) and the solution was stirred for 1 hour at ambient temperature. The reaction mixture was concentrated in vacuo and the residue dissolved in DMF (25 mL). To the reaction mixture was added benzylamine (1.1 eqs.), EDAC.HCl (1.2 eqs.) and anhydrous HOBT (1.2 eqs.). Subsequently, $^i$Pr₂NEt (5.0 eqs.) was added to the reaction mixture and the resulting solution stirred overnight. The reaction mixture was concentrated in vacuo and the residue used without further purification.

To a solution of the residue (1.0 eq.) in MeOH (22 mL) and water (4.0 mL) was added K₂CO₃ (5.0 eqs.). The heterogeneous mixture was heated to 45° C. and stirred vigorously overnight. Subsequently, the reaction mixture was concentrated in vacuo and the residue used without further purification.

For 17a: To a mixture of the residue (1.0 eq.) and 4-fluorobenzoyl chloride (1.1 eqs) was added DMF (1.0 mL) followed by $^i$Pr₂NEt (2.0 eqs.). The reaction mixture was stirred overnight. Subsequently, the reaction mixture was concentrated in vacuo and the residue used without further purification. The residue (1.0 eq.) was dissolved in TFA (1 mL) and DMS (1 mL) and the obtained reaction mixture was warmed to 40° C. and stirred overnight. The reaction mixture was then concentrated in vacuo and the residue purified via reverse phase HPLC to yield triazine 17a (3.0 mg, 9.0% overall yield). MS (ESI): ink=637 (M+H)⁺; analytical HPLC (10-90% MeCN in H₂O, 20 mins, flow rate=1.0 mL/min.) R$_f$=14.57 mins (>90% pure).

For 17b: To a mixture of the residue (1.0 eq.), α, α, α-trifluoromethyl toluic acid (1.1 eqs.), EDAC.HCl (1.2 eqs.) and anhydrous HOBT (1.2 eqs.) was added DMF (1.0 mL). Subsequently, $^i$Pr₂NEt (2.0 eqs.) was added to the reaction mixture and the resulting solution stirred overnight. The reaction mixture was concentrated in vacuo and the residue used without further purification. The residue (1.0 eq.) was dissolved in TFA (1 mL) and DMS (1 mL) and the obtained reaction mixture was warmed to 40° C. and stirred overnight. The reaction mixture was then concentrated in vacuo and the residue purified via reverse phase HPLC to yield triazine 17b (3.4 mg, 10.7% overall yield). MS (ESI): m/z=687 (M+H)⁺; analytical HPLC (10-90% MeCN in H₂O, 20 mins, flow rate=1.0 mL/min.) R$_f$=14.83 mins (>90% pure).

For 17c: To a solution of the residue (1.0 eq.) in DCE/EtOH (2 mL, 1:1/v:v) was added benzaldehyde (1.2 eqs.) and AcOH (3 drops). The reaction mixture was stirred for 1 hour before sodium trisacetoxy borohydride (5.0 eqs.) was added. The reaction mixture was concentrated in vacuo and the residue used without further purification. The residue (1.0 eq.) was dissolved in TFA (1 mL) and DMS (1 mL) and the obtained reaction mixture was warmed to 40° C. and stirred overnight. The reaction mixture was then concentrated in vacuo and the residue purified via reverse phase HPLC to yield triazine 17c (2.4 mg, 8.0% overall yield). MS (ESI): m/z=605 (M+H)⁺; analytical HPLC (10-90% MeCN in H₂O, 20 mins, flow rate=1.0 mL/min.) R$_f$=12.85 mins (90% pure).

The following compounds were or could be made by the procedure described for triazines 17a, 17b or 17c:

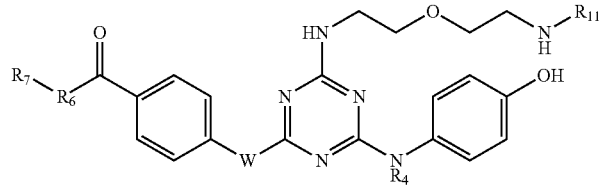

| Compound | W  | R4 | R6 | R7  | R11 | (M + H)⁺ |
|----------|----|----|----|-----|-----|----------|
| 17d      | NH | H  | NH | Bn- | (phenylglycine-derived acyl group) | 648 |
| 17e      | NH | H  | NH | Bn- | (phenylalanine-derived acyl group) | 662 |
| 17f      | NH | H  | NH | Bn- | (isonicotinoyl group) | 620 |

-continued

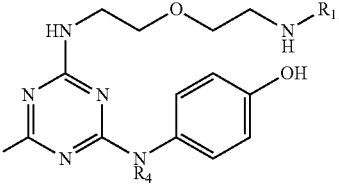

| Compound | W | R4 | R6 | R7 | R11 | (M + H)+ |
|---|---|---|---|---|---|---|
| 17g | NH | H | NH | Bn- | 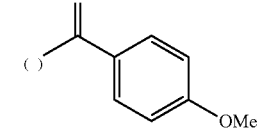 | 649 |
| 17h | NH | H | NH | Bn- | 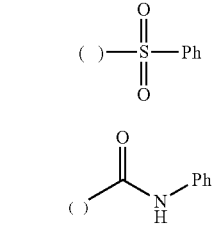 | 655 |
| 17i | NH | H | NH | Bn- | 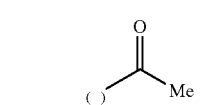 | 634 |
| 17j | NH | H | NH | Bn- | 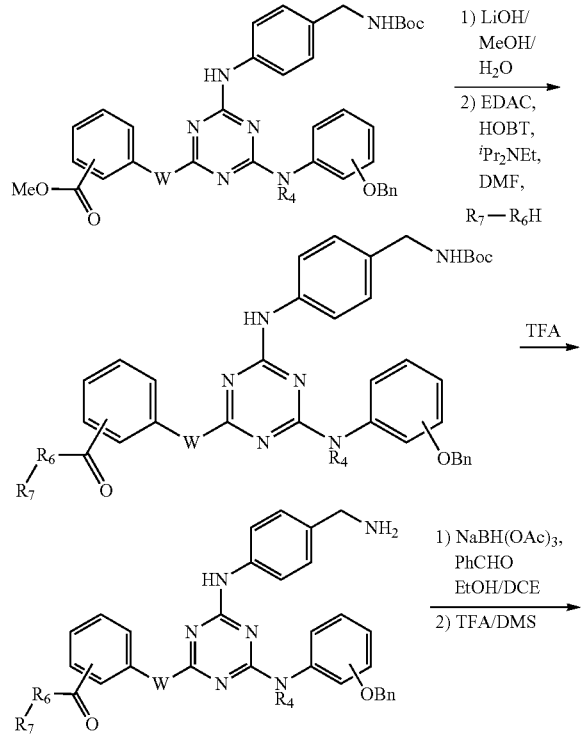 | 557 |

Scheme 11:
Generic Scheme:
Scheme 11

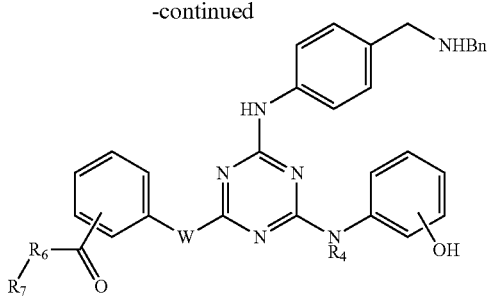

Experimental:

To a solution of cyanuric chloride (1.14 eqs.) and methyl 4-amino benzoate (1.0 eq.) in THF (3.0 mL) was added $^i$Pr$_2$NEt (4.0 eqs.). The reaction mixture was stirred at ambient temperature for 1 hour. To the solution was then added 4-[(N-Boc)aminomethyl]aniline (1.3 eqs.) and the reaction mixture warmed to 50° C. and stirred overnight. The reaction mixture was then cooled and partitioned between EtOAc and water. The layers were separated and the aqueous extracted with EtOAc (3×). The combined organics were dried over $Na_2SO_4$, filtered and concentrated in vacuo. The residue was used without further purification.

To a solution of the residue (1.0 eq.) and 4-benzyloxy aniline hydrochloride (2.0 eqs.) in THF (3.5 mL) was added $^iPr_2NEt$ (4.0 eqs). The reaction mixture was warmed to 65° C. and stirred overnight. The reaction mixture was concentrated in vacuo and the residue filtered over a plug of silica gel (2:1/hexanes:EtOAc→98:2/$CH_2Cl_2$:MeOH). The organics collected from the 98:2/$CH_2Cl_2$:MeOH elution were concentrated in vacuo and the obtained residue was used without further purification.

A heterogeneous mixture of the residue (1.0 eq.) and LiOH (30 eqs.) in THF (1.0 mL), MeOH (1.0 mL) and $H_2O$ (1.0 mL) was stirred at ambient temperature overnight. The reaction mixture was concentrated in vacuo and the residue dissolved in DMF (3.0 mL). To the solution was added 4-fluorobenzylamine (1.1 eqs.), EDAC.HCl (1.2 eqs.) and anhydrous HOBT (1.2 eqs.). Subsequently, $^iPr_2NEt$ (4.0 eqs.) was added to the reaction mixture and the resulting solution stirred overnight. The reaction mixture was concentrated in vacuo and the residue used without further purification.

The residue (1.0 eq.) was dissolved in TFA (3.5 mL) and the reaction mixture stirred at ambient temperature for 1 hour. The reaction mixture was concentrated in vacuo and the residue used without further purification.

To a solution of the residue (1.0 eq.) in DCE:EtOH (1.5 mL:1.5 mL) was added benzylaldehyde (1.2 eqs.). The reaction mixture was stirred at ambient temperature for 1 hour before sodium trisacetoxy borohydride (5.0 eqs.) was added. The reaction mixture was allowed to stir an additional 3 hours at ambient temperature before being concentrated in vacuo. The residue was then dissolved in TFA (1.5 mL) and DMS (1.5 mL) and stirred at 45° C. overnight. The reaction mixture was then concentrated in vacuo and the residue purified via reverse phase HPLC to yield triazine 18 (5.2 mg, 2.4% overall yield). MS (ESI): m/z=641 $(M+H)^+$; analytical HPLC (10-90% MeCN in $H_2O$, 20 mins, flow rate=1.0 mL/min.) $R_t$=14.33 mins (95% pure).

B. Inhibitory Properties of Compounds

MDCK cells stably transfected with rat PGT (Endo et al., 2002) were seeded at 15-20% confluence on 24-well plates. The day on which the cells were seeded was considered day 1. $PGE_2$ uptake experiments were conducted on day 4. All of the $PGE_2$ uptake experiments were conducted at room temperature. On day 4, cells were washed twice with Waymouth buffer (135 mM NaCl, 13 mM H-Hepes, 13 mM Na-Hepes, 2.5 mM $CaCl_2$, 1.2 mM $MgCl_2$, 0.8 mM $MgSO_4$, 5 mM KCl, and 28 mM D-glucose). Then 200 µL of Waymouth buffer containing [$^3H$]$PGE_2$ (purchased from Perkin Elmer) was added to each well. At the designed time, the uptake of [$^3H$]$PGE_2$ was stopped by aspiration of uptake buffer; this was followed by immediate washing twice with 500 µL of chilled Waymouth buffer. Cells were then lysed with 100 µL lysis buffer containing 0.25% SDS and 0.05 N NaOH. 1.5 mL of scintillation solution was added to each well, and intracellular [$^3H$]$PGE_2$ was counted by MicroBeta Counter.

For preliminary testing of the compounds, 20 µL of Waymouth buffer containing the compound was added to each well; this was immediately followed by the addition of 180 µL of Waymouth buffer containing [$^3H$]$PGE_2$. In each well, the total volume of uptake medium was 200 µL. Organic compounds were first dissolved in EtOH and then diluted in Waymouth buffer. The percent inhibition of [$^3H$]$PGE_2$ uptake by compounds was calculated as $[(uptake_{vehicle} - uptake_{inhibitor}) \div (uptake_{vehicle})] \times 100$.

To determine IC50 of each compound, 20 µof Waymouth buffer containing various concentrations of the compound was added to each well; this was immediately followed by the addition of 180 µL of Waymouth buffer containing [$^3H$]$PGE_2$. IC50 was calculated by fitting an equation of $y = m1 - m1*(m0/(m2+m0))$.

Results for the compounds are presented in Table 1, Inhibitory Activities of PGT Inhibitors. Abbreviations: Bn=benzyl (—$CH_2Ph$), Bz=benzoyl (—(C=O)Ph), Me=methyl (—$CH_3$), Ph=phenyl.

TABLE 1

Inhibitory Activities of PGT Inhibitors

| Cpd ID | Structure | Mol. Weight | IC$_{50}$ (nM) | Inh (% of Ctl) 0.1 µM | Inh (% of Ctl) 0.5 µM | Inh (% of Ctl) 1 µM | Inh (% of Ctl) 2.5 µM | Inh (% of Ctl) 5 µM | Inh (% of Ctl) 10 µM |
|---|---|---|---|---|---|---|---|---|---|
| T26A | 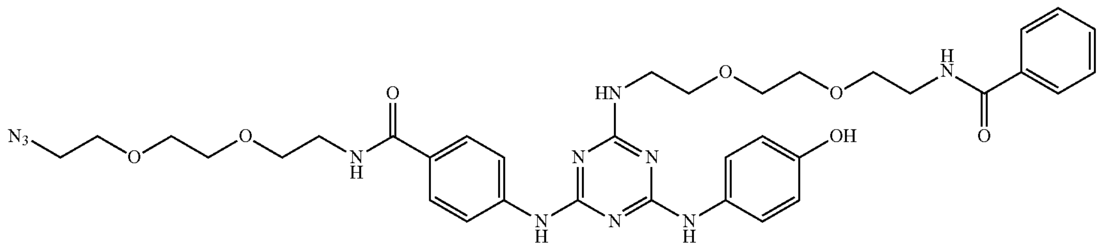 [SMILES: [N-]=[N+]=NCCOCCOCCNC(=O)c1ccc(Nc2nc(NCCOCCOCCNC(=O)c3ccccc3)nc(Nc3ccc(O)cc3)n2)cc1] | | 378 | 72.65 | | | | | |
| 1 | 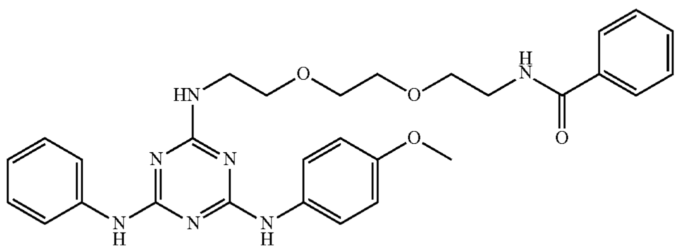 [SMILES: COc1ccc(Nc2nc(NCCOCCOCCNC(=O)c3ccccc3)nc(Nc3ccccc3)n2)cc1] | 543.62 | | | 9.6 | | | 8.5 | |
| 2 | 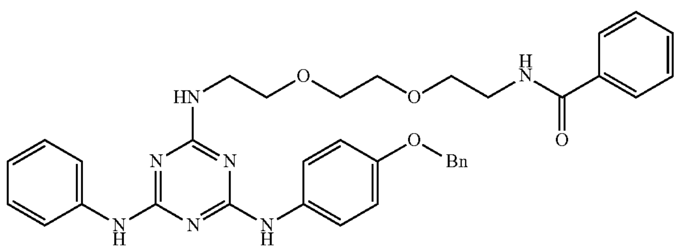 [SMILES: O=C(NCCOCCOCCNc1nc(Nc2ccccc2)nc(Nc2ccc(OCc3ccccc3)cc2)n1)c1ccccc1] | 619.71 | | | 1.6 | | | 6.5 | |

TABLE 1-continued
Inhibitory Activities of PGT Inhibitors
| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 3 | 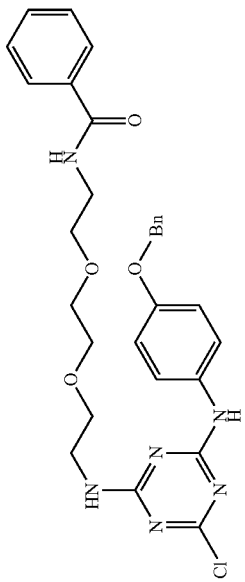 | 563.05 | | | 0.4 | | | 1.7 | |
| 4 | 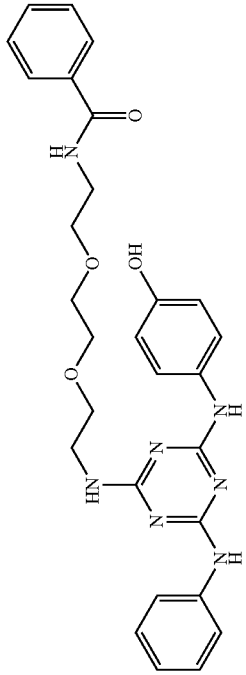 | 529.59 | 4850 | | 7.0 | 32.4 | | 67.6 | 81.5 |
| 5 | 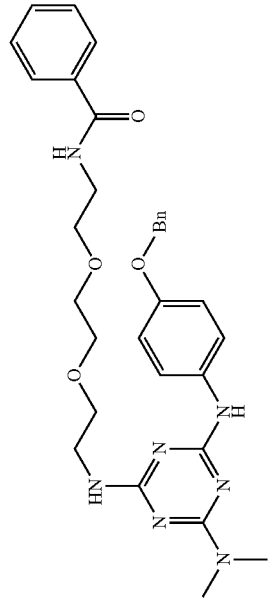 | 571.67 | | | 6.6 | | | 9.6 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 6 | 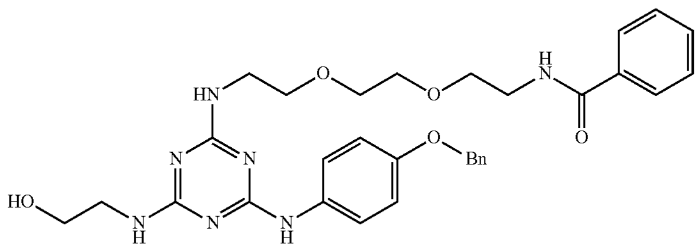 [SMILES: O=C(NCCOCCOCCNc1nc(NCCO)nc(Nc2ccc(OCc3ccccc3)cc2)n1)c1ccccc1] | 587.67 | | | 3.6 | | | 11.7 | |
| 7 | 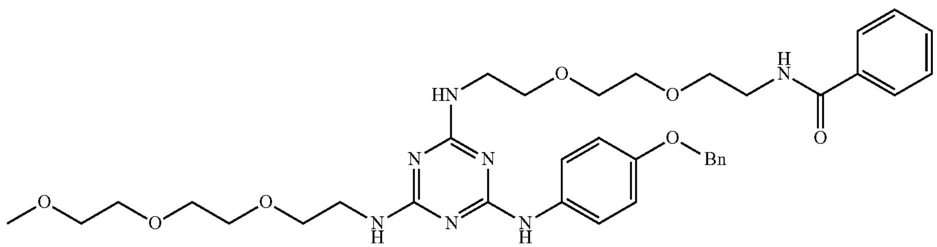 [SMILES: COCCOCCOCCNc1nc(NCCOCCOCCNC(=O)c2ccccc2)nc(Nc2ccc(OCc3ccccc3)cc2)n1] | 689.80 | | | 4.8 | | | 22.5 | |
| 8 | 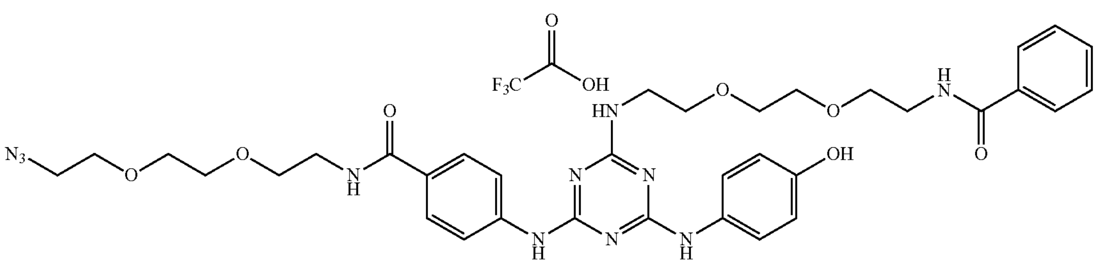 | 843.81 | 223.8 | | 52.3 | | | | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 9 | 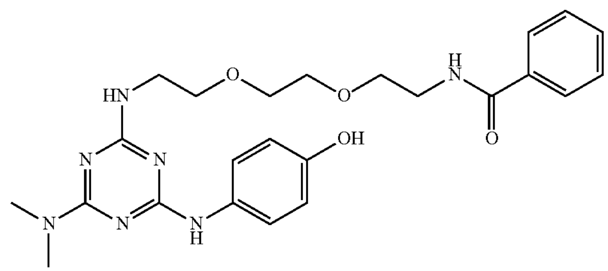 [SMILES: CN(C)c1nc(NCCOCCOCCNC(=O)c2ccccc2)nc(Nc2ccc(O)cc2)n1] | 481.55 | | | 1.3 | | | 18.8 | |
| 10 | 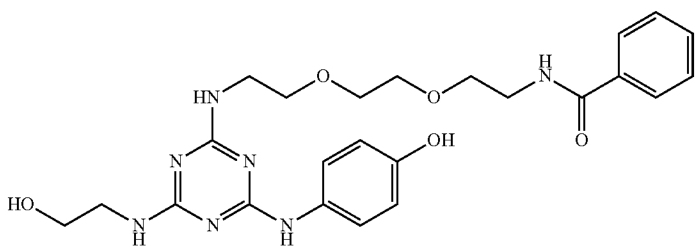 [SMILES: O=C(NCCOCCOCCNc1nc(NCCO)nc(Nc2ccc(O)cc2)n1)c1ccccc1] | 497.55 | | | 1.4 | | | 15.0 | |
| 11 | 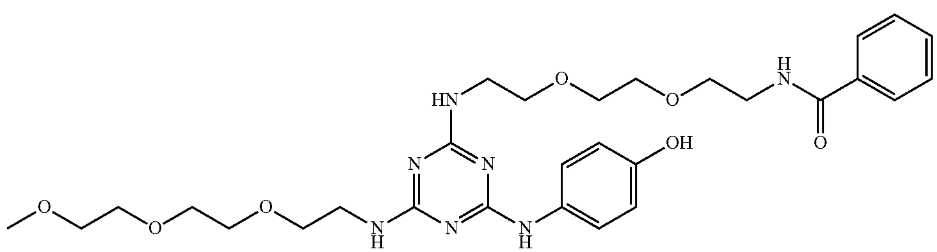 [SMILES: COCCOCCOCCNc1nc(NCCOCCOCCNC(=O)c2ccccc2)nc(Nc2ccc(O)cc2)n1] | 599.68 | | | 11.4 | | | 29.9 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 12 | 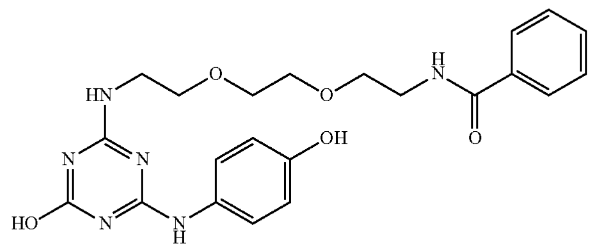 [SMILES: O=C(NCCOCCOCCNc1nc(O)nc(Nc2ccc(O)cc2)n1)c1ccccc1] | 568.05 | | | 2.8 | | | 4.7 | |
| 13 | 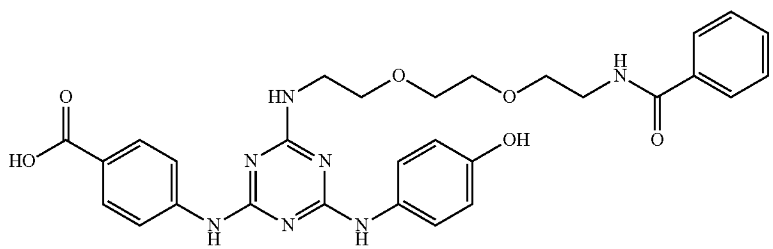 [SMILES: O=C(O)c1ccc(Nc2nc(NCCOCCOCCNC(=O)c3ccccc3)nc(Nc3ccc(O)cc3)n2)cc1] | 687.62 | | | 19.2 | | | 19.3 | |
| 14 | 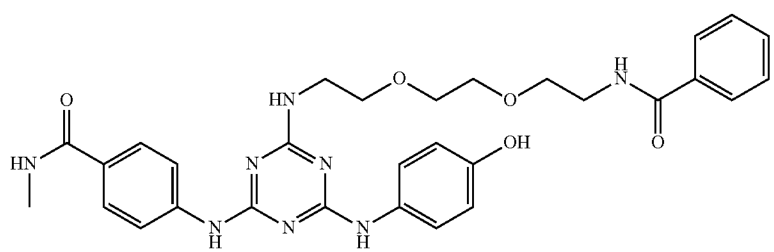 [SMILES: CNC(=O)c1ccc(Nc2nc(NCCOCCOCCNC(=O)c3ccccc3)nc(Nc3ccc(O)cc3)n2)cc1] | 700.66 | | | 10.6 | | | 35.9 | |

TABLE 1-continued

Inhibitory Activities of PGT Inhibitors

| Cpd ID | Structure | Mol. Weight | IC$_{50}$ (nM) | Inh (% of Ctl) 0.1 µM | Inh (% of Ctl) 0.5 µM | Inh (% of Ctl) 1 µM | Inh (% of Ctl) 2.5 µM | Inh (% of Ctl) 5 µM | Inh (% of Ctl) 10 µM |
|---|---|---|---|---|---|---|---|---|---|
| 15 | 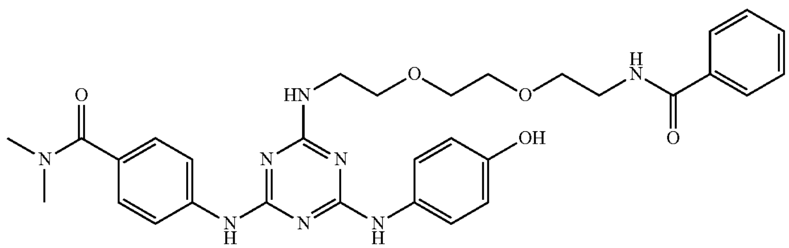 [SMILES: CN(C)C(=O)c1ccc(Nc2nc(NCCOCCOCCNC(=O)c3ccccc3)nc(Nc3ccc(O)cc3)n2)cc1] | 714.69 | | | 15.0 | | | 16.6 | |
| 16 | 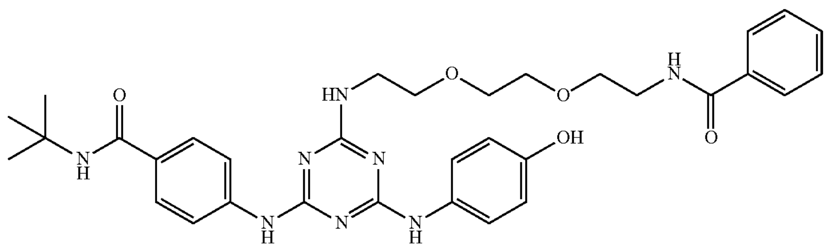 [SMILES: CC(C)(C)NC(=O)c1ccc(Nc2nc(NCCOCCOCCNC(=O)c3ccccc3)nc(Nc3ccc(O)cc3)n2)cc1] | 742.74 | 9770 | | 11.8 | | | 44.8 | |
| 17 | 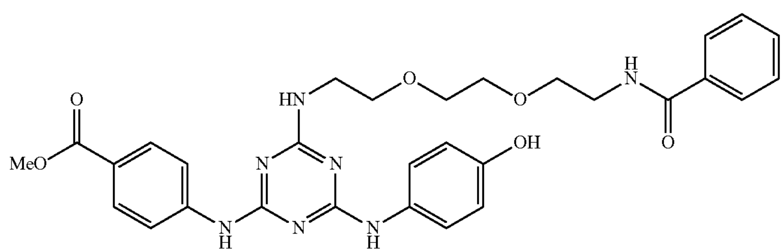 [SMILES: COC(=O)c1ccc(Nc2nc(NCCOCCOCCNC(=O)c3ccccc3)nc(Nc3ccc(O)cc3)n2)cc1] | 701.65 | 6570 | | 22.0 | | | 55.6 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 18 | 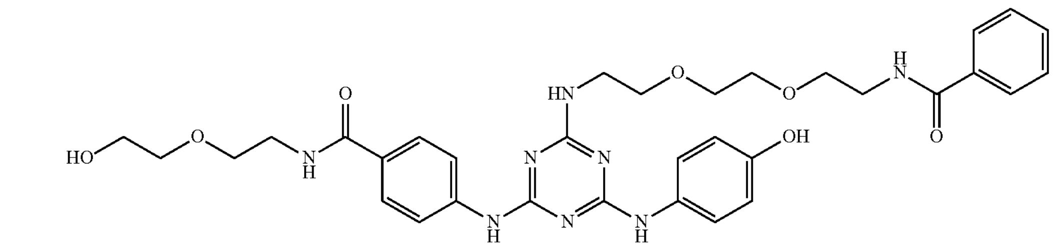 [SMILES: O=C(NCCOCCO)c1ccc(Nc2nc(NCCOCCOCCNC(=O)c3ccccc3)nc(Nc3ccc(O)cc3)n2)cc1] | 774.74 | | | 21.1 | | | 48.9 | |
| 19 | 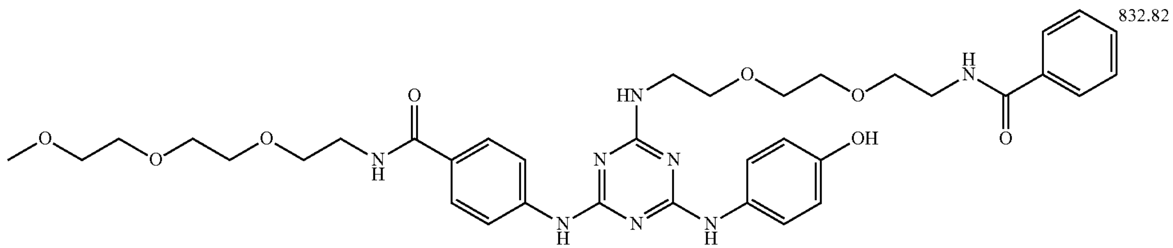 | 832.82 | | | 41.3 | | | 75.0 | |
| 20 | 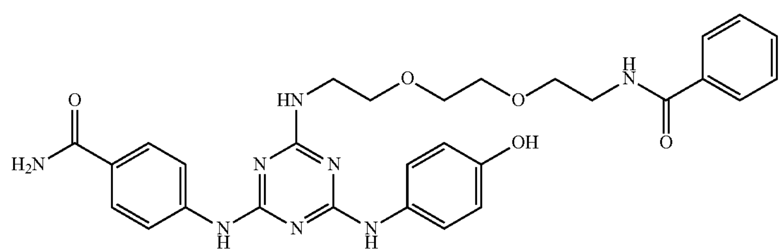 [SMILES: NC(=O)c1ccc(Nc2nc(NCCOCCOCCNC(=O)c3ccccc3)nc(Nc3ccc(O)cc3)n2)cc1] | 686.63 | | | 9.6 | | | 14.4 | |
| 21 | 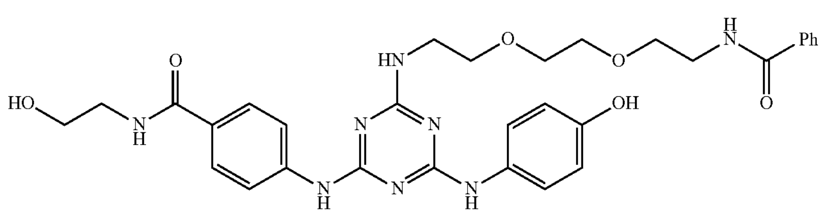 [SMILES: O=C(NCCO)c1ccc(Nc2nc(NCCOCCOCCNC(=O)c3ccccc3)nc(Nc3ccc(O)cc3)n2)cc1] | 730.69 | | | 15.7 | | | 68.2 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 22 | 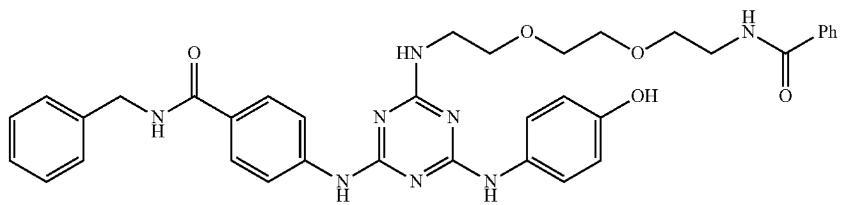 | 776.76 | 42.7 | | 62.4 | | | 88.1 | 95.5 |
| 23 | 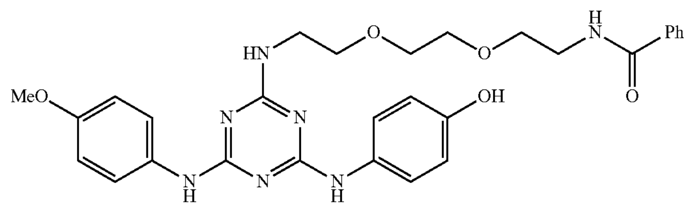 [SMILES: COc1ccc(Nc2nc(NCCOCCOCCNC(=O)c3ccccc3)nc(Nc3ccc(O)cc3)n2)cc1] | 673.64 | | | 14.4 | | | 38.4 | |
| 24 | 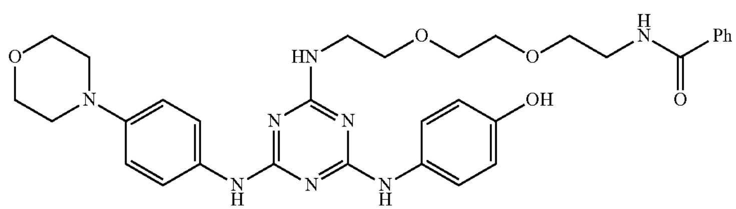 [SMILES: O=C(NCCOCCOCCNc1nc(Nc2ccc(O)cc2)nc(Nc2ccc(N3CCOCC3)cc2)n1)c1ccccc1] | 728.71 | | | 1.7 | | | 9.2 | |
| 25 | 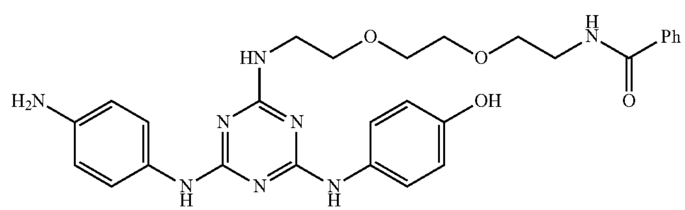 [SMILES: Nc1ccc(Nc2nc(NCCOCCOCCNC(=O)c3ccccc3)nc(Nc3ccc(O)cc3)n2)cc1] | 658.62 | | | 12.9 | | | 27.7 | |

TABLE 1-continued
Inhibitory Activities of PGT Inhibitors
| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 26 | 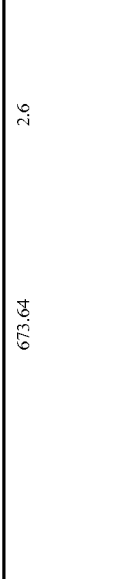 | 673.64 | | | 2.6 | | | 35.2 | |
| 27 | 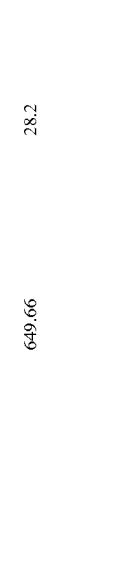 | 649.66 | | | 28.2 | | | 53.8 | |
| 28 | 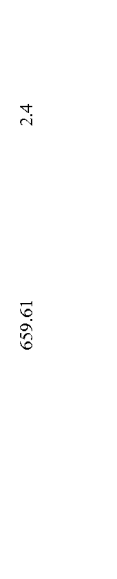 | 659.61 | | | 2.4 | | | 56.5 | |
| 29 | 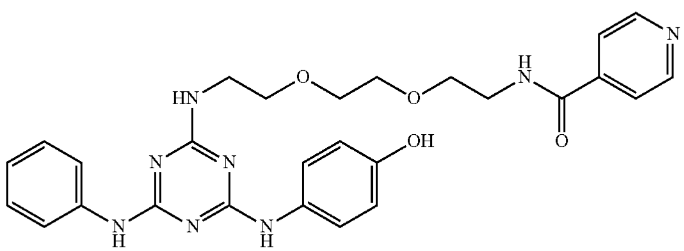 [SMILES: O=C(NCCOCCOCCNc1nc(Nc2ccccc2)nc(Nc2ccc(O)cc2)n1)c1ccncc1] | 758.62 | | | | 15.9 | | | 49.6 |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 30 | 4-F-C6H4-C(O)NH-CH2CH2-O-CH2CH2-O-[triazine(NHPh)(NH-C6H4-OH)] | 661.6 | | | | 26.1 | | | 78.25 |
| 31 | 4-Br-C6H4-C(O)NH-CH2CH2-O-CH2CH2-O-[triazine(NHPh)(NH-C6H4-OH)] | 722.51 | | | | 12.2 | | | 69.2 |
| 32 | 4-MeO-C6H4-C(O)NH-CH2CH2-O-CH2CH2-O-[triazine(NHPh)(NH-C6H4-OH)] | 673.64 | | | | 29.0 | | | 71.0 |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 33 | 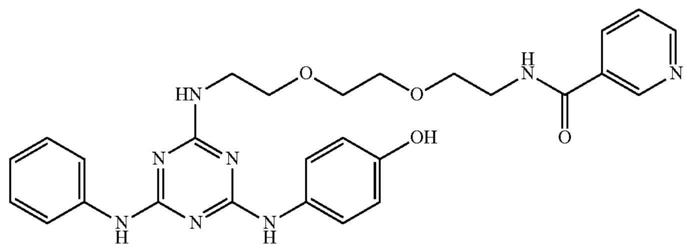 [SMILES: O=C(NCCOCCOCCNc1nc(Nc2ccccc2)nc(Nc2ccc(O)cc2)n1)c1cccnc1] | 758.62 | | | | 13.2 | | | 54.6 |
| 34 | 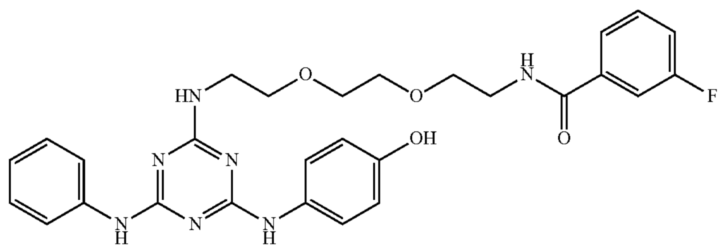 [SMILES: O=C(NCCOCCOCCNc1nc(Nc2ccccc2)nc(Nc2ccc(O)cc2)n1)c1cccc(F)c1] | 661.6 | | | | 25.8 | | | 81 |
| 35 | 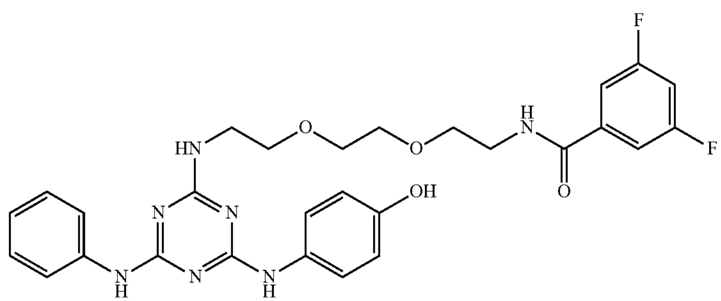 [SMILES: O=C(NCCOCCOCCNc1nc(Nc2ccccc2)nc(Nc2ccc(O)cc2)n1)c1cc(F)cc(F)c1] | 679.59 | | | | 20.4 | | | 75.6 |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 36 | 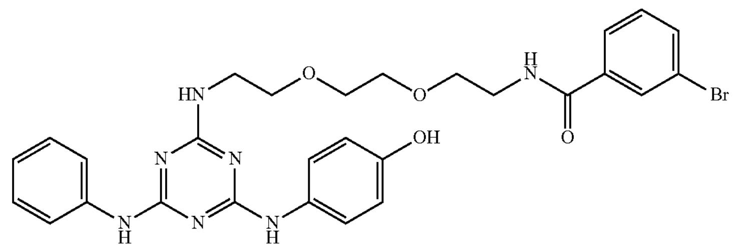 [SMILES: O=C(NCCOCCOCCNc1nc(Nc2ccccc2)nc(Nc2ccc(O)cc2)n1)c1cccc(Br)c1] | 722.51 | | | | 30.3 | | | 81.1 |
| 37 | 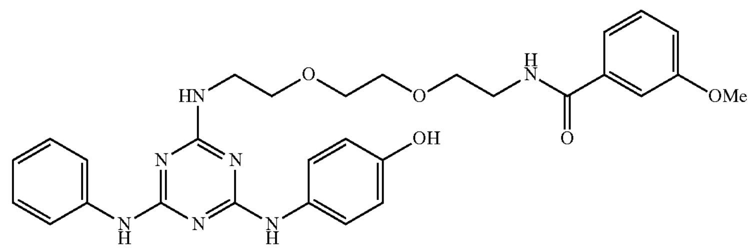 [SMILES: COc1cccc(C(=O)NCCOCCOCCNc2nc(Nc3ccccc3)nc(Nc3ccc(O)cc3)n2)c1] | 673.64 | | | | 32.4 | | | 79.0 |
| 38 | 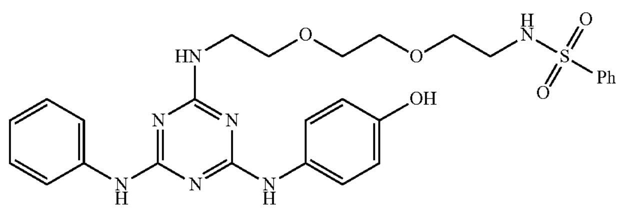 [SMILES: O=S(=O)(NCCOCCOCCNc1nc(Nc2ccccc2)nc(Nc2ccc(O)cc2)n1)c1ccccc1] | 679.66 | | | | 22.8 | | | 63.0 |
| 39 | 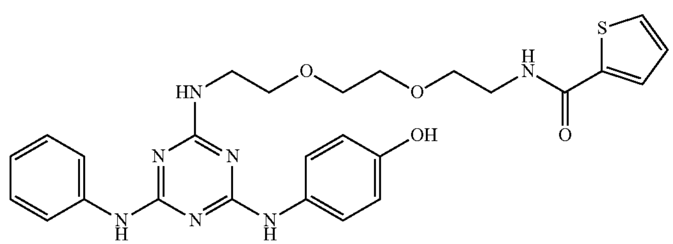 [SMILES: O=C(NCCOCCOCCNc1nc(Nc2ccccc2)nc(Nc2ccc(O)cc2)n1)c1cccs1] | 649.64 | | | | 42.9 | | | 86.2 |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 40 | 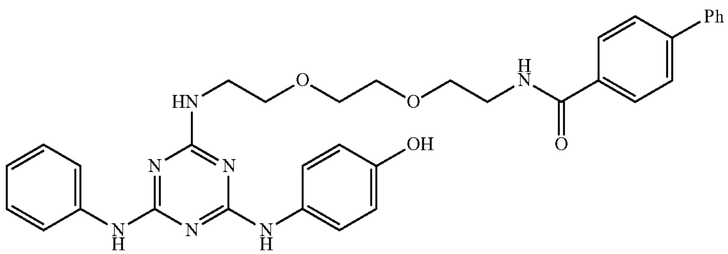 [SMILES: O=C(NCCOCCOCCNc1nc(Nc2ccccc2)nc(Nc2ccc(O)cc2)n1)c1ccc(-c2ccccc2)cc1] | 719.71 | | | | 16.3 | | | 46.9 |
| 41 | 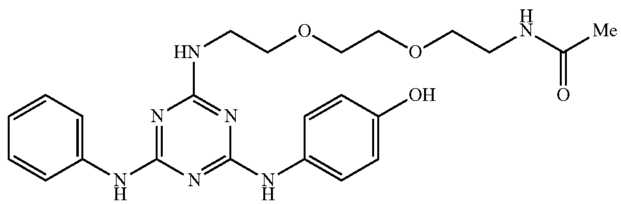 [SMILES: CC(=O)NCCOCCOCCNc1nc(Nc2ccccc2)nc(Nc2ccc(O)cc2)n1] | 581.54 | | | | 0.3 | | | 6.6 |
| 42 | 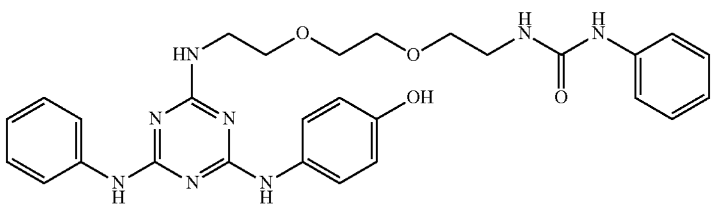 [SMILES: O=C(NCCOCCOCCNc1nc(Nc2ccccc2)nc(Nc2ccc(O)cc2)n1)Nc1ccccc1] | 658.62 | | | | 22.8 | | | 57.6 |
| 43 | 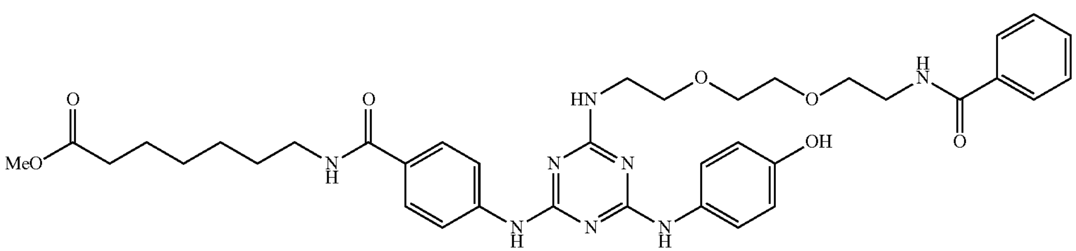 [SMILES: COC(=O)CCCCCCNC(=O)c1ccc(Nc2nc(NCCOCCOCCNC(=O)c3ccccc3)nc(Nc3ccc(O)cc3)n2)cc1] | 828.83 | 1300 | | | 34.8 | | | 84.1 |

TABLE 1-continued

Inhibitory Activities of PGT Inhibitors

| Cpd ID | Structure | Mol. Weight | IC$_{50}$ (nM) | Inh (% of Ctl) 0.1 µM | Inh (% of Ctl) 0.5 µM | Inh (% of Ctl) 1 µM | Inh (% of Ctl) 2.5 µM | Inh (% of Ctl) 5 µM | Inh (% of Ctl) 10 µM |
|---|---|---|---|---|---|---|---|---|---|
| 44 | 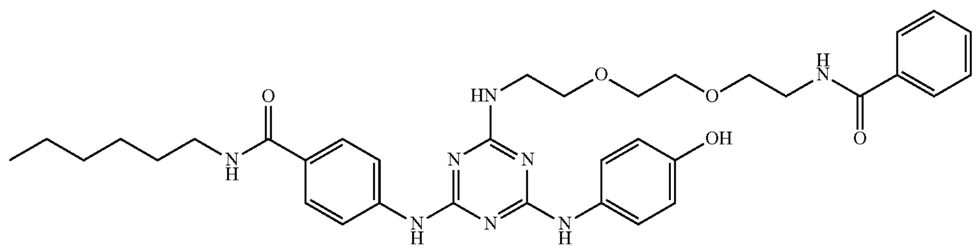 [SMILES: CCCCCCNC(=O)c1ccc(Nc2nc(NCCOCCOCCNC(=O)c3ccccc3)nc(Nc3ccc(O)cc3)n2)cc1] | 770.79 | 760 | | | 65.0 | | | 77.5 |
| 45 | 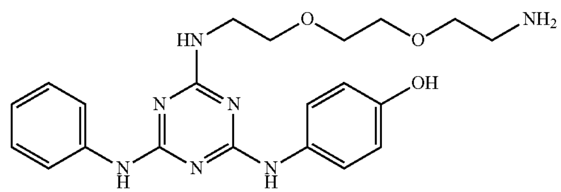 [SMILES: NCCOCCOCCNc1nc(Nc2ccccc2)nc(Nc2ccc(O)cc2)n1] | 653.52 | | | | 5.0 | | | 12.9 |
| 46 | 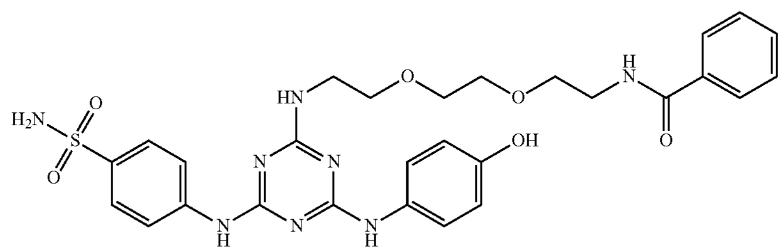 [SMILES: NS(=O)(=O)c1ccc(Nc2nc(NCCOCCOCCNC(=O)c3ccccc3)nc(Nc3ccc(O)cc3)n2)cc1] | 722.69 | | | | 4.1 | | | 32.4 |
| 47 | 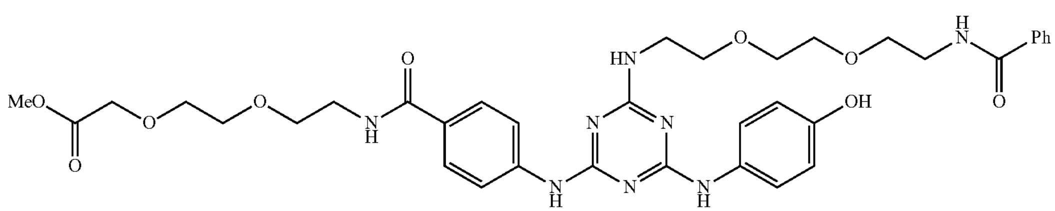 [SMILES: COC(=O)COCCOCCNC(=O)c1ccc(Nc2nc(NCCOCCOCCNC(=O)c3ccccc3)nc(Nc3ccc(O)cc3)n2)cc1] | 846.8 | | | | 22.6 | | | 76.5 |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 48 | 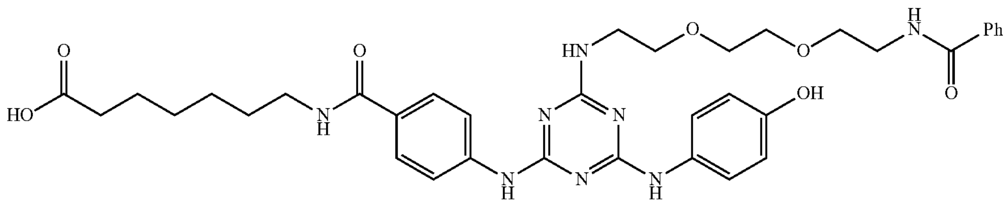 [SMILES: O=C(O)CCCCCCNC(=O)c1ccc(Nc2nc(NCCOCCOCCNC(=O)c3ccccc3)nc(Nc3ccc(O)cc3)n2)cc1] | 700.78 | | | | 14.2 | | | 62.8 |
| 49 | 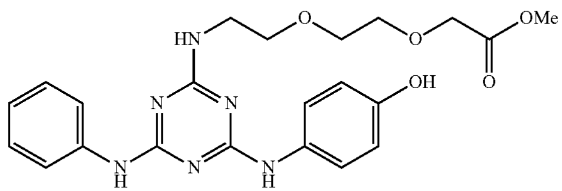 [SMILES: COC(=O)COCCOCCNc1nc(Nc2ccccc2)nc(Nc2ccc(O)cc2)n1] | 568.5 | | | | 1.7 | | | 12.5 |
| 50 | 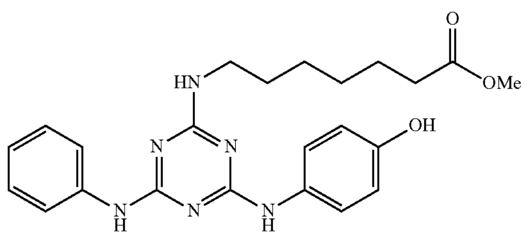 [SMILES: COC(=O)CCCCCCNc1nc(Nc2ccccc2)nc(Nc2ccc(O)cc2)n1] | 550.53 | | | | 9.3 | | | 15.1 |
| 51 | 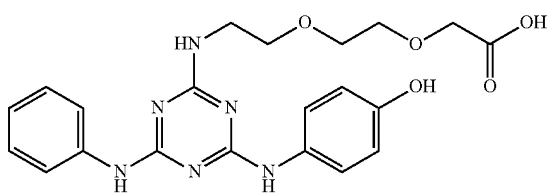 [SMILES: O=C(O)COCCOCCNc1nc(Nc2ccccc2)nc(Nc2ccc(O)cc2)n1] | 440.45 | | | | 17.4 | | | 29.8 |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 52 | 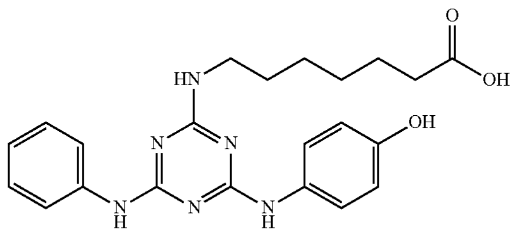 [SMILES: O=C(O)CCCCCCNc1nc(Nc2ccccc2)nc(Nc2ccc(O)cc2)n1] | 422.48 | | | | 0.1 | | | 1.8 |
| 53 | 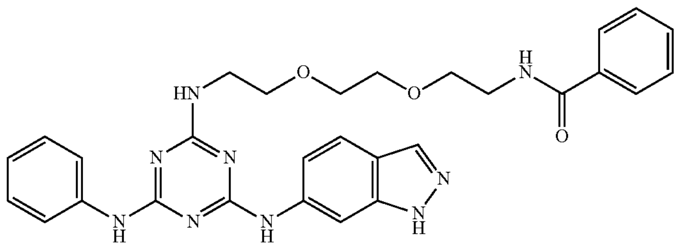 [SMILES: O=C(NCCOCCOCCNc1nc(Nc2ccccc2)nc(Nc2ccc3cn[nH]c3c2)n1)c1ccccc1] | 667.63 | 4040 | | | 65.2 | | 83.4 | 86.4 |
| 54 | 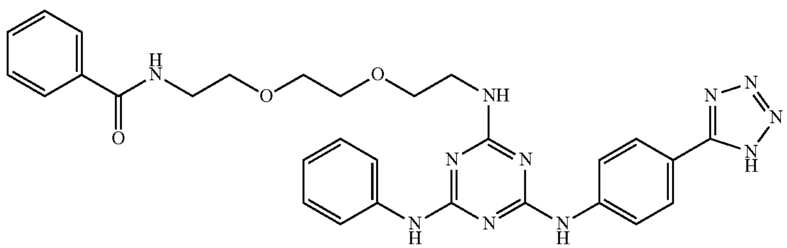 [SMILES: O=C(NCCOCCOCCNc1nc(Nc2ccccc2)nc(Nc2ccc(-c3nnn[nH]3)cc2)n1)c1ccccc1] | 695.65 | | | | 33.7 | | | 52.2 |
| 55 | 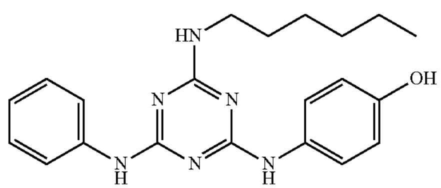 [SMILES: CCCCCCNc1nc(Nc2ccccc2)nc(Nc2ccc(O)cc2)n1] | 492.49 | | | | 12.7 | | | 26.1 |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 56 | 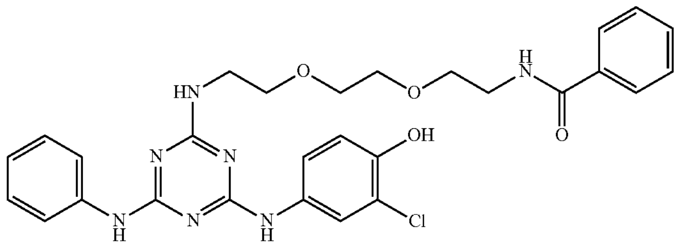 [SMILES: O=C(NCCOCCOCCNc1nc(Nc2ccccc2)nc(Nc2ccc(O)c(Cl)c2)n1)c1ccccc1] | 678.06 | | | | 38.0 | | | 80.5 |
| 57 | 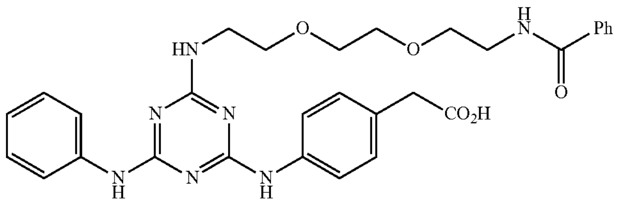 [SMILES: O=C(O)Cc1ccc(Nc2nc(NCCOCCOCCNC(=O)c3ccccc3)nc(Nc3ccccc3)n2)cc1] | 571.63 | 5570 | | | 27.4 | | 29.5 | 56.6 |
| 58 | 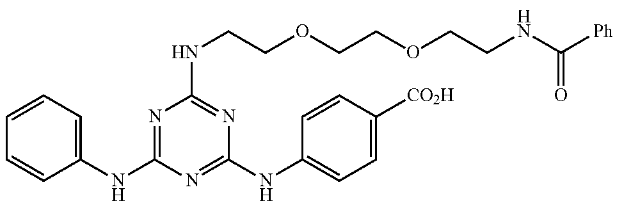 [SMILES: O=C(O)c1ccc(Nc2nc(NCCOCCOCCNC(=O)c3ccccc3)nc(Nc3ccccc3)n2)cc1] | 557.6 | | | | 16.25 | | 41.0 | 52.5 |
| 59 | 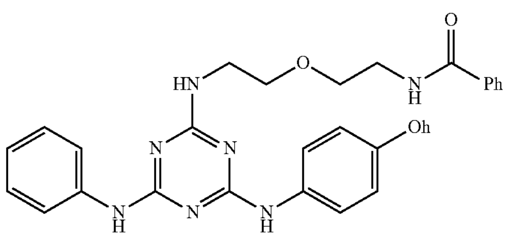 | 599.56 | 2460 | | | 36.8 | | | 75.8 |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 60 | 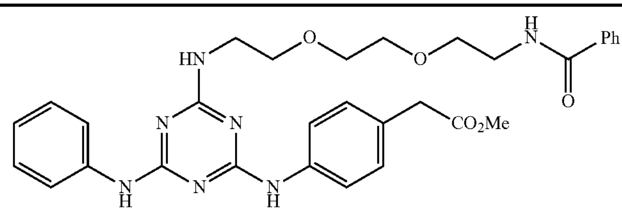 | 699.67 | | | | 7.2 | | | 34.5 |
| 61 | 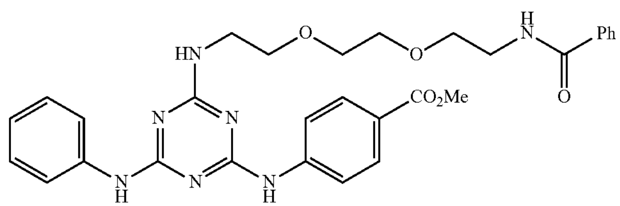 [SMILES: COC(=O)c1ccc(Nc2nc(NCCOCCOCCNC(=O)c3ccccc3)nc(Nc3ccccc3)n2)cc1] | 685.65 | | | | 7.5 | | | 46.1 |
| 62 | 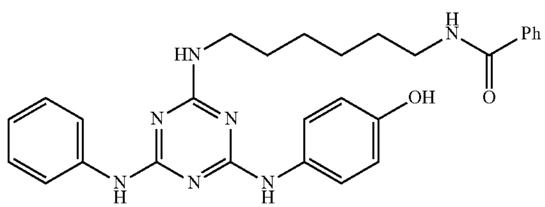 [SMILES: O=C(NCCCCCCNc1nc(Nc2ccccc2)nc(Nc2ccc(O)cc2)n1)c1ccccc1] | 611.61 | | | | 20.4 | | | 50.1 |
| 63 | 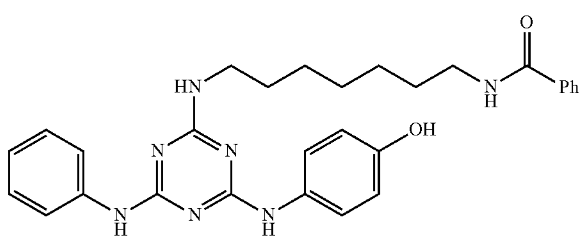 [SMILES: O=C(NCCCCCCCNc1nc(Nc2ccccc2)nc(Nc2ccc(O)cc2)n1)c1ccccc1] | 625.75 | | | | 11.0 | | | 44.1 |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 64 | 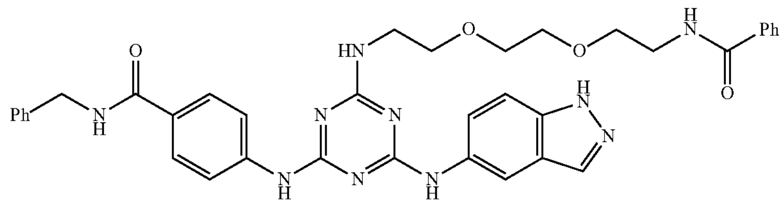 [SMILES: O=C(NCCOCCOCCNc1nc(Nc2ccc(C(=O)NCc3ccccc3)cc2)nc(Nc2ccc3[nH]ncc3c2)n1)c1ccccc1] | 800.78 | 115 | | 15.5 | 71.6 | | 77.2 | 90.2 |
| 65 | 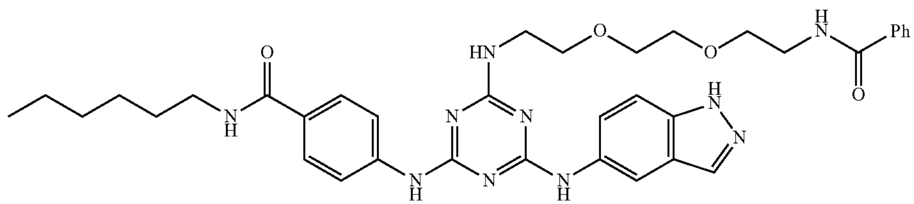 [SMILES: CCCCCCNC(=O)c1ccc(Nc2nc(NCCOCCOCCNC(=O)c3ccccc3)nc(Nc3ccc4[nH]ncc4c3)n2)cc1] | 794.82 | 1380 | | 18.4 | 66.4 | | 84.0 | 90.0 |
| 66 | 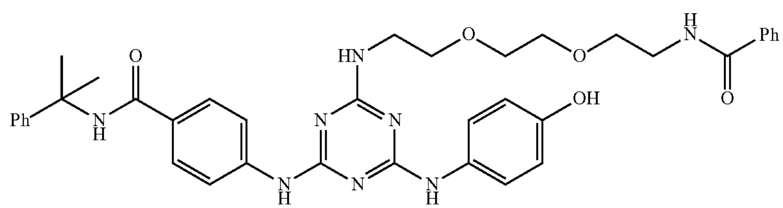 [SMILES: CC(C)(NC(=O)c1ccc(Nc2nc(NCCOCCOCCNC(=O)c3ccccc3)nc(Nc3ccc(O)cc3)n2)cc1)c1ccccc1] | 804.81 | | | 10.9 | | | 64.4 | |
| 67 | 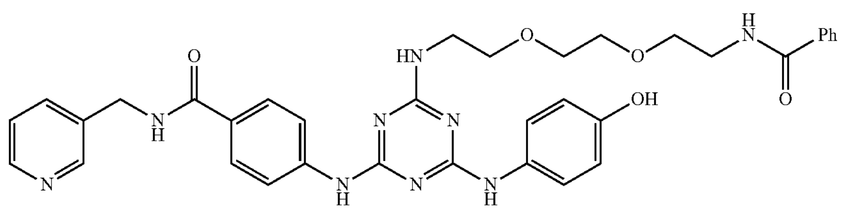 [SMILES: O=C(NCCOCCOCCNc1nc(Nc2ccc(O)cc2)nc(Nc2ccc(C(=O)NCc3cccnc3)cc2)n1)c1ccccc1] | 891.77 | | | 13.4 | | | 76.1 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 68 | 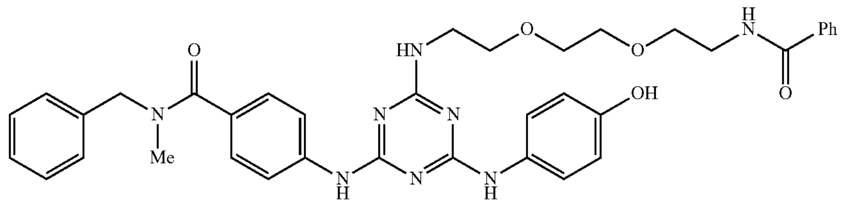 [SMILES: CN(Cc1ccccc1)C(=O)c1ccc(Nc2nc(NCCOCCOCCNC(=O)c3ccccc3)nc(Nc3ccc(O)cc3)n2)cc1] | 790.78 | | | 15.0 | | | 70.8 | |
| 69 | 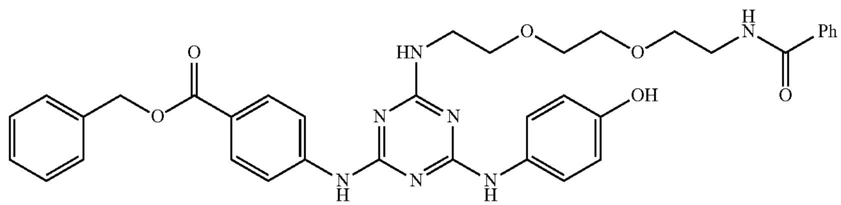 [SMILES: O=C(NCCOCCOCCNc1nc(Nc2ccc(O)cc2)nc(Nc2ccc(C(=O)OCc3ccccc3)cc2)n1)c1ccccc1] | 777.74 | 890 | | 24.9 | | | 83.2 | |
| 70 | 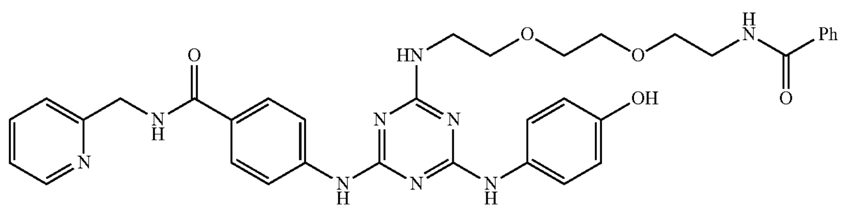 [SMILES: O=C(NCCOCCOCCNc1nc(Nc2ccc(O)cc2)nc(Nc2ccc(C(=O)NCc3ccccn3)cc2)n1)c1ccccc1] | 891.77 | 1050 | | 21.2 | | | 84.0 | |
| 71 | 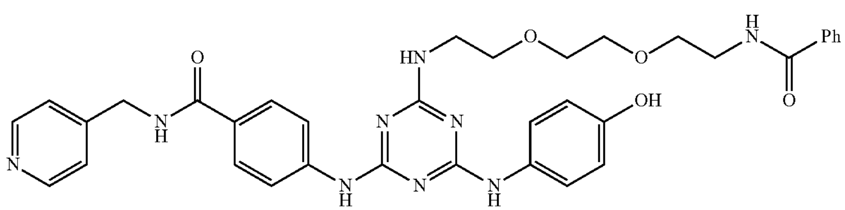 [SMILES: O=C(NCCOCCOCCNc1nc(Nc2ccc(O)cc2)nc(Nc2ccc(C(=O)NCc3ccncc3)cc2)n1)c1ccccc1] | 891.77 | | | 16.7 | | | 78.4 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 72 | 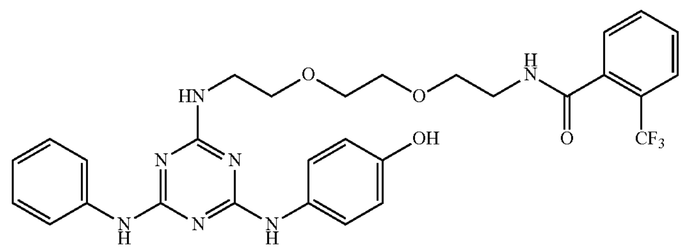 [SMILES: O=C(NCCOCCOCCNc1nc(Nc2ccccc2)nc(Nc2ccc(O)cc2)n1)c1ccccc1C(F)(F)F] | 711.61 | | | | 19.7 | | 66.1 | 75.3 |
| 73 | 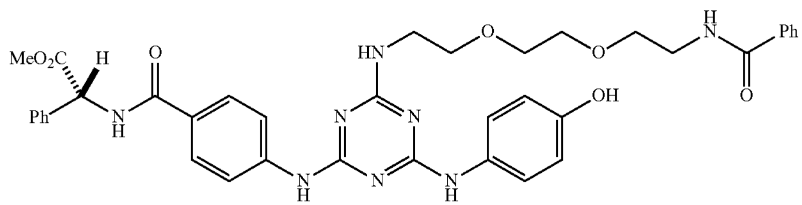 [SMILES: COC(=O)[C@H](NC(=O)c1ccc(Nc2nc(NCCOCCOCCNC(=O)c3ccccc3)nc(Nc3ccc(O)cc3)n2)cc1)c1ccccc1] | 834.79 | | 45.0 | 51.6 | | 38.9 | 75.3 | |
| 74 | 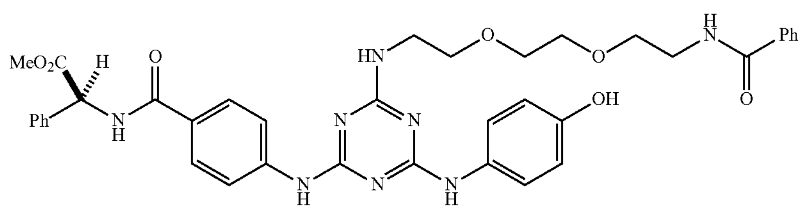 [SMILES: COC(=O)[C@@H](NC(=O)c1ccc(Nc2nc(NCCOCCOCCNC(=O)c3ccccc3)nc(Nc3ccc(O)cc3)n2)cc1)c1ccccc1] | 834.79 | | | | | 56.9 | 82.0 | |
| 75 | 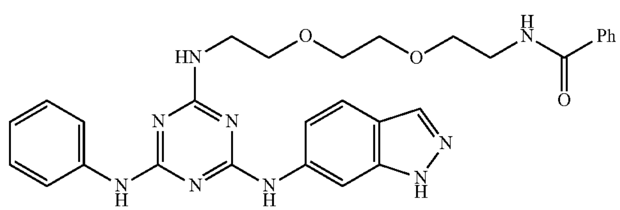 [SMILES: O=C(NCCOCCOCCNc1nc(Nc2ccccc2)nc(Nc2ccc3cn[nH]c3c2)n1)c1ccccc1] | 667.63 | | | | 8.4 | | 10.1 | 12.5 |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 76 | 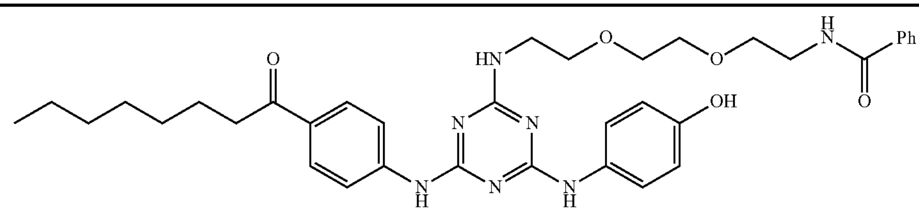 | 769.81 | | | 13.5 | | 35.9 | 70.5 | |
| 77 | 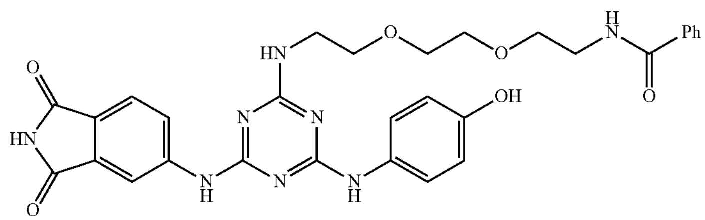 [SMILES: O=C(NCCOCCOCCNc1nc(Nc2ccc(O)cc2)nc(Nc2ccc3c(c2)C(=O)NC3=O)n1)c1ccccc1] | 712.63 | | | 1.8 | | 4.3 | 23.2 | |
| 78 | 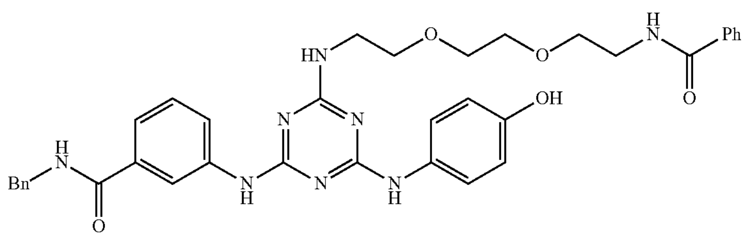 [SMILES: O=C(NCCOCCOCCNc1nc(Nc2ccc(O)cc2)nc(Nc2cccc(C(=O)NCc3ccccc3)c2)n1)c1ccccc1] | 776.76 | | | 15.5 | | 24.5 | 83.2 | |
| 79 | 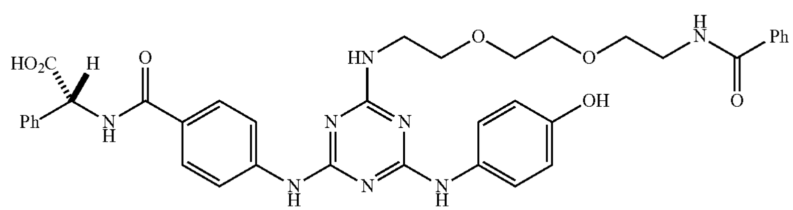 [SMILES: O=C(NCCOCCOCCNc1nc(Nc2ccc(O)cc2)nc(Nc2ccc(C(=O)N[C@@H](C(=O)O)c3ccccc3)cc2)n1)c1ccccc1] | 706.75 | | | 5.4 | | 29.2 | 54.9 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 80 | 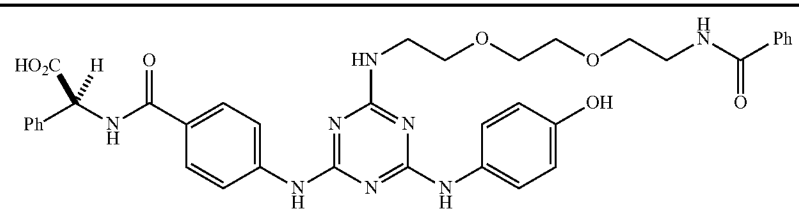 | 706.75 | | | 0.7 | | 21.8 | 57.2 | |
| 81 | 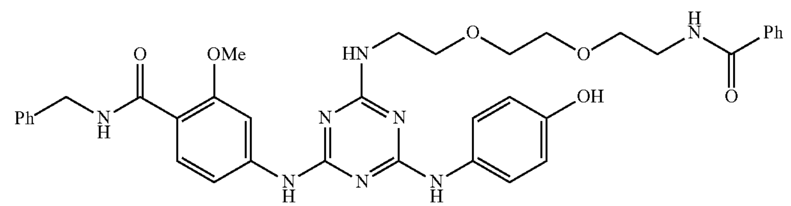 [SMILES: COc1cc(Nc2nc(NCCOCCOCCNC(=O)c3ccccc3)nc(Nc3ccc(O)cc3)n2)ccc1C(=O)NCc1ccccc1] | 806.78 | | | 0.4 | | 16.2 | 80.1 | |
| 82 | 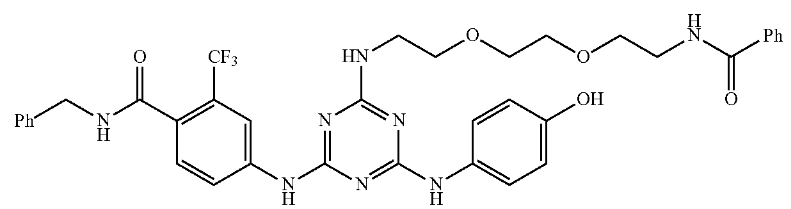 [SMILES: O=C(NCCOCCOCCNc1nc(Nc2ccc(O)cc2)nc(Nc2ccc(C(=O)NCc3ccccc3)c(C(F)(F)F)c2)n1)c1ccccc1] | 844.76 | | | 2.1 | | 5.0 | 47.6 | |
| 83 | 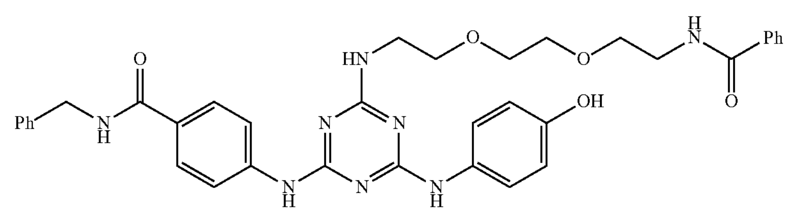 [SMILES: O=C(NCCOCCOCCNc1nc(Nc2ccc(O)cc2)nc(Nc2ccc(C(=O)NCc3ccccc3)cc2)n1)c1ccccc1] | 777.74 | 609 | | 4.1 | | 10.4 | 42.0 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 84 | 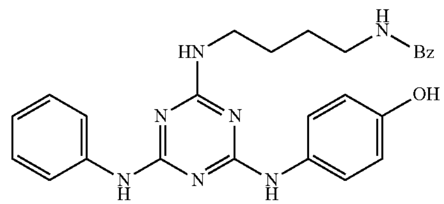 | 583.56 | | | | 5.7 | | 13.7 | 37.1 |
| 85 | 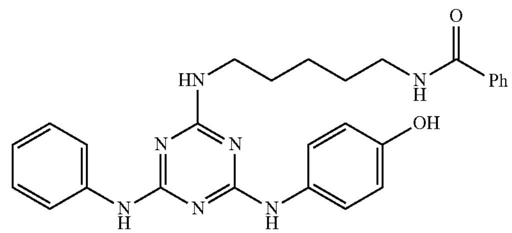 [SMILES: O=C(NCCCCCNc1nc(Nc2ccccc2)nc(Nc2ccc(O)cc2)n1)c1ccccc1] | 597.58 | | | | 7.6 | | 12.2 | 49.6 |
| 86 | 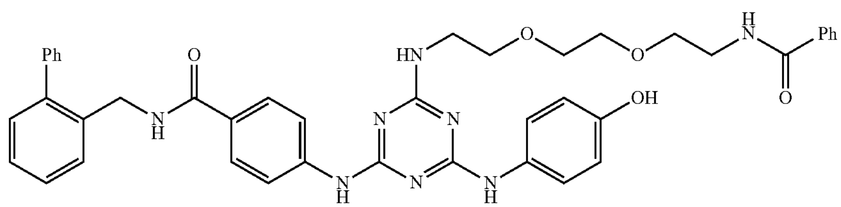 | 806.78 | 870 | 50.0 | 70.7 | | 81.4 | 86.4 | |
| 87 | 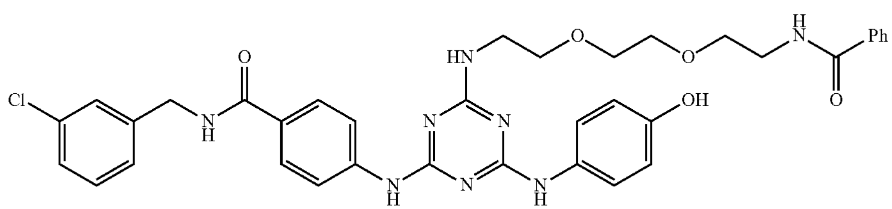 [SMILES: O=C(NCCOCCOCCNc1nc(Nc2ccc(O)cc2)nc(Nc2ccc(C(=O)NCc3cccc(Cl)c3)cc2)n1)c1ccccc1] | 826.82 | 710 | 55.1 | 71.8 | | 83.5 | 90.6 | |

TABLE 1-continued

Inhibitory Activities of PGT Inhibitors

| Cpd ID | Structure | Mol. Weight | IC$_{50}$ (nM) | Inh (% of Ctl) 0.1 µM | Inh (% of Ctl) 0.5 µM | Inh (% of Ctl) 1 µM | Inh (% of Ctl) 2.5 µM | Inh (% of Ctl) 5 µM | Inh (% of Ctl) 10 µM |
|---|---|---|---|---|---|---|---|---|---|
| 88 | (structure with MeO-benzyl) | 842.85 | 820 | 61.8 | 67.6 | | 82.6 | 88.2 | |
| 89 | (structure with naphthyl) | 811.2 | | | 33.8 | | 76.5 | 86.0 | |
| 90 | (structure with Ph-benzyl) | 806.78 | | | 23.4 | | 60.6 | 72.7 | |
| 91 | (structure with Cl-benzyl) | 852.85 | 620 | 60.8 | 72.1 | | 84.0 | 88.0 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 92 | | 815.79 | | | 33.7 | | 71.3 | 80.6 | |
| 93 | | 806.78 | | | 24.6 | | 43.3 | 51.1 | |
| 94 | | 826.82 | | | 36.0 | | 66.7 | 76.1 | |
| 95 | | 668.62 | | | | 1.9 | 23.4 | | 50.4 |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 96 | 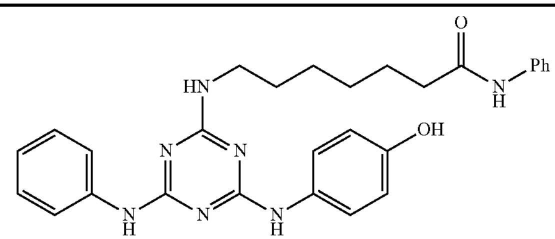 | 611.61 | | | | 8.6 | | 23.9 | 51.9 |
| 97 | 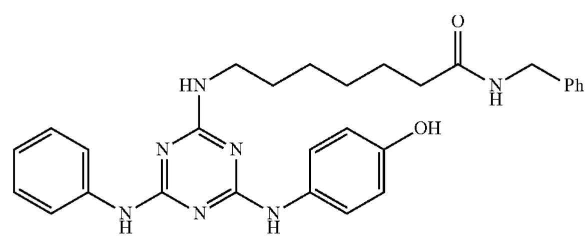 [SMILES: O=C(CCCCCCNc1nc(Nc2ccccc2)nc(Nc2ccc(O)cc2)n1)NCc1ccccc1] | 625.64 | | | | 13.1 | | 19.4 | 30.8 |
| 98 | 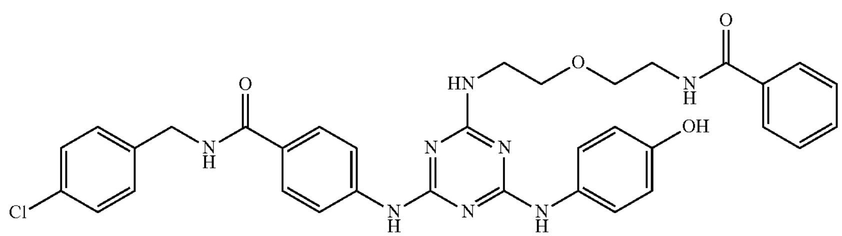 [SMILES: O=C(NCCOCCNc1nc(Nc2ccc(O)cc2)nc(Nc2ccc(C(=O)NCc3ccc(Cl)cc3)cc2)n1)c1ccccc1] | 767.15 | | | 6.7 | | 24.9 | 75.1 | |
| 99 | 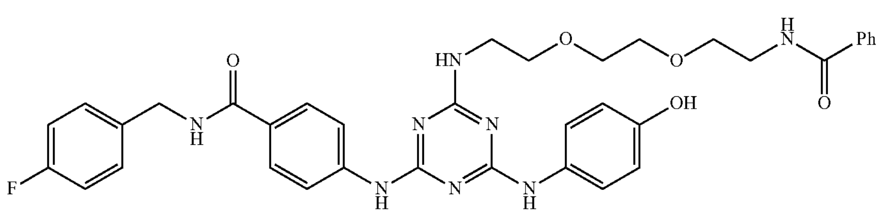 [SMILES: O=C(NCCOCCOCCNc1nc(Nc2ccc(O)cc2)nc(Nc2ccc(C(=O)NCc3ccc(F)cc3)cc2)n1)c1ccccc1] | 794.75 | 23.7 | 81.3 | 61.8 | | 77.1 | 89.4 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 100 | 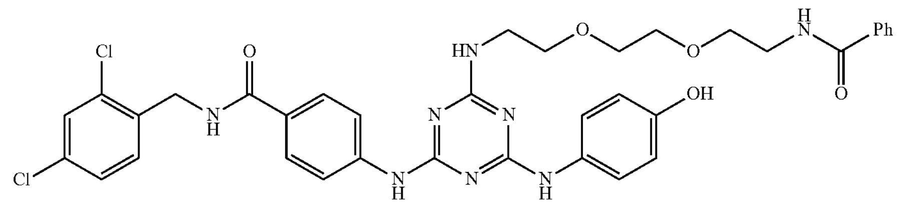 [SMILES: O=C(NCCOCCOCCNc1nc(Nc2ccc(O)cc2)nc(Nc2ccc(C(=O)NCc3ccc(Cl)cc3Cl)cc2)n1)c1ccccc1] | 845.65 | | 41.1 | 56.4 | | 57.6 | 86.0 | |
| 101 | 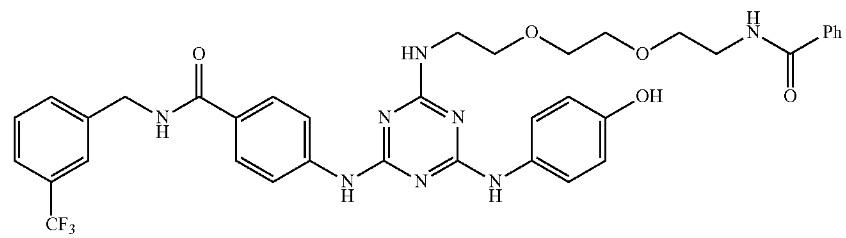 [SMILES: O=C(NCCOCCOCCNc1nc(Nc2ccc(O)cc2)nc(Nc2ccc(C(=O)NCc3cccc(C(F)(F)F)c3)cc2)n1)c1ccccc1] | 844.76 | | 47.4 | 54.0 | | 71.0 | 91.4 | |
| 102 | 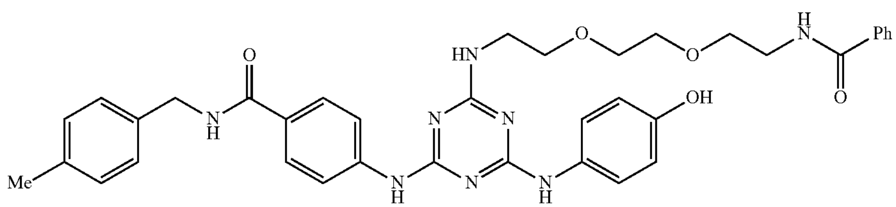 [SMILES: Cc1ccc(CNC(=O)c2ccc(Nc3nc(NCCOCCOCCNC(=O)c4ccccc4)nc(Nc4ccc(O)cc4)n3)cc2)cc1] | 790.78 | | | 41.9 | | 65.7 | 88.0 | |
| 103 | 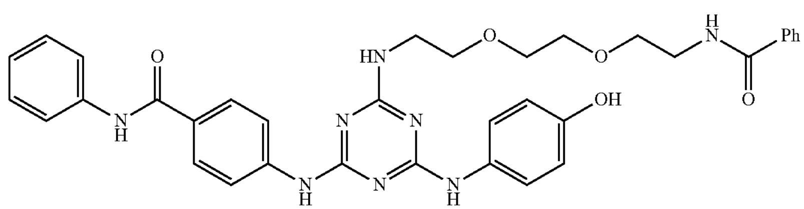 [SMILES: O=C(NCCOCCOCCNc1nc(Nc2ccc(O)cc2)nc(Nc2ccc(C(=O)Nc3ccccc3)cc2)n1)c1ccccc1] | 762.73 | | | 38.3 | | 62.2 | 83.7 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 104 | 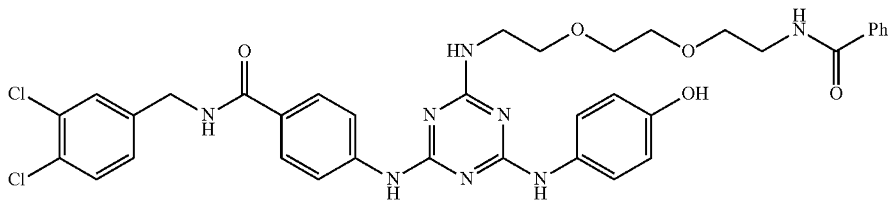 [SMILES: O=C(NCCOCCOCCNc1nc(Nc2ccc(O)cc2)nc(Nc2ccc(C(=O)NCc3ccc(Cl)c(Cl)c3)cc2)n1)c1ccccc1] | 845.65 | 47.5 | 46.6 | 61.6 | | 87.8 | 91.6 | |
| 105 | 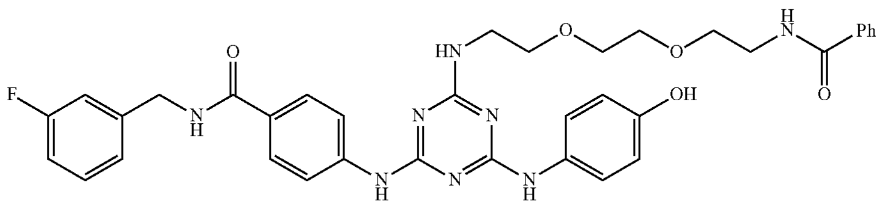 [SMILES: O=C(NCCOCCOCCNc1nc(Nc2ccc(O)cc2)nc(Nc2ccc(C(=O)NCc3cccc(F)c3)cc2)n1)c1ccccc1] | 794.75 | | 67.9 | 64.6 | | 81 | 92.45 | |
| 106 | 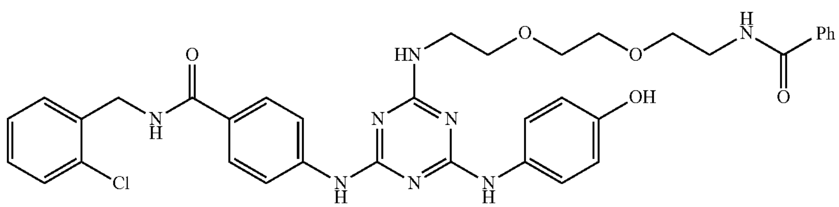 | 811.2 | | 68.4 | 64.8 | | 68.8 | 93.1 | |
| 107 | 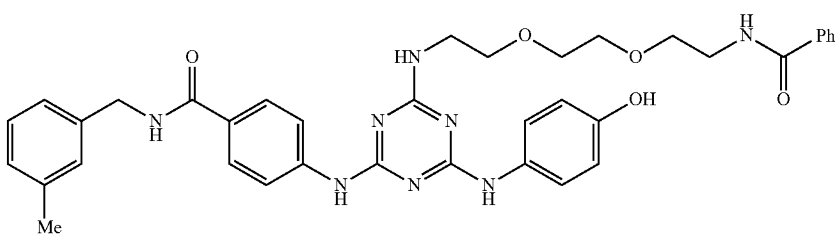 [SMILES: Cc1cccc(CNC(=O)c2ccc(Nc3nc(NCCOCCOCCNC(=O)c4ccccc4)nc(Nc4ccc(O)cc4)n3)cc2)c1] | 790.78 | | 65.2 | 56.3 | | 80.7 | 91.3 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 108 | 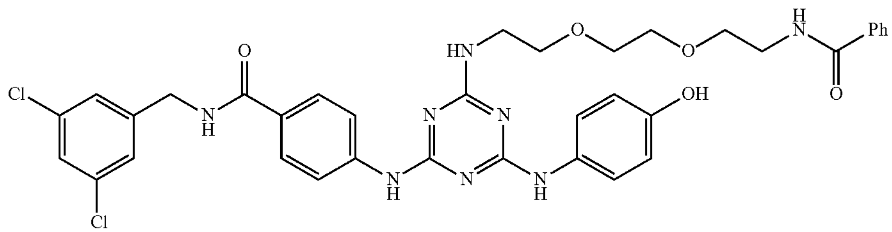 [SMILES: O=C(NCCOCCOCCNc1nc(Nc2ccc(O)cc2)nc(Nc2ccc(C(=O)NCc3cc(Cl)cc(Cl)c3)cc2)n1)c1ccccc1] | 845.65 | | 70.3 | 60.8 | | 78.3 | 76.6 | |
| 109 | 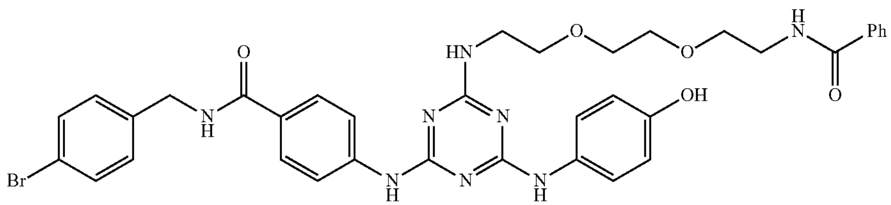 [SMILES: O=C(NCCOCCOCCNc1nc(Nc2ccc(O)cc2)nc(Nc2ccc(C(=O)NCc3ccc(Br)cc3)cc2)n1)c1ccccc1] | 855.65 | 31.3 | 49.5 | 55.6 | | 59.8 | 85.1 | |
| 110 | 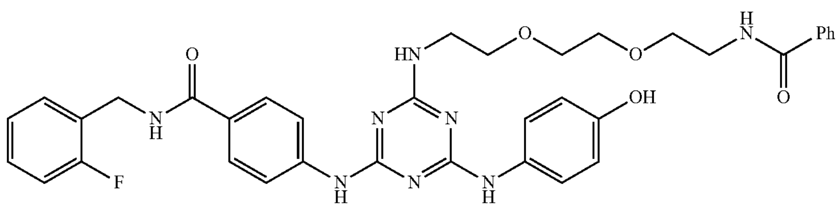 [SMILES: O=C(NCCOCCOCCNc1nc(Nc2ccc(O)cc2)nc(Nc2ccc(C(=O)NCc3ccccc3F)cc2)n1)c1ccccc1] | 794.75 | | 69.6 | 60.6 | | 78.3 | 93.6 | |
| 111 | 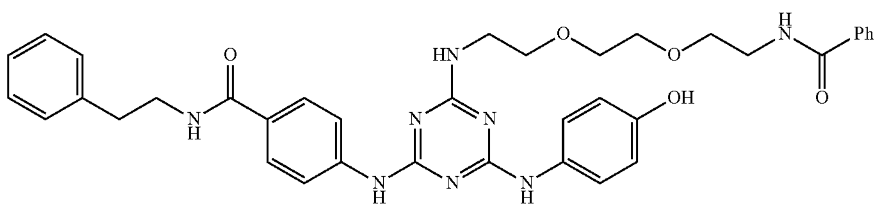 [SMILES: O=C(NCCOCCOCCNc1nc(Nc2ccc(O)cc2)nc(Nc2ccc(C(=O)NCCc3ccccc3)cc2)n1)c1ccccc1] | 790.78 | | 52.2 | 59.1 | | 81.5 | 93.2 | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 112 | 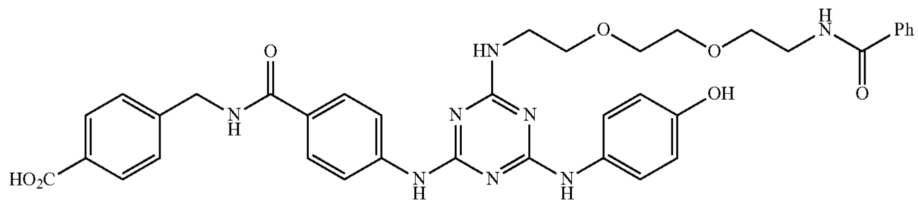 [SMILES: O=C(O)c1ccc(CNC(=O)c2ccc(Nc3nc(NCCOCCOCCNC(=O)c4ccccc4)nc(Nc4ccc(O)cc4)n3)cc2)cc1] | 706.75 | | | 17.5 | | 32.2 | 49.4 | |
| 113 | 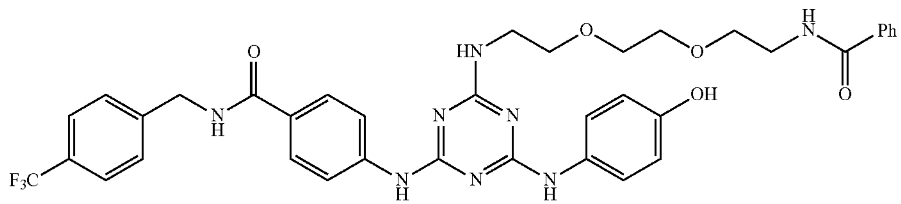 [SMILES: O=C(NCCOCCOCCNc1nc(Nc2ccc(O)cc2)nc(Nc2ccc(C(=O)NCc3ccc(C(F)(F)F)cc3)cc2)n1)c1ccccc1] | 844.76 | | 36.8 | 49.2 | | 84.1 | 92.4 | |
| 114 | 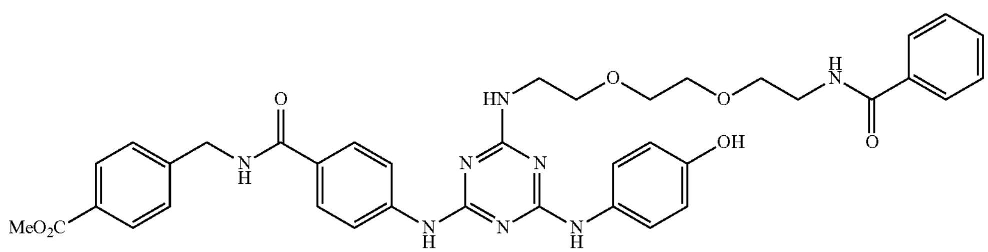 [SMILES: COC(=O)c1ccc(CNC(=O)c2ccc(Nc3nc(NCCOCCOCCNC(=O)c4ccccc4)nc(Nc4ccc(O)cc4)n3)cc2)cc1] | 834.79 | | 41.0 | 61.4 | | | | |
| 115 | 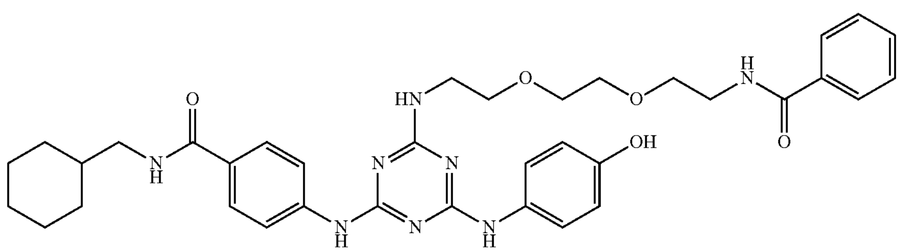 [SMILES: O=C(NCCOCCOCCNc1nc(Nc2ccc(O)cc2)nc(Nc2ccc(C(=O)NCC3CCCCC3)cc2)n1)c1ccccc1] | 782.81 | | 54.4 | 76.8 | | | | |

TABLE 1-continued

Inhibitory Activities of PGT Inhibitors

| Cpd ID | Structure | Mol. Weight | IC$_{50}$ (nM) | Inh (% of Ctl) 0.1 µM | Inh (% of Ctl) 0.5 µM | Inh (% of Ctl) 1 µM | Inh (% of Ctl) 2.5 µM | Inh (% of Ctl) 5 µM | Inh (% of Ctl) 10 µM |
|---|---|---|---|---|---|---|---|---|---|
| 116 | 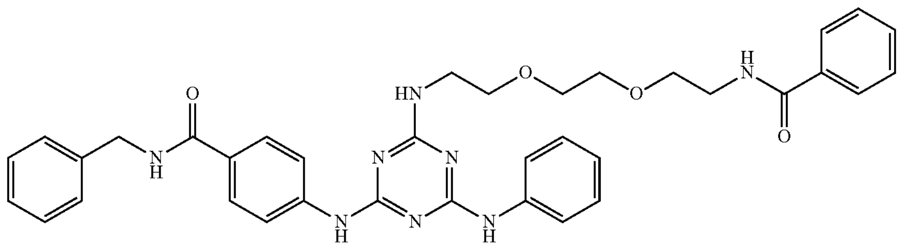 [SMILES: O=C(NCCOCCOCCNc1nc(Nc2ccccc2)nc(Nc2ccc(C(=O)NCc3ccccc3)cc2)n1)c1ccccc1] | 760.76 | | 36.4 | 59.4 | | | | |
| 117 | 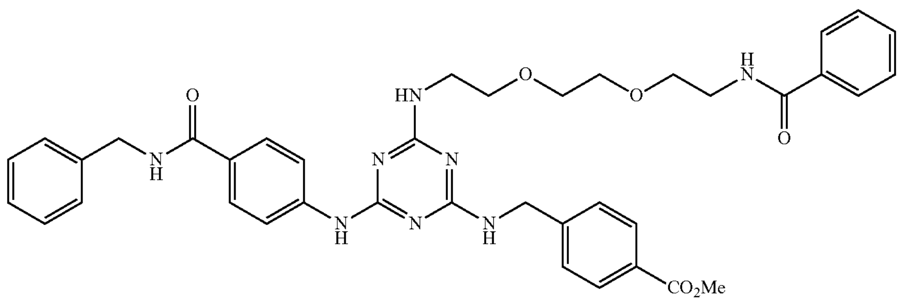 [SMILES: COC(=O)c1ccc(CNc2nc(NCCOCCOCCNC(=O)c3ccccc3)nc(Nc3ccc(C(=O)NCc4ccccc4)cc3)n2)cc1] | 832.82 | | 8.1 | 36.7 | | | | |
| 118 | 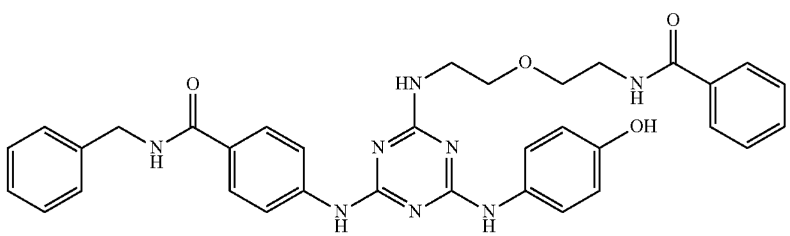 [SMILES: O=C(NCCOCCNc1nc(Nc2ccc(O)cc2)nc(Nc2ccc(C(=O)NCc3ccccc3)cc2)n1)c1ccccc1] | 732.7 | 20.9 | 74.2 | 90.7 | | | | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 119 | | 726.74 | | 57.2 | 81.4 | | | | |
| 120 | | 625.64 | | 11.2 | 29.1 | | | | |
| 121 | | 704.77 | | 1.0 | 28.8 | | | | |
| 122 | | 832.82 | | 5.8 | 38.1 | | | | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 123 | | 790.78 | | 12.0 | 36.6 | | | | |
| 124 | | 790.78 | 34 | 68.8 | 85.4 | | | | |
| 125 | | 704.77 | | 3.2 | 24.3 | | | | |
| 126 | | 812.74 | | 24.0 | 56.3 | 70.0 | | | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 127 | 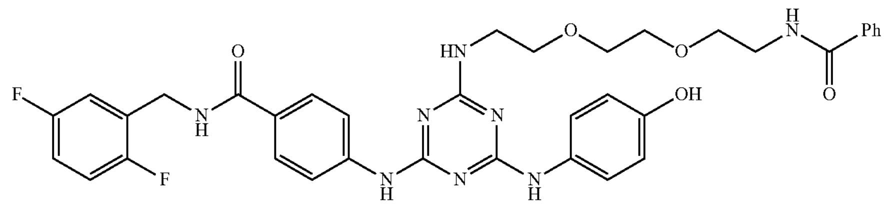 [SMILES: O=C(NCCOCCOCCNc1nc(Nc2ccc(O)cc2)nc(Nc2ccc(C(=O)NCc3cc(F)ccc3F)cc2)n1)c1ccccc1] | 812.74 | | 17.0 | 52.3 | 70.2 | | | |
| 128 | 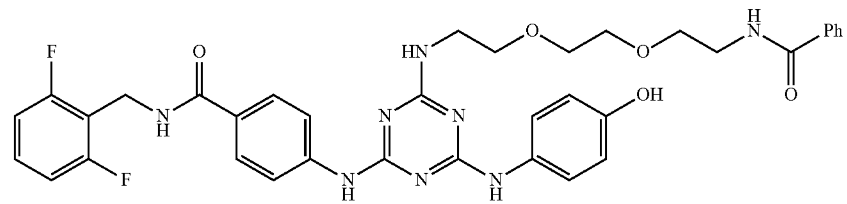 | 812.74 | | 36.6 | 71.8 | 82.2 | | | |
| 129 | 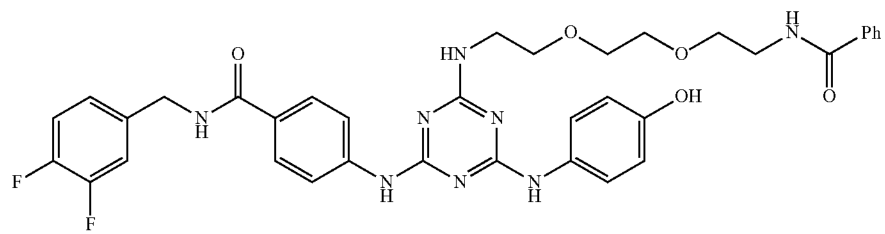 [SMILES: O=C(NCCOCCOCCNc1nc(Nc2ccc(O)cc2)nc(Nc2ccc(C(=O)NCc3ccc(F)c(F)c3)cc2)n1)c1ccccc1] | 812.74 | | 8.9 | 45.1 | 65.6 | | | |
| 130 | 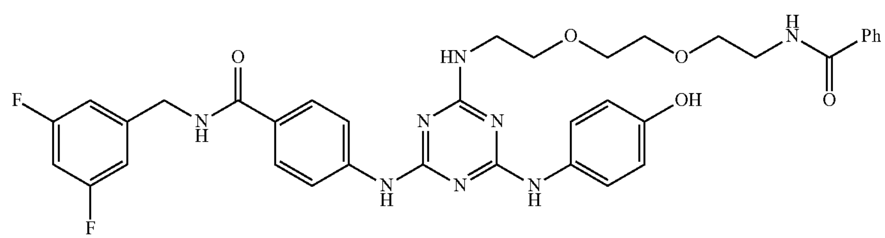 [SMILES: O=C(NCCOCCOCCNc1nc(Nc2ccc(O)cc2)nc(Nc2ccc(C(=O)NCc3cc(F)cc(F)c3)cc2)n1)c1ccccc1] | 812.74 | | 41.6 | 73.2 | 81.7 | | | |

TABLE 1-continued

Inhibitory Activities of PGT Inhibitors

| Cpd ID | Structure | Mol. Weight | IC$_{50}$ (nM) | Inh (% of Ctl) 0.1 µM | Inh (% of Ctl) 0.5 µM | Inh (% of Ctl) 1 µM | Inh (% of Ctl) 2.5 µM | Inh (% of Ctl) 5 µM | Inh (% of Ctl) 10 µM |
|---|---|---|---|---|---|---|---|---|---|
| 131 | 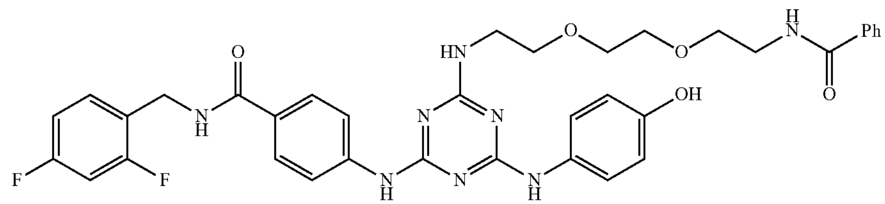 [SMILES: O=C(NCCOCCOCCNc1nc(Nc2ccc(O)cc2)nc(Nc2ccc(C(=O)NCc3ccc(F)cc3F)cc2)n1)c1ccccc1] | 812.74 | | 22.3 | 47.0 | 74.3 | | | |
| 132 | 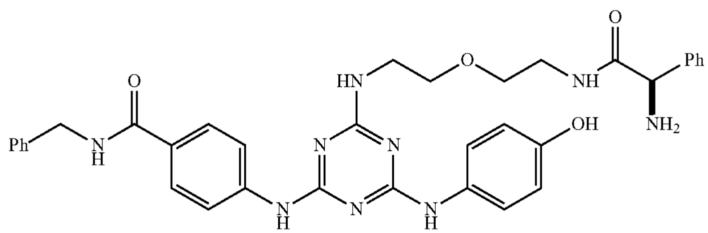 [SMILES: N[C@@H](C(=O)NCCOCCNc1nc(Nc2ccc(O)cc2)nc(Nc2ccc(C(=O)NCc3ccccc3)cc2)n1)c1ccccc1] | 875.77 | | 15.0 | 22.1 | 32.4 | | | |
| 133 | 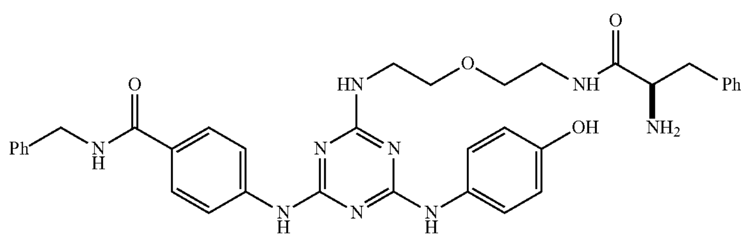 [SMILES: N[C@H](Cc1ccccc1)C(=O)NCCOCCNc1nc(Nc2ccc(O)cc2)nc(Nc2ccc(C(=O)NCc3ccccc3)cc2)n1] | 889.79 | | 4.3 | 12.6 | 19.4 | | | |
| 134 | 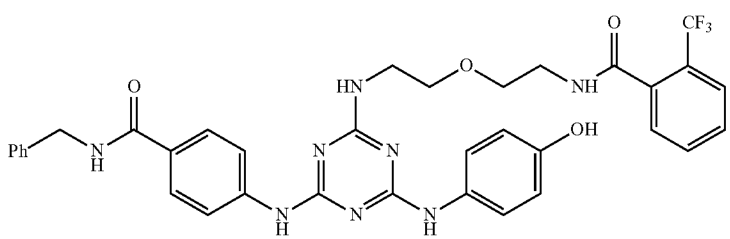 [SMILES: O=C(NCc1ccccc1)c1ccc(Nc2nc(NCCOCCNC(=O)c3ccccc3C(F)(F)F)nc(Nc3ccc(O)cc3)n2)cc1] | 800.7 | | 14.0 | 27.7 | 46.7 | | | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 135 | 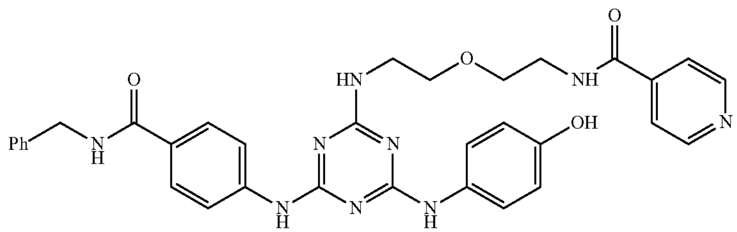 [SMILES: O=C(NCCOCCNc1nc(Nc2ccc(O)cc2)nc(Nc2ccc(C(=O)NCc3ccccc3)cc2)n1)c1ccncc1] | 847.71 | 23.9 | 13.2 | 28.4 | 49.6 | | | |
| 136 | 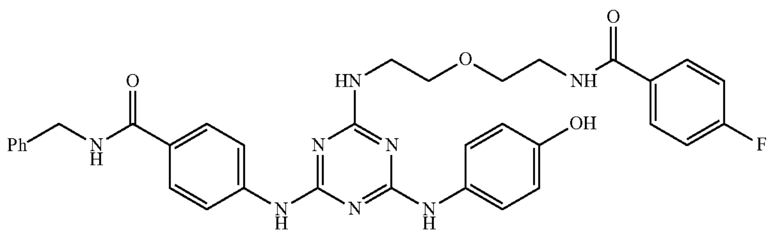 [SMILES: O=C(NCCOCCNc1nc(Nc2ccc(O)cc2)nc(Nc2ccc(C(=O)NCc3ccccc3)cc2)n1)c1ccc(F)cc1] | 750.7 | | 33.3 | 64.1 | 77.9 | | | |
| 137 | 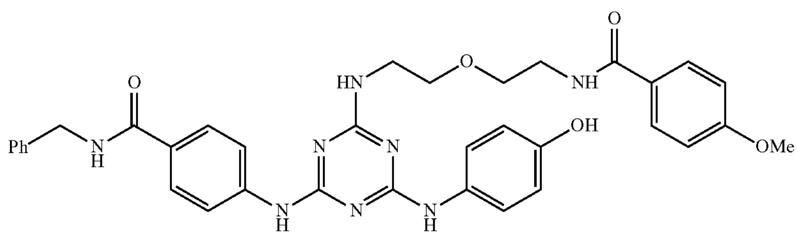 [SMILES: COc1ccc(C(=O)NCCOCCNc2nc(Nc3ccc(O)cc3)nc(Nc3ccc(C(=O)NCc4ccccc4)cc3)n2)cc1] | 762.73 | 36.7 | 42.0 | 64.9 | 75.6 | | | |
| 138 | 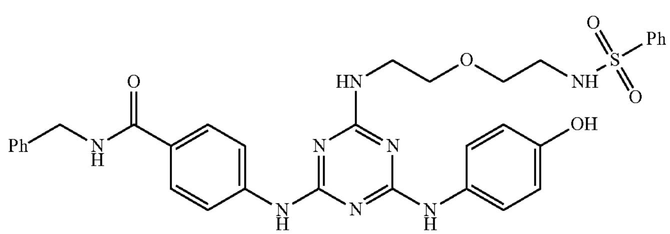 [SMILES: O=C(NCc1ccccc1)c1ccc(Nc2nc(NCCOCCNS(=O)(=O)c3ccccc3)nc(Nc3ccc(O)cc3)n2)cc1] | 768.76 | | 17.8 | 22.5 | 34.5 | | | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 139 | 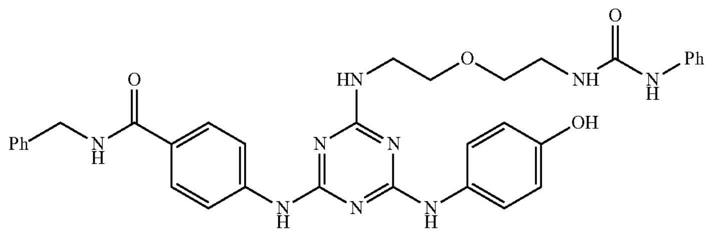 [SMILES: O=C(NCCOCCNc1nc(Nc2ccc(O)cc2)nc(Nc2ccc(C(=O)NCc3ccccc3)cc2)n1)Nc1ccccc1] | 747.72 | | 16.3 | 30.7 | 39.0 | | | |
| 140 | 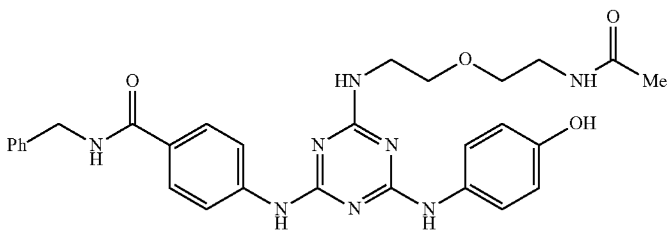 [SMILES: CC(=O)NCCOCCNc1nc(Nc2ccc(O)cc2)nc(Nc2ccc(C(=O)NCc3ccccc3)cc2)n1] | 670.64 | | 11.5 | 4.5 | 10.9 | | | |
| 141 | 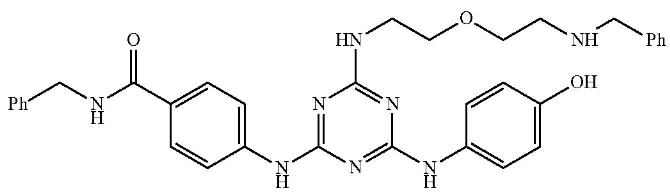 [SMILES: O=C(NCc1ccccc1)c1ccc(Nc2nc(NCCOCCNCc3ccccc3)nc(Nc3ccc(O)cc3)n2)cc1] | 718.72 | | 12.7 | 22.0 | 43.5 | | | |
| 142 | 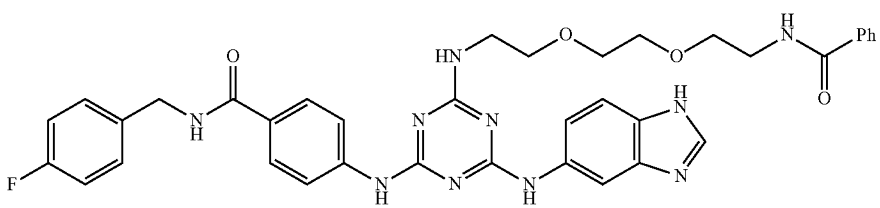 [SMILES: O=C(NCCOCCOCCNc1nc(Nc2ccc(C(=O)NCc3ccc(F)cc3)cc2)nc(Nc2ccc3[nH]cnc3c2)n1)c1ccccc1] | 932.79 | | 8.4 | 20.1 | 39.2 | | | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 143 (85% pure) | 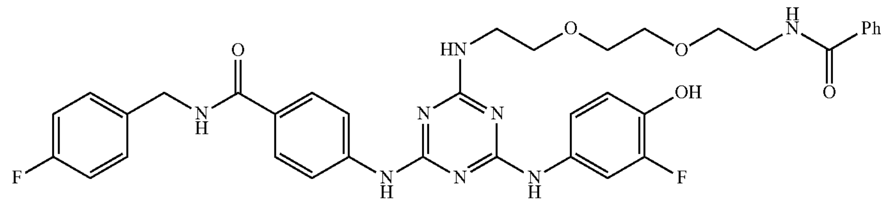 [SMILES: O=C(NCCOCCOCCNc1nc(Nc2ccc(C(=O)NCc3ccc(F)cc3)cc2)nc(Nc2ccc(O)c(F)c2)n1)c1ccccc1] | 812.74 | 16.5 | 33.7 | 57.8 | 69.5 | | | |
| 144 | 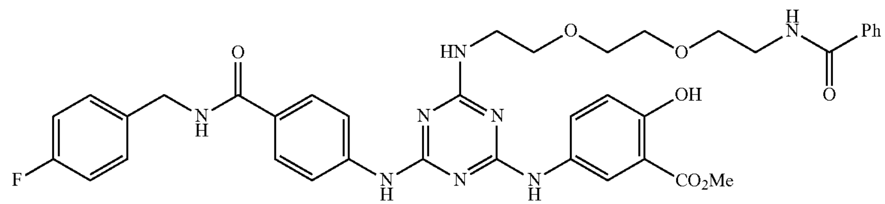 [SMILES: COC(=O)c1cc(Nc2nc(NCCOCCOCCNC(=O)c3ccccc3)nc(Nc3ccc(C(=O)NCc4ccc(F)cc4)cc3)n2)ccc1O] | 852.78 | | 3.4 | 5.8 | 10.8 | | | |
| 145 | 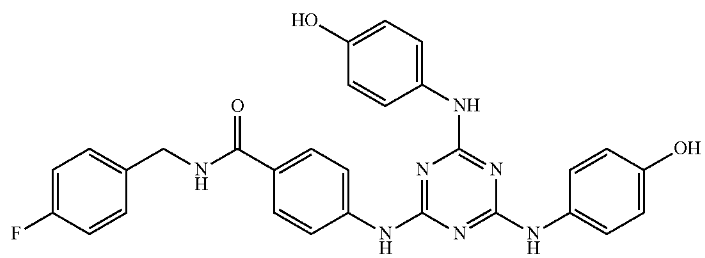 [SMILES: O=C(NCc1ccc(F)cc1)c1ccc(Nc2nc(Nc3ccc(O)cc3)nc(Nc3ccc(O)cc3)n2)cc1] | 651.56 | | 7.1 | 3.1 | 6.9 | | | |
| 146 | 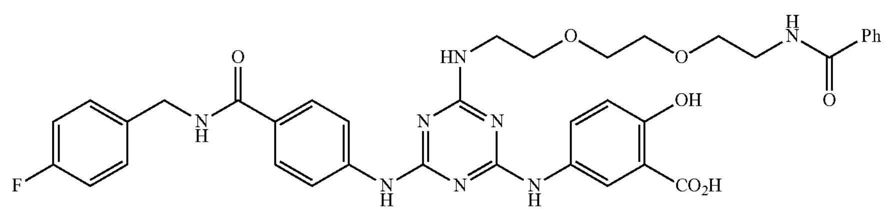 [SMILES: O=C(NCCOCCOCCNc1nc(Nc2ccc(C(=O)NCc3ccc(F)cc3)cc2)nc(Nc2ccc(O)c(C(=O)O)c2)n1)c1ccccc1] | 724.74 | 44.8 | 28.5 | 59.8 | 70.4 | | | |

TABLE 1-continued

Inhibitory Activities of PGT Inhibitors

| Cpd ID | Structure | Mol. Weight | IC$_{50}$ (nM) | Inh (% of Ctl) 0.1 µM | Inh (% of Ctl) 0.5 µM | Inh (% of Ctl) 1 µM | Inh (% of Ctl) 2.5 µM | Inh (% of Ctl) 5 µM | Inh (% of Ctl) 10 µM |
|---|---|---|---|---|---|---|---|---|---|
| 147 | 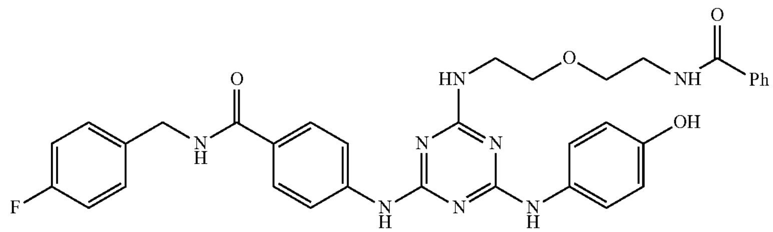 [SMILES: O=C(NCCOCCNc1nc(Nc2ccc(O)cc2)nc(Nc2ccc(C(=O)NCc3ccc(F)cc3)cc2)n1)c1ccccc1] | 750.7 | 31.7 | 44.5 | 70.2 | 79.5 | | | |
| 148 | 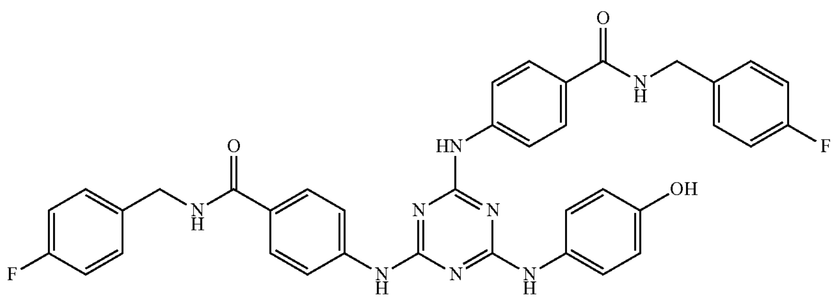 [SMILES: O=C(NCc1ccc(F)cc1)c1ccc(Nc2nc(Nc3ccc(O)cc3)nc(Nc3ccc(C(=O)NCc4ccc(F)cc4)cc3)n2)cc1] | 786.7 | | 8.4 | 12.9 | 20.7 | | | |
| 149 | 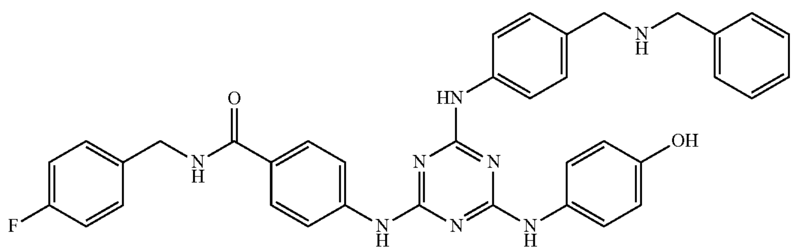 [SMILES: O=C(NCc1ccc(F)cc1)c1ccc(Nc2nc(Nc3ccc(O)cc3)nc(Nc3ccc(CNCc4ccccc4)cc3)n2)cc1] | 868.75 | | 3.8 | 9.1 | 17.6 | | | |

TABLE 1-continued

Inhibitory Activities of PGT Inhibitors

| Cpd ID | Structure | Mol. Weight | IC$_{50}$ (nM) | Inh (% of Ctl) 0.1 μM | Inh (% of Ctl) 0.5 μM | Inh (% of Ctl) 1 μM | Inh (% of Ctl) 2.5 μM | Inh (% of Ctl) 5 μM | Inh (% of Ctl) 10 μM |
|---|---|---|---|---|---|---|---|---|---|
| 150 | 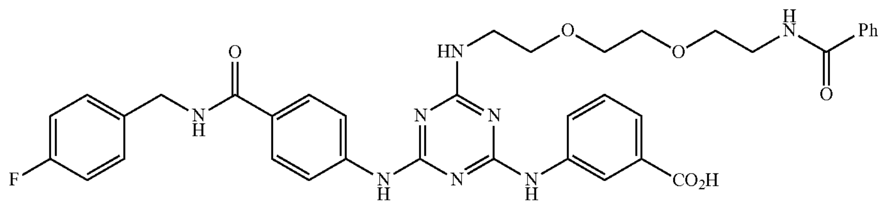 [SMILES: O=C(O)c1cccc(Nc2nc(NCCOCCOCCNC(=O)c3ccccc3)nc(Nc3ccc(C(=O)NCc4ccc(F)cc4)cc3)n2)c1] | 708 | | 4.2 | 14.3 | 23.9 | | | |
| 151 | 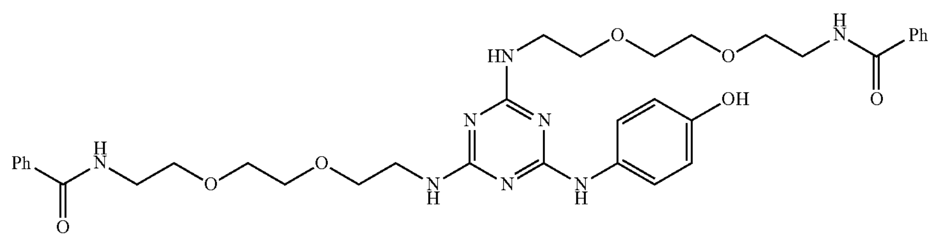 [SMILES: O=C(NCCOCCOCCNc1nc(NCCOCCOCCNC(=O)c2ccccc2)nc(Nc2ccc(O)cc2)n1)c1ccccc1] | | | | 0.7 | 8.4 | | | |

C. Acceleration of Wound Healing by Inhibitors of Prostaglandin Transporter (PGT)

Studies were conducted using compound T26A (Table 1). Two full-thickness wounds with diameter of 5 mm were created on the back of mice symmetrically under the shoulder blades. 50 µL vehicle (2% DMSO+2% cremophor in water) was applied to one wound (FIG. 1A, top panel), and that of 2 mM T26A was applied to the other (FIG. 1A, bottom panel), immediately after surgery and every other day afterwards. T26A accelerates wound healing as shown over a 10 day period in FIG. 1A. T26A increased vascularization and blood flow in the wound. FIG. 1B shows averaged wound areas of 4 mice, each of them had 2 wounds and received topically applied vehicle Veh1 (2% DMSO+2% cremophor in water) on one wound and T26A on the other. On the wounds of a separate group of 4 mice, vehicle Veh2 (2% EtOH, yellow) was applied to one wound and 200 µM $PGE_2$ (green) was applied to the other. Results were statistically significant ($p<0.05$, T26A vs. vehicle).

REFERENCES

Alm A (1998) Prostaglandin derivates as ocular hypotensive agents. *Progress in Retinal and Eye Research* 17:291-312.

Bao Y, Pucci M L, Chan B O, Lu R, Ito S and Schuster V L (2002) Prostaglandin transporter PGT is expressed in cell types that synthesize and release prostanoids. *American Journal of Physiology* 282:F1103-1110.

Bito L Z and Salvador E V (1976) Effects of anti-inflammatory agents and some other drugs on prostaglandin biotransport. *J. Pharmacol. Exp. Ther.* 198:481-488.

Blatteis C M and Sehic E (1997) Fever: How may circulating pyrogens signal the brain? *News in Physiological Sciences.* 12:1-9.

Bley K R, Hunter J C, Eglen R M and Smith J A (1998) The role of IP prostanoid receptors in inflammatory pain. *Trends Pharmacol Sci* 19:141-147.

Bos C L, Richel D J, Ritsema T, Peppelenbosch M P and Versteeg H H (2004) Prostanoids and prostanoid receptors in signal transduction. *Int J Biochem Cell Biol* 36:1187-1205.

Chi Y, Khersonsky S M, Chang Y T, Schuster V L. Identification of a new class of prostaglandin transporter inhibitors and characterization of their biological effects on prostaglandin E2 transport. J Pharmacol Exp Ther. 2006 March; 316(3): 1346-50. Epub 2005 November 3.

Chi Y, Min J, Jasmin J-F, Duranski M, Seki Y, Nomura T, Folkert I W, Charron M J, Lisanti M, Lefer D J, Chang Y-T, Schuster V L. A small molecule inhibitor of the prostaglandin transporter PGT lowers blood pressure by vasodilation and natriuresis and inhibits platelet aggregation. Manuscript, 2009.

Clyman R1, Mauray F, Roman C and Rudolph A M (1978) PGI2 is a more potent vasodilator of the lamb ductus arteriosus than is either PGI2 or 6 keto PGF1alpha. *Prostaglandins* 16:259-264.

Coceani F and Olley P M (1988) The control of cardiovascular shunts in the fetal and perinatal period. *Can J Physiol Pharmacol* 66:1129-1134.

Endo S, Nomura T, Chan B S, Lu R, Pucci M L, Bao Y and Schuster V L (2002) Expression of PGT in MDCK cell monolayers: polarized apical localization and induction of active PG transport. *American Journal of Physiology* 282:F618-F622.

Epstein M (1986) *Prostaglandins and the kidney. American journal of medicine*; v. 80, no. 1A, 1986. Technical Publishing, New York, N.Y.

Ferrara N and Davis-Smyth T (1997) The biology of vascular endothelial growth factor. *Endocr Rev* 18: 4-25.

Helliwell R J, Adams L F and Mitchell M D (2004) Prostaglandin synthases: recent developments and a novel hypothesis. *Prostaglandins Leukotrienes and Essential Fatty Acids* 70:101-113.

Jacquemin E, Hagenbuch B, Stieger B, Wolkoff A W and Meier P J (1994) Expression cloning of a rat liver $Na^+$-independent organic anion transporter. *Proc Natl Acad Sci USA* 91:133-137.

Kanai N, Lu R, Satriano J A, Bao Y, Wolkoff A W and Schuster V L (1995) Identification and characterization of a prostaglandin transporter. *Science* 268:866-869.

Mann J R, Backlund M G, Buchanan F G, Daikoku T, Holla V R, Rosenberg D W, Dey S K, and DuBois R N (2006) Repression of prostaglandin dehydrogenase by epidermal growth factor and snail increases prostaglandin E2 and promotes cancer progression. *Cancer Res* 66: 6649-56.

Narumiya S, Sugimoto Y and Ushikubi F (1999) Prostanoid receptors: structures, properties, and functions. *Physiological Reviews* 79:1193-1226.

Nomura T, Lu R, Pucci M L and Schuster V L (2004) The two-step model of prostaglandin signal termination: in vitro reconstitution with the prostaglandin transporter and prostaglandin 15 dehydrogenase. *Mol Pharmacol* 65:973-978.

Samad T A, Sapirstein A and Woolf C J (2002) Prostanoids and pain: unraveling mechanisms and revealing therapeutic targets. *Trends Mol Med* 8:390-396.

Seybold V S, Jia Y P, and Abrahams L G. Cyclo-oxygenase-2 contributes to central sensitization in rats with peripheral inflammation. Pain. 2003 September; 105(1-2):47-55.

Schuster V L (2002) Prostaglandin Transport. *Prostaglandins and Other Lipid Mediators* 68-69:633=647.

Shao J, Sheng G G, Mifflin R C, Powell D W, and Sheng H (2006) Roles of myofibroblasts in prostaglandin E2-stimulated intestinal epithelial proliferation and angiogenesis. *Cancer Res* 66: 846-55.

Sheng H, Shao J, Washington M K, and DuBois R N (2001) Prostaglandin E2 increases growth and motility of colorectal carcinoma cells. J Biol Chem 276: 18075-81.

Smith G C S, Coleman R A and McGrath J C (1994) Characterization of dilator prostanoid receptors in the fetal rabbit ductus arteriosus. *Journal of Pharmacology & Experimental Therapeutics* 271:390-396.

Southall M D and Vasko M R (2000) Prostaglandin E(2)-mediated sensitization of rat sensory neurons is not altered by nerve growth factor. Neurosci Lett 287: 33-36.

Southall M D and Vasko M R (2001) Prostaglandin receptor subtypes, EP3C and EP4, mediate the prostaglandin E2-induced cAMP production and sensitization of sensory neurons. J Biol Chem 276: 16083-91.

Stjernschantz J (1995) Prostaglandins as ocular hypotensive agents; development of an analogue for glaucoma treatment. *Advances in Prostaglandin Thromboxane and Leukotriene Research* 23:63-68.

Stjernschantz J (2004) Studies on ocular inflammation and development of a prostaglandin analogue for glaucoma treatment. *Experimental Eye Research* 78:759-766.

Susanna R, Jr., Chew P and Kitazawa Y (2002) Current status of prostaglandin therapy: latanoprost and unoprostone. *Survey in Ophthalmology* 47 Suppl 1:S97-104.

Sweet D H, Wolff N A and Pritchard J B (1997) Expression cloning and characterization of ROAT1. The basolateral organic anion transporter in rat kidney. *J. Biol. Chem.* 272: 30088-30095.

Tsujii M, Kawano S, Tsuji S, Sawaoka H, Hori M, and DuBois R N (1998) Cyclooxygenase regulates angiogenesis induced by colon cancer cells. *Cell* 93: 705-716.

Ulmann A, Silvestre L, Chemama L, Rezvani Y, Renault M, Aguillaume C J. and Baulieu E E (1992) Medical termination of early pregnancy with mifepristone (RU 486) followed by a prostaglandin analogue. Study in 16,369 women. *Acta Obstet. Gynec. Scand.* 71:278-283.

Vanegas H and Schaible H G (2001) Prostaglandins and cyclooxygenases [correction of cycloxygenases] in the spinal cord. *Prog Neurobiol* 64:327-363.

Wang J L, Cheng H F, Zhang M Z, McKanna J A and Harris R C (1998) Selective increase of cyclooxygenase-2 expression in a model of renal ablation. *Am. J. Physiol.* 275:F613-F622.

Yokoyama C, Yabuki T, Shimonishi M, Wada M, Hatae T, Ohkawara S, Takeda J, Kinoshita T, Okabe M and Tanabe T (2002) Prostacyclin-deficient mice develop ischemic renal disorders, including nephrosclerosis and renal infarction. *Circulation* 106:2397-2403.

Young M R (2004) Tumor-derived prostaglandin E2 and transforming growth factor-beta stimulate endothelial cell motility through inhibition of protein phosphatase-2A and involvement of PTEN and phosphatidylinositide 3-kinase. *Angiogenesis* 7: 123-131.

U.S. Pat. No. 5,792,851, issued Aug. 11, 1998, Human Prostaglandin Transporter, Schuster et al.

PCT International Patent Application Publication No. WO 2007/136638 A2, published Nov. 29, 2007, Prostaglandin Transporter Inhibitors.

What is claimed is:

1. A compound having the structure:

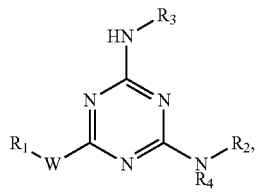

wherein W is O or NR5;

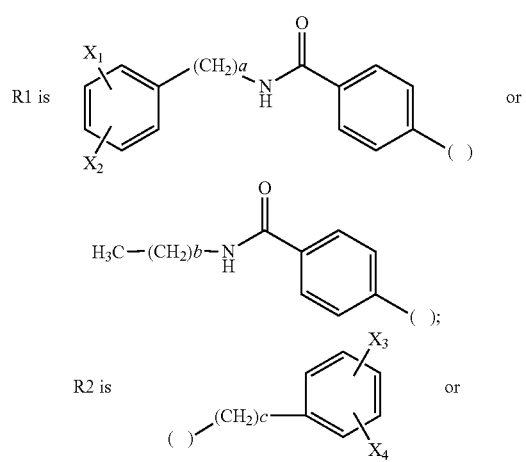

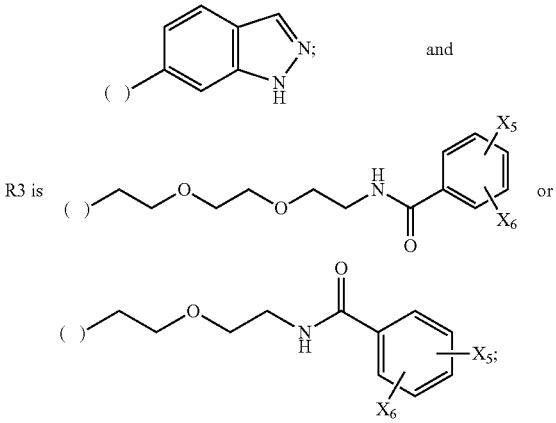

$R4$ and $R5$ are independently H or $-CH_3$;

$R6$ is O or NR9;

$R7$ is H, $-CH_3$, $-C(CH_3)_3$, $-CH_2OH$, $-(CH_2)_2OH$, $-(CH_2)_2O(CH_2)_2OH$, $-(CH_2CH_2O)_3CH_3$, $-(CH_2CH_2O)_2CH_2CO_2CH_3$, $-(CH_2)_5CH_3$,

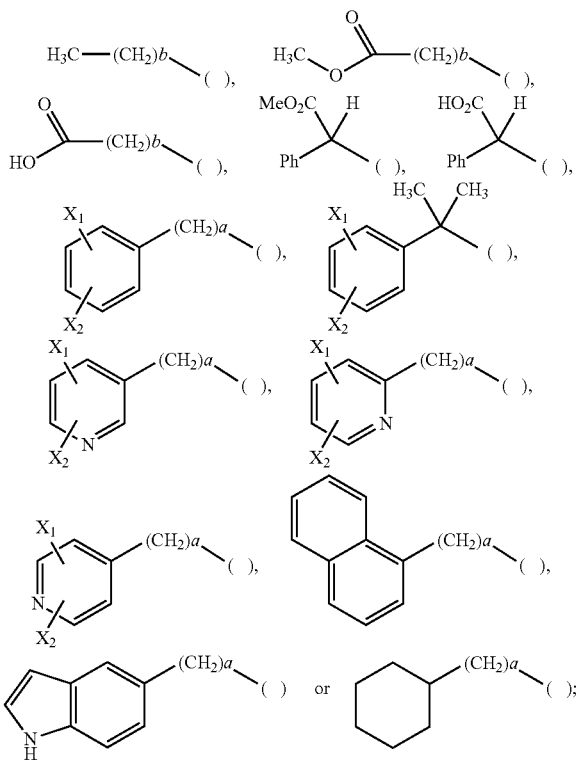

$R8$ is H, $-OH$, $-CH_2OH$, $-CO_2H$, $-CO_2CH_2CH_3$, $-CO(CH_2)_6CH_3$, $-OCH_3$, $-NH_2$, $-SO_2NH_2$, $-CONH-Bn$ or

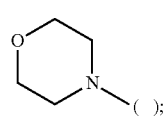

R9 is H or —CH₃;
R10 is —CH₂NH₂, —CO₂H or —CO₂CH₃;
R11 is —SO₂-Ph, —CH₂-Ph, —CONH-Ph, —COCH₃,

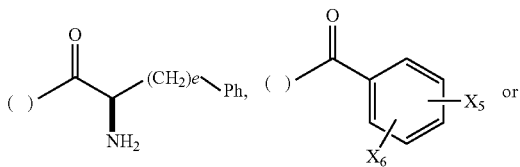

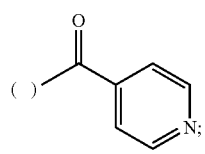

and
R12 is —CH₃,

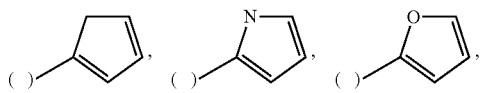

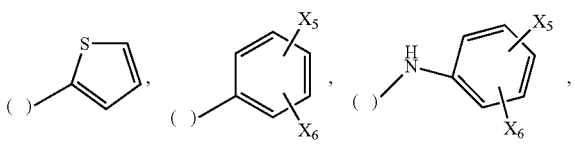

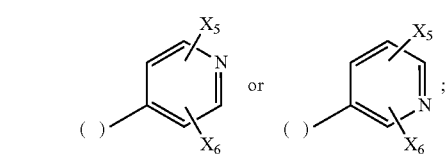

where X1, X2, X3, X4, X5 and X6 are independently H, halogen, —OH, —CH₃, —CF₃, —OCH₃, —CO₂H, —CO₂CH₃, —CH₂CO₂H or —CH₂CO₂CH₃;
where X7 is independently H, halogen, —OH, —CH₃, —CF₃, —OCH₃, —CO₂H, —CO₂CH₃, —CH₂CO₂H, —CH₂CO₂CH₃, phenyl or —O-Bn; and
where a=1-2; b=1-5; c=0-1; d=4-7; and e=0-1;
or a pharmaceutically acceptable salt thereof.

2. The compound of claim 1, wherein W is NR5.
3. The compound of claim 1, wherein R6 is NR9.
4. The compound of claim 1, wherein at least one of R4, R5 and R9 is H.
5. The compound of claim 1, wherein all of R4, R5 and R9 are H.
6. The compound of claim 1, wherein R8 is located in para position.
7. The compound of claim 1, wherein one of X1 and X2 is H, and the other is halogen, —CF₃, —CH₃, —CO₂H, —CO₂CH₃, —OCH₃ or phenyl.
8. The compound of claim 1, wherein both X1 and X2 are halogen.

9. The compound of claim 1, wherein one of X3 and X4 is H, and the other is halogen, —CO₂H, —CO₂CH₃, —CH₂CO₂H, —CH₂CO₂CH₃, —OH, —OCH₃ or —O-Bn.
10. The compound of claim 1, wherein one of X3 and X4 is —OH, and the other is halogen, —CO₂H or —CO₂CH₃.
11. The compound of claim 1, wherein one of X5 and X6 is H, and the other is halogen, —CF₃, —OCH₃ or phenyl.
12. The compound of claim 1, wherein both X5 and X6 are halogen.
13. The compound of claim 1, wherein X7 is H, —CF₃ or —OCH₃.
14. The compound of claim 1, wherein one or both of X1 and X2 are located in ortho position.
15. The compound of claim 1, wherein one or both of X1 and X2 are located in meta position.
16. The compound of claim 1, wherein X1 is located in meta position and X2 is located in para position.
17. The compound of claim 1, wherein X1 is located in ortho position and X2 is located in para position.
18. The compound of claim 1, wherein X3 is in meta position and X4 is in para position.
19. The compound of claim 1, wherein X5 or X6 is in meta position.
20. The compound of claim 1, wherein X5 or X6 is in para position.
21. The compound of claim 1 having the structure:

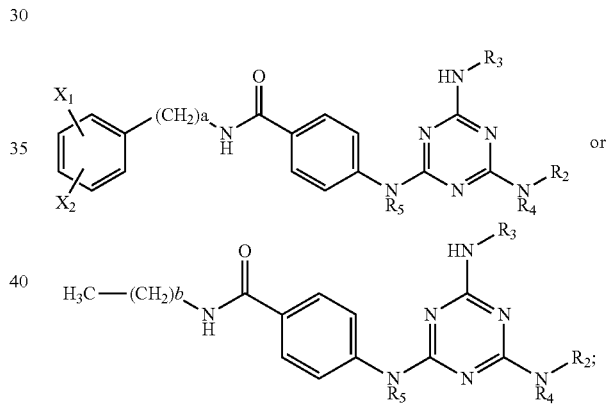

or a pharmaceutically acceptable salt thereof.
22. The compound of claim 1 having the structure:

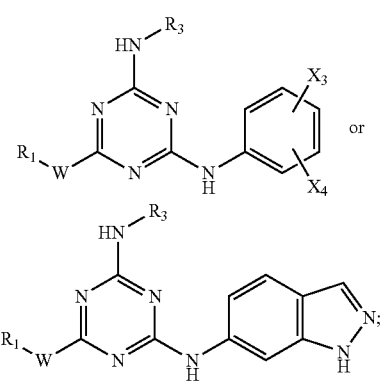

or a pharmaceutically acceptable salt thereof.

23. The compound of claim 1 having the structure:

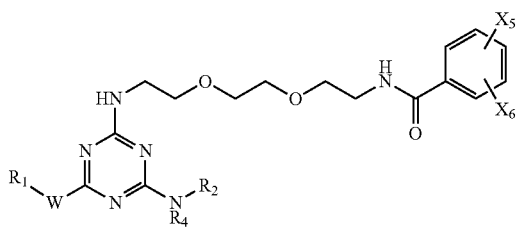

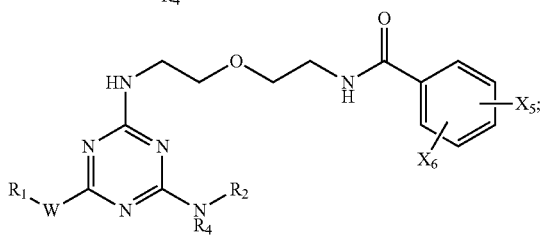

or a pharmaceutically acceptable salt thereof.

24. The compound of claim 1, wherein
R1 is

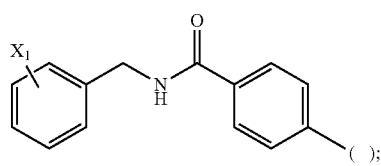

R2 is

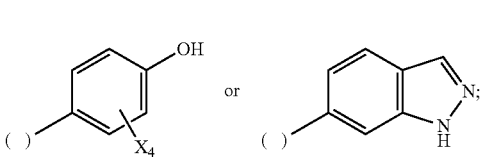

and
R3 is

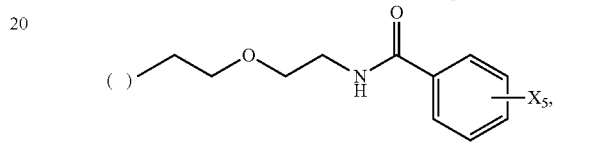

and
where X1 is H or halogen;
where X4 is H, halogen or —CO$_2$H; and
where X5 is H, halogen or —OCH$_3$;
or a pharmaceutically acceptable salt thereof.

25. The compound of claim 1, where R5 is H.

26. The compound of claim 1 having the structure:

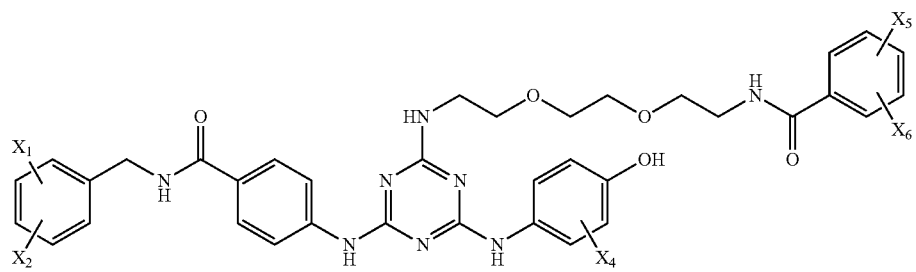

or a pharmaceutically acceptable salt thereof.

27. The compound of claim 1, wherein the halogen is Br, Cl or F.

28. The compound of claim 1 having the structure:

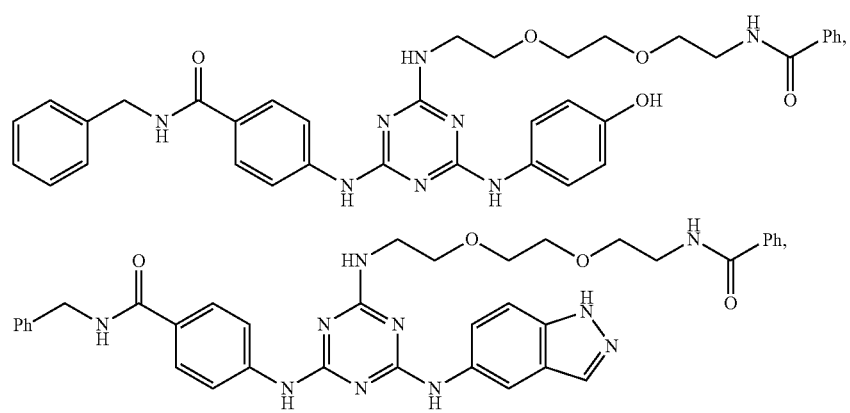

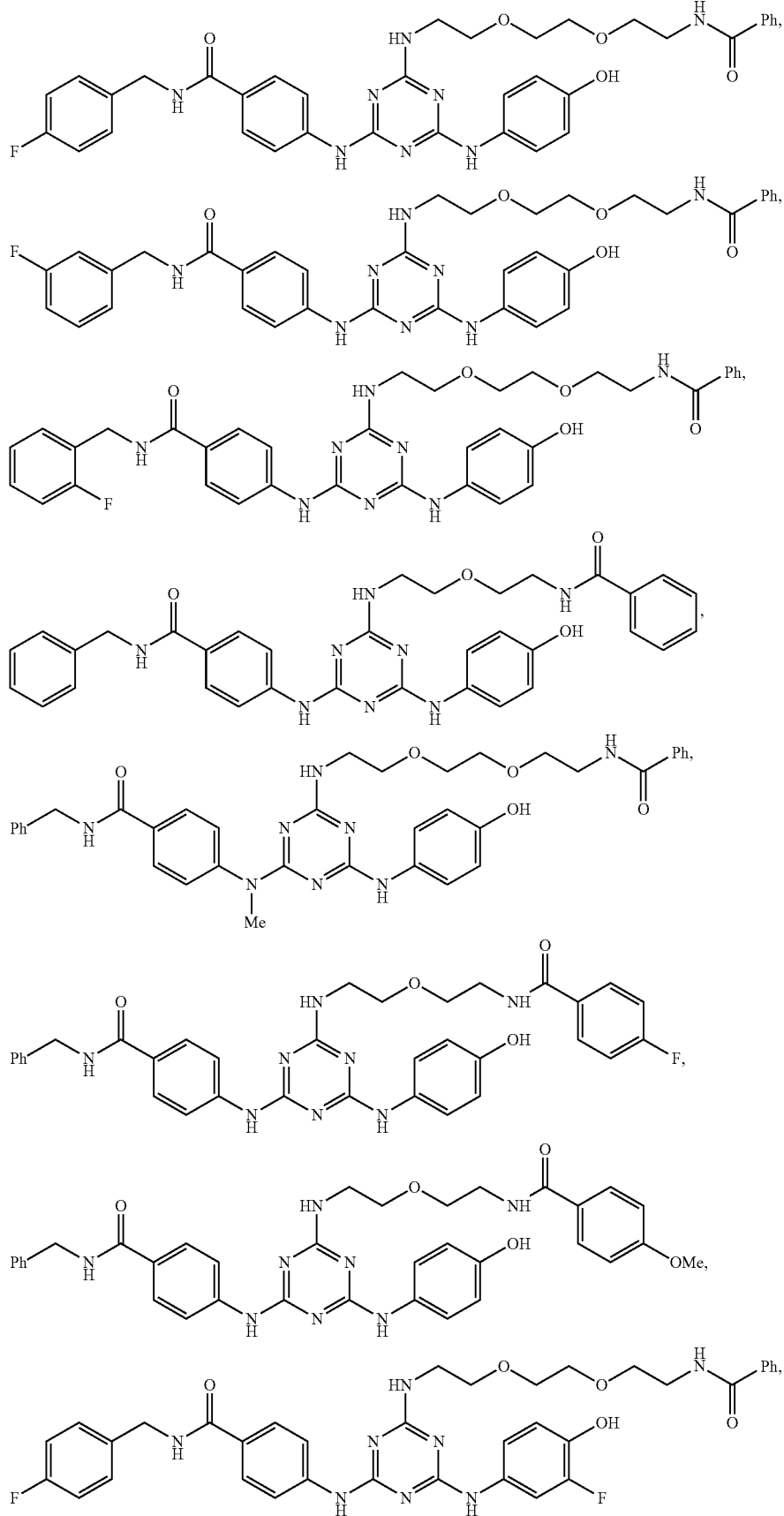

-continued

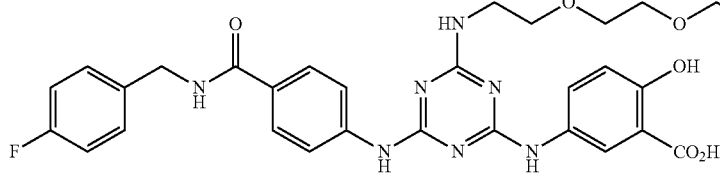

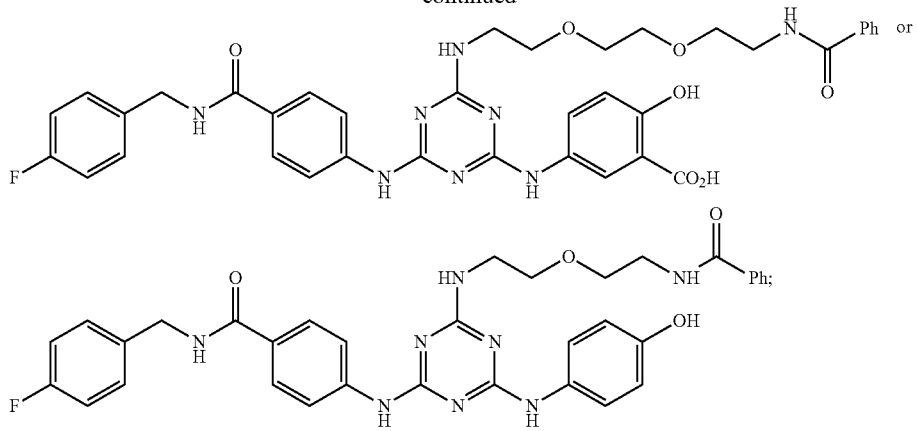

or a pharmaceutically acceptable salt thereof.

29. A pharmaceutical composition comprising the compound of claim 1 and a pharmaceutically acceptable carrier.

30. A method of treating rheumatoid arthritis in a subject comprising administering a compound of claim 1 to the subject in an amount effective to treat rheumatoid arthritis.

31. A compound having the structure:

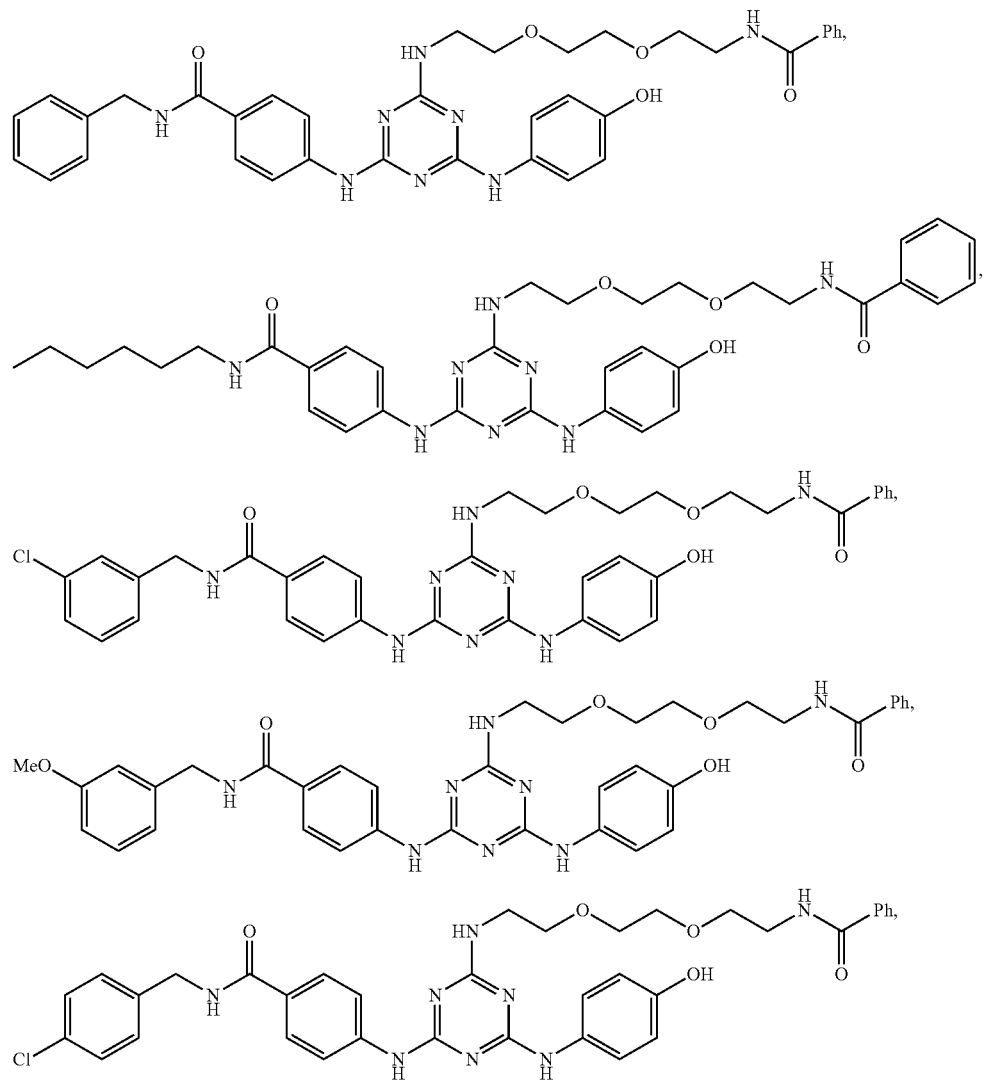

-continued
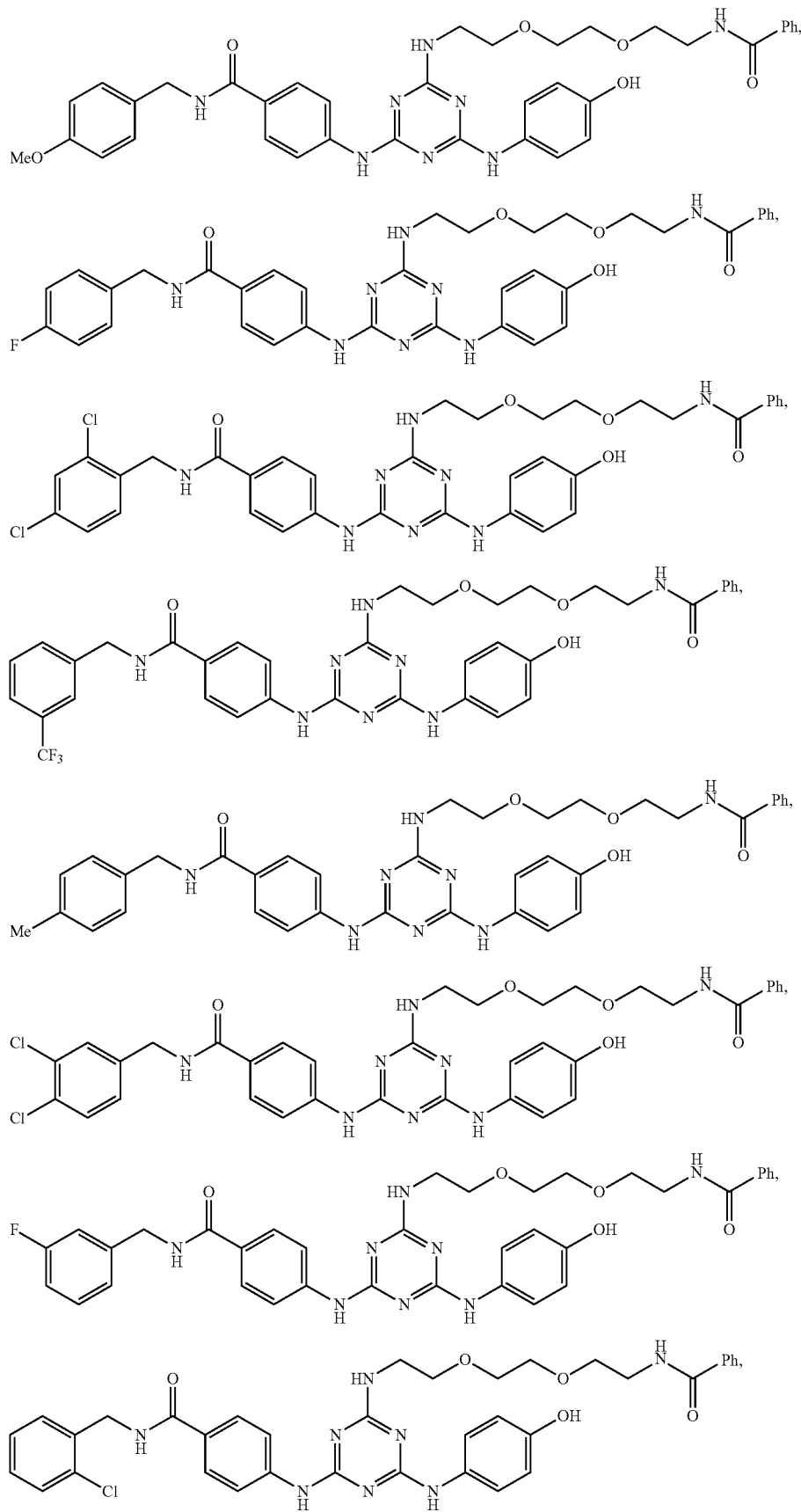

-continued
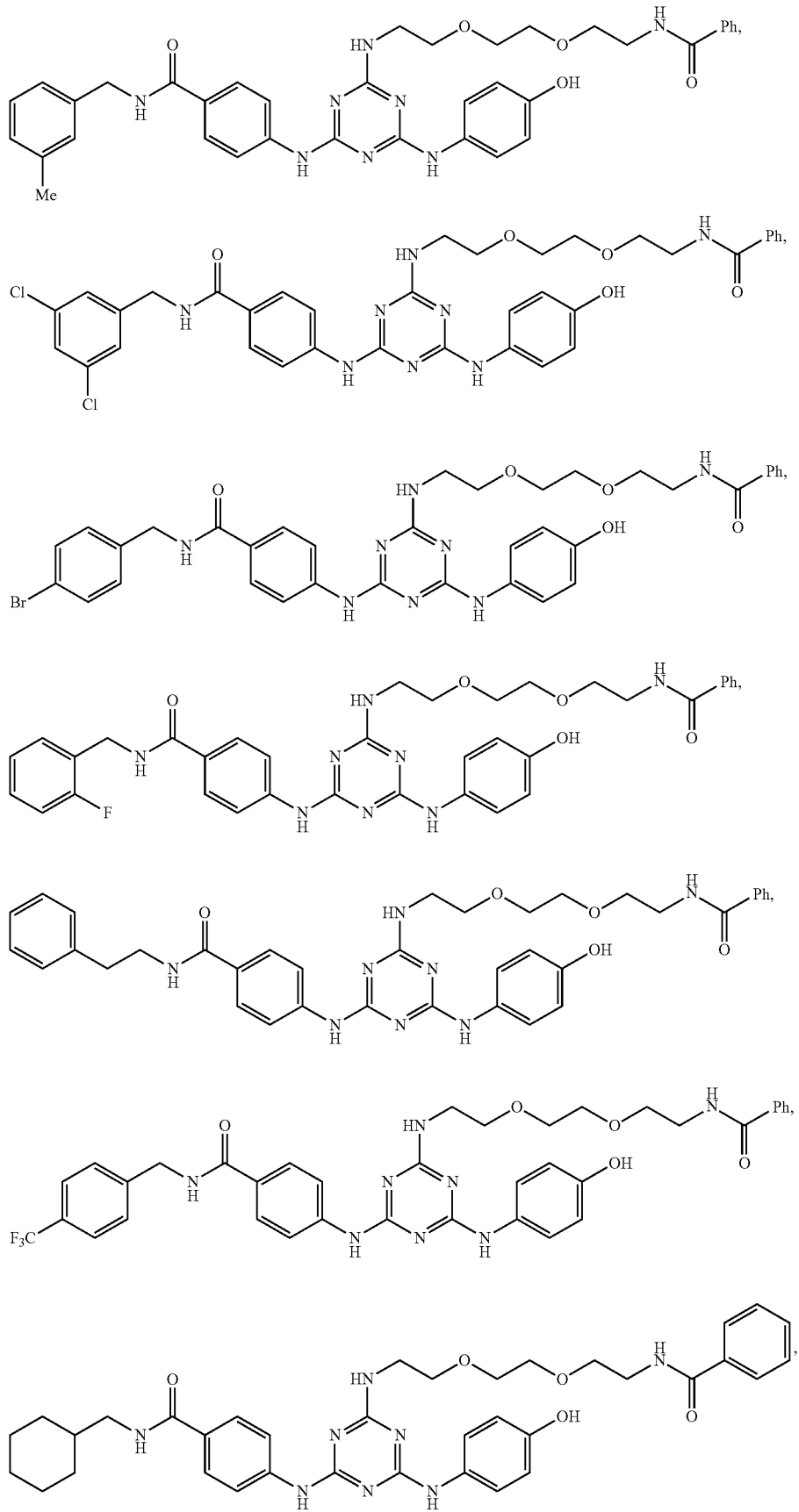

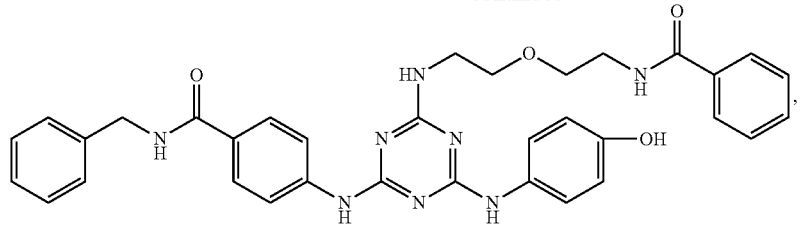
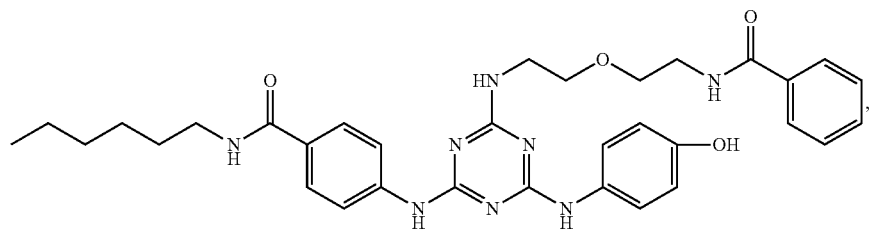
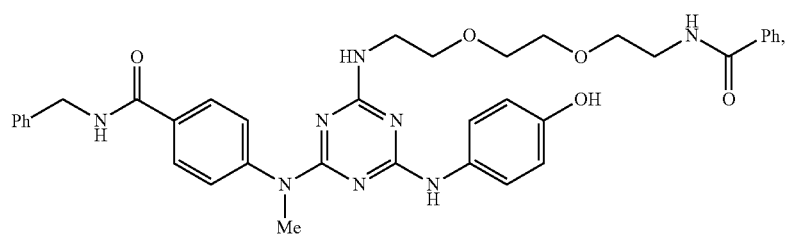
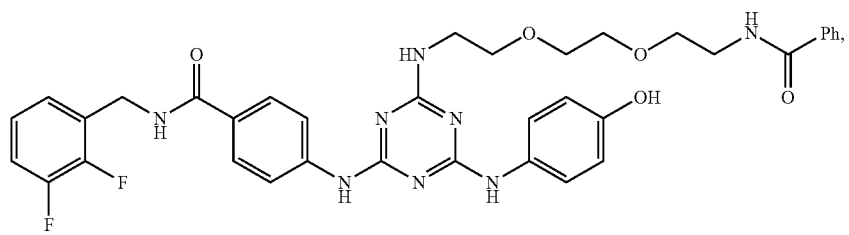
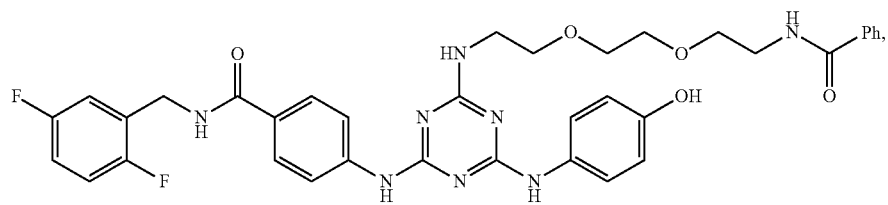
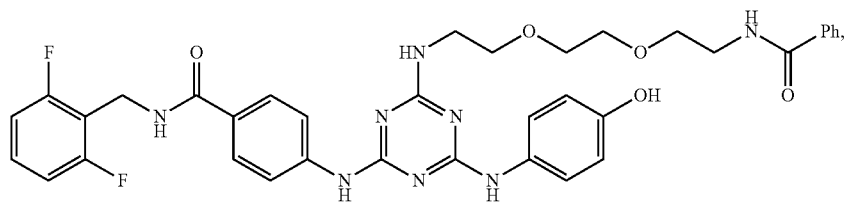
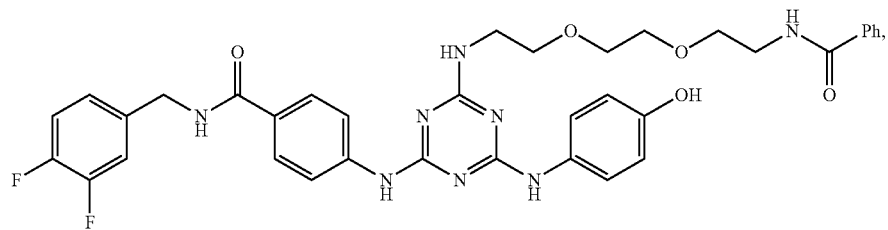

-continued
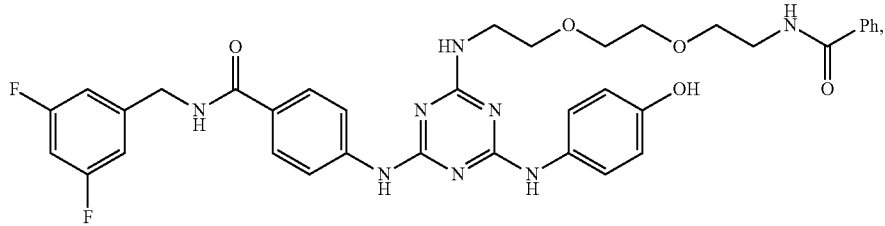
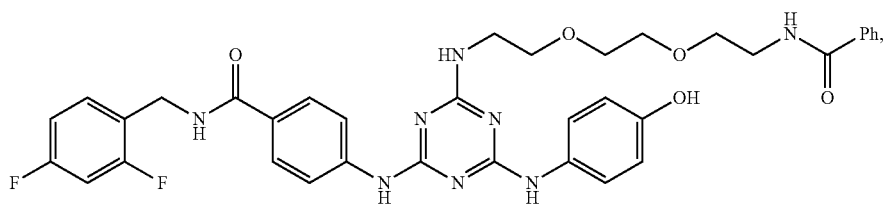
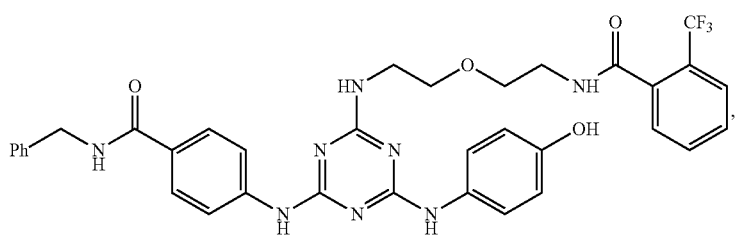
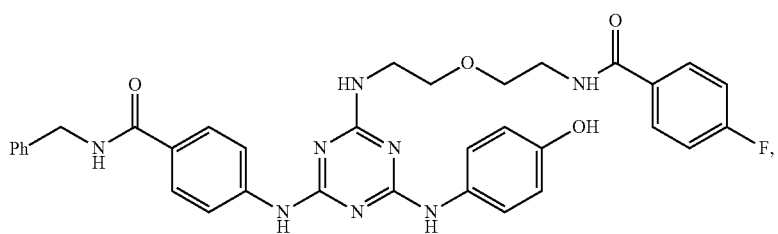
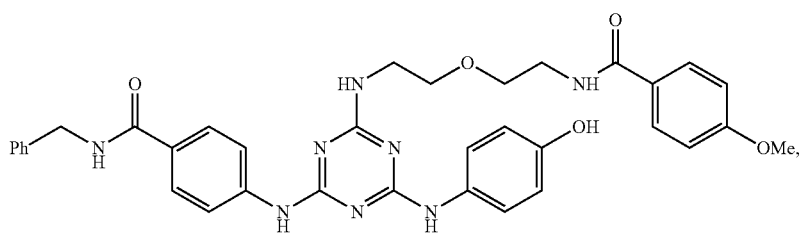
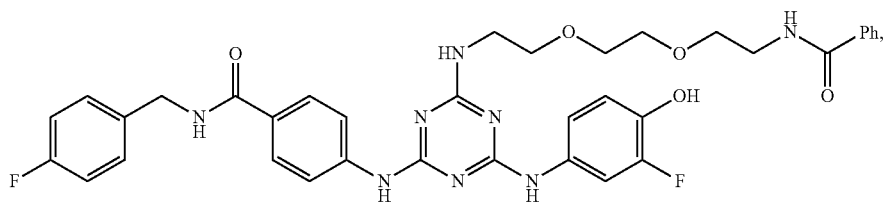
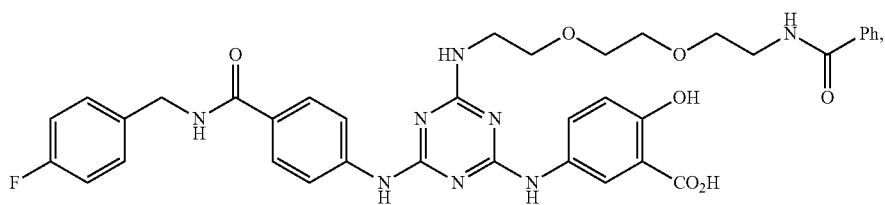
or

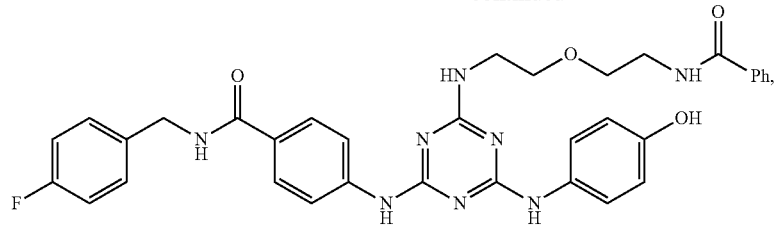
or a pharmaceutically acceptable salt thereof.

UNITED STATES PATENT AND TRADEMARK OFFICE
CERTIFICATE OF CORRECTION

| | | Page 1 of 1 |
|---|---|---|
| PATENT NO. | : 8,952,150 B2 | |
| APPLICATION NO. | : 13/394857 | |
| DATED | : February 10, 2015 | |
| INVENTOR(S) | : Victor L. Schuster et al. | |

It is certified that error appears in the above-identified patent and that said Letters Patent is hereby corrected as shown below:

Specification

In Column 1, after line 14, add:

-- STATEMENT OF GOVERNMENT SUPPORT

This invention was made with government support under grant number DK049688 awarded by the National Institutes of Health. The government has certain rights in the invention. --

Signed and Sealed this
Eighth Day of December, 2015

Michelle K. Lee
*Director of the United States Patent and Trademark Office*